US008299112B2

(12) United States Patent
Smith et al.

(10) Patent No.: US 8,299,112 B2
(45) Date of Patent: Oct. 30, 2012

(54) ESTROGEN RECEPTOR MODULATORS AND USES THEREOF

(75) Inventors: Nicholas D. Smith, San Diego, CA (US); Mehmet Kahraman, La Jolla, CA (US); Steven P. Govek, San Diego, CA (US); Johnny Y. Nagasawa, San Diego, CA (US); Andiliy G. Lai, San Diego, CA (US); Jackaline D. Julien, Del Mar, CA (US); Celine Bonnefous, San Diego, CA (US)

(73) Assignee: Aragon Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 13/234,035

(22) Filed: Sep. 15, 2011

(65) Prior Publication Data

US 2012/0071535 A1 Mar. 22, 2012

Related U.S. Application Data

(60) Provisional application No. 61/446,967, filed on Feb. 25, 2011, provisional application No. 61/410,727, filed on Nov. 5, 2010, provisional application No. 61/383,659, filed on Sep. 16, 2010.

(30) Foreign Application Priority Data

Mar. 15, 2011 (GB) .................................... 11 04288

(51) Int. Cl.
*A61K 31/416* (2006.01)
*C07D 231/56* (2006.01)
(52) U.S. Cl. ...................... 514/406; 548/361.1
(58) Field of Classification Search .................. 514/406; 548/361.1
See application file for complete search history.

(56) References Cited

U.S. PATENT DOCUMENTS

| | | | |
|---|---|---|---|
| 5,681,835 | A | 10/1997 | Willson |
| 5,877,219 | A | 3/1999 | Willson |
| 5,968,697 | A | 10/1999 | Tomiuchi et al. |
| 6,207,716 | B1 | 3/2001 | Willson |
| 6,222,073 | B1 | 4/2001 | Herwig et al. |
| 6,313,297 | B1 | 11/2001 | Herwig et al. |
| 2001/0053774 | A1 | 12/2001 | Willson |
| 2007/0232620 | A1 | 10/2007 | Dorsch et al. |
| 2007/0292545 | A1 | 12/2007 | Monte et al. |
| 2008/0255089 | A1 | 10/2008 | Katamreddy |
| 2009/0253895 | A1 | 10/2009 | Eichen et al. |
| 2009/0263438 | A1 | 10/2009 | Melander et al. |

FOREIGN PATENT DOCUMENTS

| | | | |
|---|---|---|---|
| GB | 2483736 | 3/2012 | |
| JP | 07003256 | 1/1995 | |
| JP | 2008-156313 | 7/2008 | |
| JP | 2009-187820 | 8/2009 | |
| WO | WO 99-07668 | 2/1999 | |
| WO | WO 99-36388 | 7/1999 | |
| WO | WO 99-36412 | 7/1999 | |
| WO | WO 01-36360 | 5/2001 | |
| WO | WO 01-44194 | 6/2001 | |
| WO | WO 01-77057 | 10/2001 | |
| WO | WO 03-016270 | 2/2003 | |
| WO | WO 03-103686 | 12/2003 | |
| WO | WO 2005-033056 | 4/2005 | |
| WO | WO-2006-081230 | 8/2006 | |
| WO | WO 2008/057857 | * 5/2008 | ................... 514/406 |
| WO | WO 2008-107455 | 9/2008 | |
| WO | WO 2010-059658 | 5/2010 | |
| WO | WO 2010-077603 | 7/2010 | |
| WO | WO 2010-144959 | 12/2010 | |
| WO | WO 2012-037410 | 3/2012 | |
| WO | WO 2012-037411 | 3/2012 | |

OTHER PUBLICATIONS

Bentrem et al., "Molecular Mechanism of Action at Estrogen Receptor α of a New Clinically Relevant Antiestrogen (GW7604) Related to Tamoxifen," Endocrinology, vol. 142, No. 2, pp. 838-846 (2001).
Dardes et al, "Effects of a New Clinically Relevant Antiestrogen (GW5638) Related to Tamoxifen on Breast and Endometrial Cancer Growth in Vivo," Clinical Cancer Research, vol. 8, pp. 1995-2001 (1995).
MacGregor et al., "Basic Guide to the Mechanisms of Antiestrogen Action," Pharmacological Reviews, vol. 50, No. 2, pp. 151-196 (1998).
Reid et al., "Cyclic, Proteasome-Mediated Turnover of Unliganded and Liganded ERα on Responsive Promoters is an integral Feature of Estrogen Signaling," Molecular Cell, vol. II, pp. 695-707 (2003).
Tamrazi et al., "Molecular Sensors of Estrogen Receptor Conformations and Dynamics," Molecular Endocrinology, 17(12): 5893-2602 (2003).
Welboren et al "Genomic actions of estrogen receptor α: what are the targets and how are they regulated?" Endocrine-Related Cancer, 16, pp. 1073-1089 (2009).
Wijayaratne et al., "Comparative Analyses of Mechanistic Differences Among Antiestrogens," Endocrinology, vol. 140, No. 12, pp. 5828-5840 (1999).
Willson et al., "Dissection of the Molecular Mechanism of Action of GW5638, a Novel Estrogen Receptor Ligand, Provides Insights into the Role of Estrogen Receptor in Bone," Endocrinology, vol. 138, No. 9, pp. 3901-3911 (1997).
PCT/US2011/051843 International Search Report and Written Opinion dated Apr. 26, 2012.
PCT/US2011/051845 International Search Report and Written Opinion dated Apr. 26, 2012.

* cited by examiner

*Primary Examiner* — Rebecca Anderson
*Assistant Examiner* — Samantha Shterengarts
(74) *Attorney, Agent, or Firm* — Wilson Sonsini Goodrich & Rosati

(57) ABSTRACT

Described herein are compounds that are estrogen receptor modulators. Also described are pharmaceutical compositions and medicaments that include the compounds described herein, as well as methods of using such estrogen receptor modulators, alone and in combination with other compounds, for treating diseases or conditions that are mediated or dependent upon estrogen receptors.

12 Claims, No Drawings

ESTROGEN RECEPTOR MODULATORS AND USES THEREOF

RELATED APPLICATIONS

This application claims the benefit of U.S. provisional patent application No. 61/383,659 entitled "ESTROGEN RECEPTOR MODULATORS AND USES THEREOF" filed on Sep. 16, 2010; U.S. provisional patent application No. 61/410,727 entitled "ESTROGEN RECEPTOR MODULATORS AND USES THEREOF" filed on Nov. 5, 2010; U.S. provisional patent application No. 61/446,967 entitled "ESTROGEN RECEPTOR MODULATORS AND USES THEREOF" filed on Feb. 25, 2011; United Kingdom Patent Application No 11 04288.4 entitled "ESTROGEN RECEPTOR MODULATORS AND USES THEREOF" filed on Mar. 15, 2011; each of which is incorporated by reference in its entirety.

FIELD OF THE INVENTION

Described herein are compounds, including pharmaceutically acceptable salts, solvates, metabolites, prodrugs thereof, methods of making such compounds, pharmaceutical compositions comprising such compounds, and methods of using such compounds to treat, prevent or diagnose diseases or conditions that are estrogen sensitive, estrogen receptor dependent or estrogen receptor mediated.

BACKGROUND OF THE INVENTION

The estrogen receptor ("ER") is a ligand-activated transcriptional regulatory protein that mediates induction of a variety of biological effects through its interaction with endogenous estrogens. Endogenous estrogens include 17β-estradiol and estrones. ER has been found to have two isoforms, ER-α and ER-β. Estrogens and estrogen receptors are implicated in a number of diseases or conditions, such as breast cancer, ovarian cancer, colon cancer, prostate cancer, endometrial cancer, uterine cancer, as well as others diseases or conditions.

SUMMARY OF THE INVENTION

In one aspect, presented herein are compounds of Formula (I), or a pharmaceutically acceptable salt, or N-oxide thereof, that diminish the effects of estrogens with estrogen receptors and/or lower the concentrations of estrogen receptors, and therefore, are useful as agents for the treatment or prevention of diseases or conditions in which the actions of estrogens and/or estrogen receptors are involved in the etiology or pathology of the disease or condition or contribute to at least one symptom of the disease or condition and wherein such actions of estrogens and/or estrogen receptors are undesirable. In some embodiments, compounds disclosed herein are estrogen receptor degrader compounds.

In one aspect, the compound of Formula (I), or a pharmaceutically acceptable salt, or N-oxide thereof, is useful for the treatment of ER-related diseases or conditions including, but not limited to, ER-αdysfunction associated with cancer (e.g. bone cancer, breast cancer, colorectal cancer, endometrial cancer, prostate cancer, ovarian and uterine cancer), leiomyoma (e.g. uterine leiomyoma), central nervous system (CNS) defects (e.g. alcoholism, migraine), cardiovascular system defects (e.g. aortic aneurysm, susceptibility to myocardial infarction, aortic valve sclerosis, cardiovascular disease, coronary artery disease, hypertension), hematological system defects (e.g. deep vein thrombosis), immune and inflammation diseases (e.g. Graves' Disease, arthritis, multiple sclerosis, cirrhosis), susceptibility to infection (e.g. hepatitis B, chronic liver disease), metabolic defects (e.g. bone density, cholestasis, hypospadias, obesity, osteoarthritis, osteopenia, osteoporosis), neurological defects (e.g. Alzheimer's disease, Parkinson's disease, migraine, vertigo), psychiatric defects (e.g. anorexia nervosa, attention deficit hyperactivity disorder (ADHD), dementia, major depressive disorder, psychosis) and reproductive defects (e.g. age of menarche, endometriosis, infertility).

In one aspect, described herein are compounds of Formula (I), pharmaceutically acceptable salts, solvates, N-oxides, metabolites and prodrugs thereof. Compounds of Formula (I) are estrogen receptor modulators. In some embodiments, the compound of Formula (I) is an estrogen receptor antagonist. In some embodiments, the compound of Formula (I) is an estrogen receptor degrader. In some embodiments, the compound of Formula (I) is an estrogen receptor antagonist as well as an estrogen receptor degrader. In some embodiments, the compound of Formula (I) displays minimal or no estrogen receptor agonist activity. In some embodiments, in the context of treating cancers, the compound of Formula (I) offers improved therapeutic activity characterized by complete or longer-lasting tumor regression, a lower incidence or rate of development of resistance to treatment, and/or a reduction in tumor invasiveness.

In one aspect, provided herein is a compound of Formula (I), or a pharmaceutically acceptable salt, or N-oxide thereof:

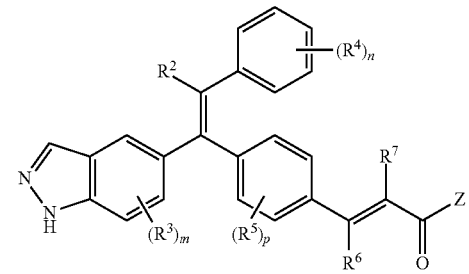

Formula (I)

wherein,

Z is —OH or —OR$^{10}$;

R$^2$ is $C_1$-$C_4$alkyl, $C_1$-$C_4$fluoroalkyl, $C_1$-$C_4$deuteroalkyl, $C_3$-$C_6$cycloalkyl, or —$C_1$-$C_4$alkylene-W;
  W is hydroxy, halogen, CN, $C_1$-$C_4$alkyl, $C_1$-$C_4$haloalkyl, $C_1$-$C_4$alkoxy, $C_1$-$C_4$haloalkoxy, or $C_3$-$C_6$cycloalkyl;

each R$^3$ is independently halogen, $C_1$-$C_4$alkyl, or $C_1$-$C_4$fluoroalkyl;

each R$^4$ is independently halogen, —CN, —OR$^9$, —S(=O)$_2$R$^{10}$, $C_1$-$C_4$alkyl, $C_1$-$C_4$fluoroalkyl, or $C_1$-$C_4$heteroalkyl;

each R$^5$ is independently halogen, —CN, —OR$^9$, —S(=O)$_2$R$^{10}$, $C_1$-$C_4$alkyl, $C_1$-$C_4$fluoroalkyl, or $C_1$-$C_4$heteroalkyl;

R$^6$ is H, $C_1$-$C_4$alkyl, or halogen; R$^7$ is H, $C_1$-$C_4$alkyl, or halogen;

R$^9$ is H, $C_1$-$C_6$alkyl, $C_1$-$C_6$fluoroalkyl, or $C_3$-$C_6$cycloalkyl; R$^{10}$ is $C_1$-$C_6$alkyl;

m is 0, 1, or 2; n is 0, 1, 2, 3, or 4; and p is 0, 1, or 2.

In some embodiments, the compound of Formula (I), or a pharmaceutically acceptable salt thereof, or a pharmaceutically acceptable salt, or N-oxide thereof, has the structure of Formula (II), or a pharmaceutically acceptable salt, or N-oxide thereof.

In some embodiments, the compound of Formula (I), or a pharmaceutically acceptable salt thereof, is a compound described in Table 1, or a pharmaceutically acceptable salt thereof.

Throughout the specification, groups and substituents thereof can be chosen by one skilled in the field to provide stable moieties and compounds.

Compounds disclosed herein are estrogen receptor modulators. In some embodiments, compounds disclosed herein have high specificity for the estrogen receptor and have desirable, tissue-selective pharmacological activities. Desirable, tissue-selective pharmacological activities include, but are not limited to, ER antagonist activity in breast cells and minimal or no ER agonist activity in uterine cells. In some embodiments, compounds disclosed herein are estrogen receptor degraders that display full estrogen receptor antagonist activity with negligible or minimal estrogen receptor agonist activity.

In some embodiments, compounds disclosed herein are estrogen receptor degraders. In some embodiments, compounds disclosed herein are estrogen receptor antagonists. In some embodiments, compounds disclosed herein have minimal or negligible estrogen receptor agonist activity.

In some embodiments, presented herein are compounds selected from active metabolites, tautomers, pharmaceutically acceptable solvates, pharmaceutically acceptable salts or prodrugs of a compound of Formula (I).

Also described are pharmaceutical compositions comprising a therapeutically effective amount of a compound of Formula (I), or a pharmaceutically acceptable salt, or N-oxide thereof. In some embodiments, the pharmaceutical composition also contains at least one pharmaceutically acceptable inactive ingredient. In some embodiments, the pharmaceutical composition is formulated for intravenous injection, subcutaneous injection, oral administration, or topical administration. In some embodiments, the pharmaceutical composition is a tablet, a pill, a capsule, a liquid, a suspension, a gel, a dispersion, a suspension, a solution, an emulsion, an ointment, or a lotion.

In some embodiments, the pharmaceutical composition further comprises one or more additional therapeutically active agents selected from: corticosteroids, anti-emetic agents, analgesics, anti-cancer agents, anti-inflammatories, kinase inhibitors, antibodies, HSP90 inhibitors, histone deacetylase (HDAC) inhibitors, poly ADP-ribose polymerase (PARP) inhibitors, and aromatase inhibitors.

In some embodiments, provided herein is a method comprising administering a compound of Formula (I), or a pharmaceutically acceptable salt, or N-oxide thereof to a human with a diseases or condition that is estrogen sensitive, estrogen receptor meditated or estrogen receptor dependent. In some embodiments, the human is already being administered one or more additional therapeutically active agents other than a compound of Formula (I), or a pharmaceutically acceptable salt, or N-oxide thereof. In some embodiments, the method further comprises administering one or more additional therapeutically active agents other than a compound of Formula (I), or a pharmaceutically acceptable salt, or N-oxide thereof.

In some embodiments, the one or more additional therapeutically active agents other than a compound of Formula (I), or a pharmaceutically acceptable salt, or N-oxide thereof are selected from: corticosteroids, anti-emetic agents, analgesics, anti-cancer agents, anti-inflammatories, kinase inhibitors, antibodies, HSP90 inhibitors, histone deacetylase (HDAC) inhibitors, and aromatase inhibitors.

In some embodiments, the methods further comprise administering to the mammal radiation therapy. In certain embodiments, the compound of the methods is administered prior to or following surgery. In certain embodiments, the methods comprise administering to the mammal at least one additional anti-cancer agent.

In some embodiments, there are provided methods of treating cancer in a mammal comprising administering to the mammal a therapeutically effective amount of a compound of Formula (I), or a pharmaceutically acceptable salt, or N-oxide thereof. In certain embodiments, the cancer is breast cancer, ovarian cancer, endometrial cancer, prostate cancer, uterine cancer, cervical cancer or lung cancer. In certain embodiments, the cancer is breast cancer. In certain embodiments, the cancer is a hormone dependent cancer. In certain embodiments, the cancer is an estrogen receptor dependent cancer. In certain embodiments, the cancer is an estrogen-sensitive cancer. In certain embodiments, the cancer is resistant to anti-hormonal treatment. In certain embodiments, the cancer is an estrogen-sensitive cancer or an estrogen receptor dependent cancer that is resistant to anti-hormonal treatment. In some embodiments, the anti-hormonal treatment includes treatment with at least one agent selected from tamoxifen, fulvestrant, steroidal aromatase inhibitors, and non-steroidal aromatase inhibitors. In some embodiments, the methods further comprise administering to the mammal radiation therapy. In certain embodiments, the compound of the methods is administered prior to or following surgery. In certain embodiments, the methods comprise administering to the mammal at least one additional anti-cancer agent.

In some embodiments, there are provided methods of treating hormone receptor positive metastatic breast cancer in a postmenopausal woman with disease progression following anti-estrogen therapy comprising administering to the woman an estrogen receptor degrading compound of Formula (I), or a pharmaceutically acceptable salt, or N-oxide thereof. In some embodiments, the methods further comprise administering to the mammal radiation therapy. In certain embodiments, the compound of the methods is administered prior to or following surgery. In certain embodiments, the methods comprise administering to the mammal at least one additional anti-cancer agent.

In some embodiments, there are provided methods of treating a hormonal dependent benign or malignant disease of the breast or reproductive tract in a mammal comprising administering to the mammal an effective amount of a compound of Formula (I), a pharmaceutically acceptable salt, or N-oxide thereof. In certain embodiments, the benign or malignant disease is breast cancer. In some embodiments, the methods further comprise administering to the mammal radiation therapy. In certain embodiments, the compound of the methods is administered prior to or following surgery. In certain embodiments, the methods comprise administering to the mammal at least one additional anti-cancer agent.

In some embodiments, a compound of Formula (I), or a pharmaceutically acceptable salt, or N-oxide thereof is used to treat hormone receptor positive metastatic breast cancer in a postmenopausal woman with disease progression following anti-estrogen therapy. In some embodiments, the compound is used to treat a hormonal dependent benign or malignant disease of the breast or reproductive tract in a mammal.

Also provided is a method of reducing ER activation in a mammal comprising administering to the mammal at least one compound having the structure of Formula (I), or a pharmaceutically acceptable salt, or N-oxide thereof. In some embodiments, the method comprises reducing ER activation in breast cells, ovarian cells, colon cells, prostate cells, endometrial cells, or uterine cells in the mammal. In some embodiments, the method of reducing ER activation in the mammal comprises reducing the binding of estrogens to estrogen receptors in the mammal In some embodiments, the method of reducing ER activation in the mammal comprises reducing ER concentrations in the mammal.

In one aspect is the use of a compound of Formula (I), or a pharmaceutically acceptable salt, or N-oxide thereof in the manufacture of a medicament for the treatment of diseases or conditions that are estrogen sensitive, estrogen receptor dependent or estrogen receptor mediated. In some embodiments, the disease or condition is breast cancer, ovarian cancer, colon cancer, prostate cancer, endometrial cancer, or uterine cancer. In some embodiments, the disease or condition is bone cancer, breast cancer, colorectal cancer, endometrial cancer, prostate cancer, ovarian cancer, uterine cancer, cervical cancer, lung cancer, alcoholism, migraine, aortic aneurysm, susceptibility to myocardial infarction, aortic valve sclerosis, cardiovascular disease, coronary artery disease, hypertension, deep vein thrombosis, Graves' Disease, arthritis, multiple sclerosis, cirrhosis, hepatitis B, chronic liver disease, bone density, cholestasis, hypospadias, obesity, osteoarthritis, osteopenia, osteoporosis, Alzheimer's disease, Parkinson's disease, migraine, vertigo, anorexia nervosa, attention deficit hyperactivity disorder (ADHD), dementia, major depressive disorder, psychosis, age of menarche, endometriosis, or infertility in a mammal. In some embodiments, the disease or condition is described herein.

In some cases disclosed herein is the use of a compound of Formula (I), or a pharmaceutically acceptable salt, or N-oxide thereof in the treatment or prevention of diseases or conditions that are estrogen sensitive, estrogen receptor dependent or estrogen receptor mediated. In some embodiments, the disease or condition is described herein.

In any of the embodiments disclosed herein, the mammal is a human.

In some embodiments, compounds provided herein are used to diminish, reduce, or eliminate the activity of estrogen receptors.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Estrogen receptor alpha (ER-α; NR3A1) and estrogen receptor beta (ER-β; NR3A2) are steroid hormone receptors, which are members of the large nuclear receptor superfamily. Nuclear receptors share a common modular structure, which minimally includes a DNA binding domain (DBD) and a ligand binding domain (LBD). Steroid hormone receptors are soluble, intracellular proteins that act as ligand-regulated transcription factors. Vertebrates contain five closely related steroid hormone receptors (estrogen receptor, androgen receptor, progesterone receptor, glucocorticoid receptor, mineralcorticoid receptor), which regulate a wide spectrum of reproductive, metabolic and developmental activities. The activities of ER are controlled by the binding of endogenous estrogens, including 17β-estradiol and estrones.

The ER-α gene is located on 6q25.1 and encodes a 595 AA protein. The ER-β gene resides on chromosome 14q23.3 and produces a 530 AA protein. However, due to alternative splicing and translation start sites, each of these genes can give rise to multiple isoforms. In addition to the DNA binding domain (called C domain) and ligand binding domain (E domain) these receptors contain an N-terminal (A/B) domain, a hinge (D) domain that links the C and E domains, and a C-terminal extension (F domain) (Gronemeyer and Laudet; Protein Profile 2: 1173-1308, 1995). While the C and E domains of ER-α and ER-β are quite conserved (95% and 55% amino acid identity, respectively), conservation of the A/B, D and F domains is poor (below 30% amino acid identity). Both receptors are involved in the regulation and development of the female reproductive tract but also play various roles in the central nervous system, cardiovascular systems and bone metabolism.

The ligand binding pocket of steroid hormone receptors is deeply buried within the ligand binding domain. Upon binding, the ligand becomes part of the hydrophobic core of this domain. Consequently most steroid hormone receptors are instable in the absence of hormone and require assistance from chaperones, such as Hsp90, in order to maintain hormone-binding competency. The interaction with Hsp90 also controls nuclear translocation of these receptors. Ligand-binding stabilizes the receptor and initiates sequential conformational changes that release the chaperones, alter the interactions between the various receptor domains and remodel protein interaction surfaces that allow these receptors to translocate into the nucleus, bind DNA and engage in interactions with chromatin remodeling complexes and the transcriptional machinery. Although ER can interact with Hsp90, this interaction is not required for hormone binding and, dependent on the cellular context, apo-ER can be both cytoplasmic and nuclear. Biophysical studies indicated that DNA binding rather than ligand binding contributes to the stability of the receptor (Greenfield et al., Biochemistry 40: 6646-6652, 2001).

ER can interact with DNA either directly by binding to a specific DNA sequence motif called estrogen response element (ERE) (classical pathway), or indirectly via protein-protein interactions (nonclassical pathway) (Welboren et al., Endocrine-Related Cancer 16: 1073-1089, 2009). In the nonclassical pathway, ER has been shown to tether to other transcription factors including SP-1, AP-1 and NF-κB. These interactions appear to play critical roles in the ability of ER to regulate cell proliferation and differentiation.

Both types of ER DNA interactions can result in gene activation or repression dependent on the transcriptional coregulators that are recruited by the respective ER-ERE complex (Klinge, Steroid 65: 227-251, 2000). The recruitment of coregulators is primarily mediated by two protein interaction surfaces, the AF2 and AF1. AF2 is located in the ER E-domain and its conformation is directly regulated by the ligand (Brzozowski et al., Nature 389: 753-758, 1997). Full agonists appear to promote the recruitment of co-activators, whereas weak agonists and antagonists facilitate the binding of co-repressors. The regulation of protein with the AF 1 is less well understood but can be controlled by serine phosphorylation (Ward and Weigel, Biofactors 35: 528-536, 2009). One of the involved phosphorylation sites (S118) appears to control the transcriptional activity of ER in the presence of antagonists such as tamoxifen, which plays an important role in the treatment of breast cancer. While full agonists appear to arrest ER in certain conformation, weak agonists tend to maintain ER in equilibrium between different conformations, allowing cell-dependent differences in co-regulator repertoires to modulate the activity of ER in a cell-dependent manner (Tamrazi et al., Mol. Endocrinol. 17: 2593-2602, 2003). Interactions of ER with DNA are dynamic and include, but are not limited to, the degradation of ER by the proteasome (Reid et al., Mol Cell 11: 695-707, 2003). The degradation of ER with ligands provides an attractive treatment strategy for disease or conditions that estrogen-sensitive and/or resistant to available anti-hormonal treatments.

ER signaling is crucial for the development and maintenance of female reproductive organs including breasts, ovulation and thickening of the endometrium. ER signaling also has a role in bone mass, lipid metabolism, cancers, etc. About 70% of breast cancers express ER-α (ER-α positive) and are dependent on estrogens for growth and survival. Other cancers also are thought to be dependent on ER-α signaling for growth and survival, such as for example ovarian and endometrial cancers. The ER-α antagonist tamoxifen has been used to treat early and advanced ER-α positive breast cancer in both pre- and post-menopausal women. Fulvestrant (Faslodex™) a steroid-based ER antagonist is used to treat breast cancer in women which has have progressed despite therapy with tamoxifen. Steroidal and non-steroidal aromatase inhibitors are also used to treat cancers in humans. In some embodiments, the steroidal and non-steroidal aromatase inhibitors block the production of estrogen from androstenedione and testosterone in post-menopausal women, thereby blocking ER dependent growth in the cancers. In addition to these anti-hormonal agents, progressive ER positive breast cancer is treated in some cases with a variety of other chemotherapeutics, such as for example, the anthracylines, platins, taxanes. In some cases, ER positive breast cancers that harbor genetic amplication of the ERB-B/HER2 tyrosine kinase receptor are treated with the monoclonal antibody trastuzumab (Herceptin™) or the small molecule pan-ERB-B inhibitor lapatinib. Despite this battery of anti-hormonal, chemotherapeutic and small-molecule and antibody-based targeted therapies, many women with ER-α positive breast develop progressive metastatic disease and are in need of new therapies. Importantly, the majority of ER positive tumors that progress on existing anti-hormonal, as well as and other therapies, are thought to remain dependent on ER-α for growth and survival. Thus, there is a need for new ER-α targeting agents that have activity in the setting of metastatic disease and acquired resistance.

In one aspect, described herein are compounds that are selective estrogen receptor modulators (SERMs). In specific embodiments, the SERMs described herein are selective estrogen receptor degraders (SERDs). In some embodiments, in cell-based assays the compounds described herein result in a reduction in steady state ER-α levels (i.e. ER degradation) and are useful in the treatment of estrogen sensitive diseases or conditions and/or diseases or conditions that have developed resistant to anti-hormonal therapies. In some embodiments, compounds disclosed herein minimize levels of the estrogen receptor in the nucleus.

Given the central role of ER-α in breast cancer development and progression, compounds disclosed herein are useful in the treatment of breast cancer, either alone or in combination with other agent agents that modulate other critical pathways in breast cancer, including but not limited to those that target IGF1R, EGFR, erB-B2 and 3 the PI3K/AKT/mTOR axis, HSP90, PARP or histone deacetylases.

Given the central role of ER-α in breast cancer development and progression, compounds disclosed herein are useful in the treatment of breast cancer, either alone or in combination with other agent used to treat breast cancer, including but not limited to aromatase inhibitors, anthracylines, platins, nitrogen mustard alkylating agents, taxanes. Illustrative agent used to treat breast cancer, include, but are not limited to, paclitaxel, anastrozole, exemestane, cyclophosphamide, epirubicin, fulvestrant, letrozole, gemcitabine, trastuzumab, pegfilgrastim, filgrastim, tamoxifen, docetaxel, toremifene, vinorelbine, capecitabine, ixabepilone, as well as others described herein.

ER-related diseases or conditions (for which the agents disclosed herein are therapeutically relevant) include ER-α dysfunction is also associated with cancer (bone cancer, breast cancer, colorectal cancer, endometrial cancer, prostate cancer, ovarian and uterine cancer), leiomyoma (uterine leiomyoma), central nervous system (CNS) defects (alcoholism, migraine), cardiovascular system defects (aortic aneurysm, susceptibility to myocardial infarction, aortic valve sclerosis, cardiovascular disease, coronary artery disease, hypertension), hematological system defects (deep vein thrombosis), immune and inflammation diseases (Graves' Disease, arthritis, multiple sclerosis, cirrhosis), susceptibility to infection (hepatitis B, chronic liver disease), metabolic defects (bone density, cholestasis, hypospadias, obesity, osteoarthritis, osteopenia, osteoporosis), neurological defects (Alzheimer's disease, Parkinson's disease, migraine, vertigo), psychiatric defects (anorexia nervosa, attention deficit hyperactivity disorder (ADHD), dementia, major depressive disorder, psychosis) and reproductive defects (age of menarche, endometriosis, infertility.

In some embodiments, compounds disclosed herein are used to treat cancer in a mammal. In some embodiments, the cancer is breast cancer, ovarian cancer, endometrial cancer, prostate cancer, uterine cancer, cervical cancer or lung cancer. In some embodiments, the cancer is breast cancer. In some embodiments, the cancer is a hormone dependent cancer. In some embodiments, the cancer is an estrogen receptor dependent cancer. In some embodiments, the cancer is an estrogen-sensitive cancer. In some embodiments, the cancer is resistant to anti-hormonal treatment. In some embodiments, the cancer is an estrogen-sensitive cancer or an estrogen receptor dependent cancer that is resistant to anti-hormonal treatment. In some embodiments, anti-hormonal treatment includes treatment with at least one agent selected from tamoxifen, fulvestrant, steroidal aromatase inhibitors, and non-steroidal aromatase inhibitors-resistant.

In some embodiments, compounds disclosed herein are used to treat hormone receptor positive metastatic breast cancer in a postmenopausal woman with disease progression following anti-estrogen therapy.

In some embodiments, compounds disclosed herein are used to treat a hormonal dependent benign or malignant disease of the breast or reproductive tract in a mammal. In some embodiments, the benign or malignant disease is breast cancer.

In some embodiments, compounds disclosed herein are used to treat cancer in a mammal, wherein the mammal is chemotherapy-naïve.

In some embodiments, compounds disclosed herein are used to treat cancer in a mammal, wherein the mammal is being treated for cancer with at least one anti-cancer agent. In one embodiment, the cancer is a hormone refractory cancer.

In some embodiments, compounds disclosed herein are used in the treatment of endometriosis in a mammal.

In some embodiments, compounds disclosed herein are used in the treatment of leiomyoma in a mammal. In some embodiments, the leiomyoma is an uterine leiomyoma, esophageal leiomyoma, cutaneous leiomyoma or small bowel leiomyoma. In some embodiments, compounds disclosed herein are used in the treatment of fibroids in a mammal (e.g. uterine fibroids).

Compounds

Compounds of Formula (I), including pharmaceutically acceptable salts, prodrugs, active metabolites and pharmaceutically acceptable solvates thereof, are estrogen receptor modulators. In specific embodiments, the compounds described herein are estrogen receptor degraders. In specific embodiments, the compounds described herein are estrogen receptor antagonists. In specific embodiments, the compounds described herein are estrogen receptor degraders and estrogen receptor antagonists with minimal or no estrogen receptor agonist activity.

In some embodiments, compounds disclosed herein are estrogen receptor degraders and estrogen receptor antagonists that exhibit: minimal or no estrogen receptor agonism; and/or anti-proliferative activity against breast cancer, ovarian cancer, endometrial cancer, cervical cancer cell lines; and/or maximal anti-proliferative efficacy against breast cancer, ovarian cancer, endometrial cancer, cervical cell lines in-vitro; and/or minimal agonism in the human endometrial (Ishikawa) cell line; and/or no agonism in the human endometrial (Ishikawa) cell line; and/or minimal or no agonism in the immature rat uterine assay in-vivo; and/or inverse agonism in the immature rat uterine assay in-vivo; and/or anti-tumor activity in breast cancer, ovarian cancer, endometrial cancer, cervical cancer cell lines in xenograft assays in-vivo or other rodent models of these cancers.

In one aspect, provided herein is a compound of Formula (I), or a pharmaceutically acceptable salt, or N-oxide thereof:

Formula (I)

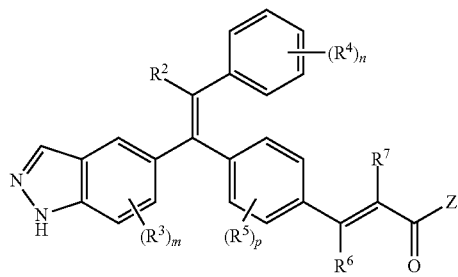

wherein,

Z is —OH or —OR$^{10}$;

R$^2$ is C$_1$-C$_4$alkyl, C$_1$-C$_4$fluoroalkyl, C$_1$-C$_4$deuteroalkyl, C$_3$-C$_6$cycloalkyl, or —C$_1$-C$_4$alkylene-W;
    W is hydroxy, halogen, CN, C$_1$-C$_4$alkyl, C$_1$-C$_4$haloalkyl, C$_1$-C$_4$alkoxy, C$_1$-C$_4$haloalkoxy, or C$_3$-C$_6$cycloalkyl;

each R$^3$ is independently halogen, C$_1$-C$_4$alkyl, or C$_1$-C$_4$fluoroalkyl;

each R$^4$ is independently halogen, —CN, —OR$^9$, —S(=O)$_2$R$^{10}$, C$_1$-C$_4$alkyl, C$_1$-C$_4$fluoroalkyl, or C$_1$-C$_4$heteroalkyl;

each R$^5$ is independently halogen, —CN, —OR$^9$, —S(=O)$_2$R$^{10}$, C$_1$-C$_4$alkyl, C$_1$-C$_4$fluoroalkyl, or C$_1$-C$_4$heteroalkyl;

R$^6$ is H, C$_1$-C$_4$alkyl, or halogen; R$^7$ is H, C$_1$-C$_4$alkyl, or halogen;

R$^9$ is H, C$_1$-C$_6$alkyl, C$_1$-C$_6$fluoroalkyl, or C$_3$-C$_6$cycloalkyl;

R$^{10}$ is C$_1$-C$_6$alkyl;

m is 0, 1, or 2; n is 0, 1, 2, 3, or 4; and p is 0, 1, or 2.

For any and all of the embodiments, substituents are selected from among from a subset of the listed alternatives. For example, in some embodiments, Z is —OH. In some embodiments, Z is —OR$^{10}$. In some embodiments, Z is —OH, —OCH$_3$, or —OCH$_2$CH$_3$.

In some embodiments, R$^6$ is H, —CH$_3$, F, or Cl. In some embodiments, R$^6$ is H.

In some embodiments, R$^7$ is H, —CH$_3$, F, or Cl. In some embodiments, R$^7$ is H.

In some embodiments, R$^9$ is H, C$_1$-C$_6$alkyl, or C$_1$-C$_6$fluoroalkyl. In some embodiments, R$^9$ is H or C$_1$-C$_6$alkyl. In some embodiments, R$^9$ is H.

It is understood that R$^3$ may be present on any open position of the indazole ring system. In some embodiments, each R$^3$ is independently halogen, C$_1$-C$_4$alkyl, or C$_1$-C$_4$fluoroalkyl. In some embodiments, each R$^3$ is independently F, Cl, or —CH$_3$.

In some embodiments, each R$^4$ is independently halogen, —CN, —OH, —OR$^9$, —S(=O)$_2$R$^{10}$, C$_1$-C$_4$alkyl, C$_1$-C$_4$fluoroalkyl, C$_1$-C$_4$heteroalkyl, C$_1$-C$_4$fluoroalkoxy, or C$_1$-C$_4$alkoxy. In some embodiments, each R$^4$ is independently halogen, —CN, —OH, —S(=O)$_2$CH$_3$, —S(=O)$_2$CH$_2$CH$_3$, —CH$_3$, —CH$_2$CH$_3$, —CF$_3$, —CH$_2$OH, —OCF$_3$, —OCH$_3$, or —OCH$_2$CH$_3$. In some embodiments, each R$^4$ is independently F, Cl, —CN, —OH, —CH$_3$, —CH$_2$CH$_3$, —CF$_3$, —CH$_2$OH, —OCF$_3$, —OCH$_3$, or —OCH$_2$CH$_3$. In some embodiments, each R$^4$ is independently F or Cl.

In some embodiments, each R$^5$ is independently halogen, C$_1$-C$_4$alkyl, or C$_1$-C$_4$fluoroalkyl. In some embodiments, each R$^5$ is independently F, Cl, or —CH$_3$.

In some embodiments, m is 0 or 1. In some embodiments, m is 0. In some embodiments, m is 1.

In some embodiments, n is 0, 1, or 2. In some embodiments, n is 0. In some embodiments, n is 1. In some embodiments, n is 2.

In some embodiments, p is 0 or 1. In some embodiments, p is 0. In some embodiments, p is 1.

In some embodiments, m is 0; and p is 0.

In some embodiments, Z is —OH; R$^6$ is H, —CH$_3$, F, or Cl; R$^7$ is H, —CH$_3$, F, or Cl; each R$^3$ is independently halogen, C$_1$-C$_4$alkyl, or C$_1$-C$_4$fluoroalkyl; each R$^4$ is independently halogen, —CN, —OH, —OR$^9$, —S(=O)$_2$R$^{10}$, C$_1$-C$_4$alkyl, C$_1$-C$_4$fluoroalkyl, C$_1$-C$_4$heteroalkyl, C$_1$-C$_4$-fluoroalkoxy, or C$_1$-C$_4$alkoxy; each R$^5$ is independently halogen, C$_1$-C$_4$alkyl, or C$_1$-C$_4$fluoroalkyl; m is 0 or 1; n is 0, 1, or 2; and p is 0 or 1.

In some embodiments, R$^2$ is C$_1$-C$_4$alkyl, C$_1$-C$_4$fluoroalkyl, C$_1$-C$_4$deuteroalkyl, C$_3$-C$_6$cycloalkyl, or —C$_1$-C$_4$alkylene-W; W is hydroxy, halogen, CN, C$_1$-C$_4$alkoxy, or C$_3$-C$_6$cycloalkyl. In some embodiments, R$^2$ is C$_1$-C$_4$alkyl, C$_1$-C$_4$fluoroalkyl, or C$_1$-C$_4$deuteroalkyl. In some embodiments, R$^2$ is C$_1$-C$_4$alkyl. In some embodiments, R$^2$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH$_2$F, —CHF$_2$, —CF$_3$, —CH$_2$CF$_3$, —CD$_3$, —CH$_2$CD$_3$, —CD$_2$CD$_3$, cyclopropyl, cyclobutyl, cyclopentyl, cyclohexyl, —CH$_2$—W, or —CH$_2$CH$_2$—W; W is hydroxy, F, Cl, —CN, —OCH$_3$, —OCH$_2$CH$_3$, —OCH$_2$CH$_2$CH$_3$, —OCH(CH$_3$)$_2$, cyclopropyl, cyclobutyl, cyclopentyl, or cyclohexyl. In some embodiments, W is hydroxy, F, Cl, —CN, cyclopropyl, cyclobutyl, cyclopentyl, or cyclohexyl. In some embodiments, R$^2$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH$_2$F, —CHF$_2$, —CF$_3$, —CH$_2$CF$_3$, —CD$_3$, —CH$_2$CD$_3$, —CD$_2$CD$_3$, —CH$_2$—W, or —CH$_2$CH$_2$—W. In some embodiments, R$^2$ is —CH$_3$, —CH$_2$CH$_3$, —CH$_2$F, —CHF$_2$, —CF$_3$, —CH$_2$CF$_3$, —CD$_3$, —CD$_2$CD$_3$, —CH$_2$CD$_3$, cyclopropyl or cyclobutyl. In some embodiments, R$^2$ is —CH$_2$CH$_3$, —CH$_2$CF$_3$, —CD$_2$CD$_3$, or —CH$_2$CD$_3$. In some embodiments, R$^2$ is —CH$_2$CH$_3$, —CD$_2$CD$_3$, or —CH$_2$CD$_3$. In some embodiments, R$^2$ is —CH$_2$CH$_3$ or cyclobutyl. In some embodiments, R$^2$ is —CH$_2$CH$_3$.

In some embodiments, each R$^3$ is independently F, Cl, or —CH$_3$; and m is 0 or 1.

In some embodiments, Z is —OH; R$^6$ is H; R$^7$ is H; m is 0; n is 0, 1, or 2; and p is 0.

In some embodiments, the compound of Formula (I) has the structure of Formula (II), or a pharmaceutically acceptable salt, or N-oxide thereof:

Formula (II)

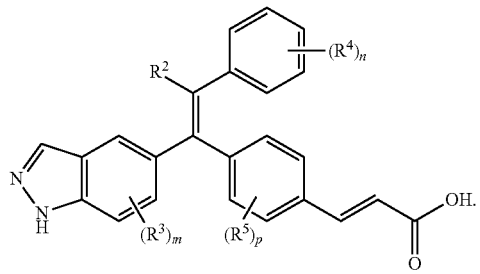

In some embodiments, each R$^3$ is independently F, Cl, or —CH$_3$; each R$^4$ is independently halogen, —CN, —OH, —S(=O)$_2$CH$_3$, —S(=O)$_2$CH$_2$CH$_3$, —CH$_3$, —CH$_2$CH$_3$, —CF$_3$, —CH$_2$OH, —OCF$_3$, —OCH$_3$, or —OCH$_2$CH$_3$; each R$^5$ is independently F, Cl, or —CH$_3$; m is 0 or 1; n is 0, 1, or 2; and p is 0 or 1.

In some embodiments, R$^2$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH$_2$F, —CHF$_2$, —CF$_3$, —CH$_2$CF$_3$, —CD$_3$, —CD$_2$CD$_3$, cyclopropyl, cyclobutyl, cyclopentyl, cyclohexyl, —CH$_2$—W, or —CH$_2$CH$_2$—W; W is hydroxy, F, Cl, —CN, —OCH$_3$, —OCH$_2$CH$_3$, —OCH$_2$CH$_2$CH$_3$, —OCH(CH$_3$)$_2$, cyclopropyl, cyclobutyl, cyclopentyl, or cyclohexyl.

In some embodiments, W is hydroxy, F, Cl, —CN, cyclopropyl, cyclobutyl, cyclopentyl, or cyclohexyl; each R$^4$ is independently F, Cl, —CN, —OH, —CH$_3$, —CF$_3$, —OCF$_3$, or —OCH$_3$; m is 0 or 1; n is 0, 1, or 2; and p is 0.

In some embodiments, R$^2$ is —CH$_2$CH$_3$ or cyclobutyl; each R$^4$ is independently F, Cl, —CN, —OH, —CH$_3$, —CH$_2$CH$_3$, —CF$_3$, —CH$_2$OH, —OCF$_3$, —OCH$_3$, or —OCH$_2$CH$_3$; m is 0 or 1; n is 0, 1, or 2; and p is 0. In some embodiments, R$^2$ is —CH$_2$CH$_3$; each R$^4$ is independently F, Cl, —CN, —OH, —CH$_3$, —CH$_2$CH$_3$, —CF$_3$, —CH$_2$OH, —OCF$_3$, —OCH$_3$, or —OCH$_2$CH$_3$; m is 0; n is 0, 1, or 2; and p is 0.

In some embodiments, the compound of Formula (I) or Formula (II) has the following structure, or a pharmaceutically acceptable salt thereof, or N-oxide thereof:

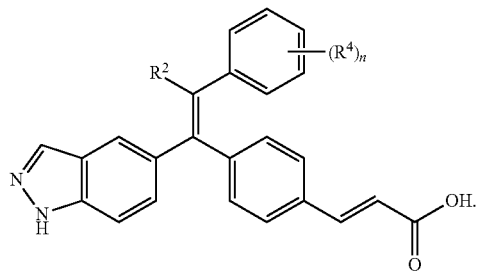

In some embodiments,

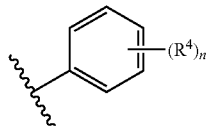

is phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 2-bromophenyl, 3-bromophenyl, 4-bromophenyl, 2-methylphenyl, 3-methylphenyl, 4-methylphenyl, 2-ethylphenyl, 3-ethylphenyl, 4-ethylphenyl, 2-methoxyphenyl, 3-methoxyphenyl, 4-methoxyphenyl, 2-ethoxyphenyl, 3-ethoxyphenyl, 4-ethoxyphenyl, 2-trifluoromethylphenyl, 3-trifluoromethylphenyl, 4-trifluoromethylphenyl, 2-fluoro-4-methoxyphenyl, 2-cyanophenyl, 3-cyanophenyl, 4-cyanophenyl, 2-fluoro-3-chlorophenyl, 2-fluoro-4-chlorophenyl, 2-fluoro-5-chlorophenyl, 2-fluoro-6-chlorophenyl, 2-chloro-3-fluorophenyl, 2-chloro-4-fluorophenyl, 2-chloro-5-fluorophenyl, 2-chloro-6-fluorophenyl, 2-methyl-3-chlorophenyl, 2-methyl-4-chlorophenyl, 2-methyl-5-chlorophenyl, 2-methyl-6-chlorophenyl, 2-methyl-3-fluorophenyl, 2-methyl-4-fluorophenyl, 2-methyl-5-fluorophenyl, 2-methyl-6-fluorophenyl, 3-methyl-4-fluorophenyl, 2-trifluoromethyl-3-chlorophenyl, 2-trifluoromethyl-4-chlorophenyl, 2-trifluoromethyl-5-chlorophenyl, 2-trifluoromethyl-6-chlorophenyl, 2-hydroxyphenyl, 3-hydroxyphenyl, 4-hydroxyphenyl, 2-hydroxymethylphenyl, 3-hydroxymethylphenyl, 4-hydroxymethylphenyl, 2-methylsulfonylphenyl, 3-methylsulfonylphenyl, or 4-methyl sulfonylphenyl.

In some embodiments,

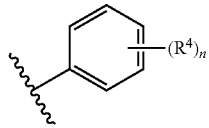

is phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 2-methylphenyl, 3-methylphenyl, 4-methylphenyl, 2-trifluoromethylphenyl, 3-trifluoromethylphenyl, 4-trifluoromethylphenyl, 2-fluoro-4-methoxyphenyl, 2-fluoro-3-chlorophenyl, 2-fluoro-4-chlorophenyl, 2-fluoro-5-chlorophenyl, 2-fluoro-6-chlorophenyl, 2-chloro-3-fluorophenyl, 2-chloro-4-fluorophenyl, 2-chloro-5-fluorophenyl, 2-chloro-6-fluorophenyl, 2-methyl-3-chlorophenyl, 2-methyl-4-chlorophenyl, 2-methyl-5-chlorophenyl, 2-methyl-6-chlorophenyl, 2-methyl-3-fluorophenyl, 2-methyl-4-fluorophenyl, 2-methyl-5-fluorophenyl, 2-methyl-6-fluorophenyl, 3-methyl-4-fluorophenyl, 2-trifluoromethyl-3-chlorophenyl, 2-trifluoromethyl-4-chlorophenyl, 2-trifluoromethyl-5-chlorophenyl, or 2-trifluoromethyl-6-chlorophenyl.

Any combination of the groups described above for the various variables is contemplated herein. Throughout the specification, groups and substituents thereof are chosen by one skilled in the field to provide stable moieties and compounds.

In some embodiments, the compound of Formula (I), is a compound presented in Table 1, or a pharmaceutically acceptable salt, or N-oxide thereof:

TABLE 1

| Compound Name | | Structure | LCMS* [M + H]+ |
|---|---|---|---|
| 1 | (E)-Ethyl 3-(4-((E)-1-(1H-indazol-5-yl)-2-phenylbut-1-en-1-yl)phenyl)acrylate | 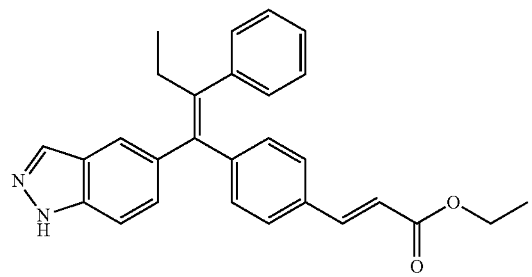 | 423 |
| 2 | (E)-3-(4-((E)-1-(1H-Indazol-5-yl)-2-phenylbut-1-en-1-yl)phenyl)acrylic acid | 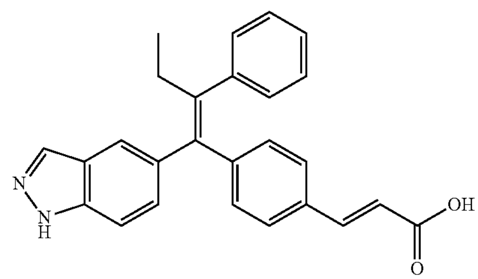 | 395 |
| 3 | (E)-3-(4-((E)-2-(4-Fluorophenyl)-1-(1H-indazol-5-yl)but-1-en-1-yl)phenyl)acrylic acid | 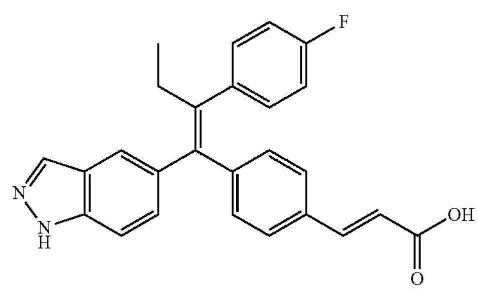 | 413 |
| 4 | (E)-3-(4-((E)-2-(4-Chlorophenyl)-1-(1H-indazol-5-yl)but-1-en-1-yl)phenyl)acrylic acid | 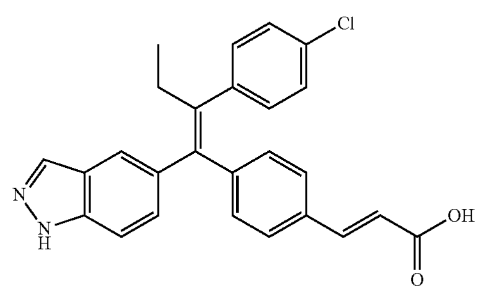 | 429 |
| 5 | (E)-3-(4-((E)-1-(1H-Indazol-5-yl)-2-(3-methoxyphenyl)but-1-en-1-yl)phenyl)acrylic acid | 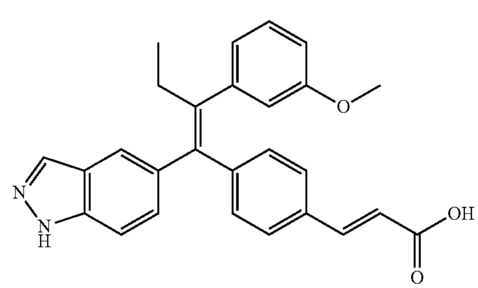 | 425 |

TABLE 1-continued

| Compound Name | | Structure | LCMS* [M + H]+ |
|---|---|---|---|
| 6 | (E)-3-(4-((E)-2-(3-(Hydroxymethyl)phenyl)-1-(1H-indazol-5-yl)but-1-en-1-yl)phenyl)acrylic acid | 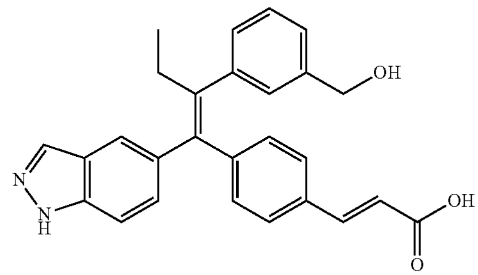 | 425 |
| 7 | (E)-3-(4-((E)-2-(4-(Hydroxymethyl)phenyl)-1-(1H-indazol-5-yl)but-1-en-1-yl)phenyl)acrylic acid | 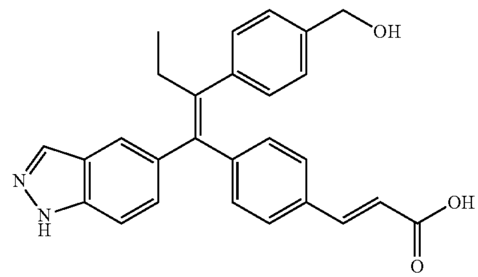 | 425 |
| 8 | (E)-3-(4-((E)-2-(2-(Hydroxymethyl)phenyl)-1-(1H-indazol-5-yl)but-1-en-1-yl)phenyl)acrylic acid | 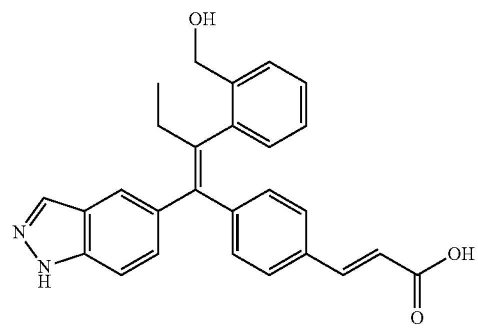 | 425 |
| 9 | (E)-3-(4-((E)-1-(1H-Indazol-5-yl)-2-(o-tolyl)but-1-en-1-yl)phenyl)acrylic acid | 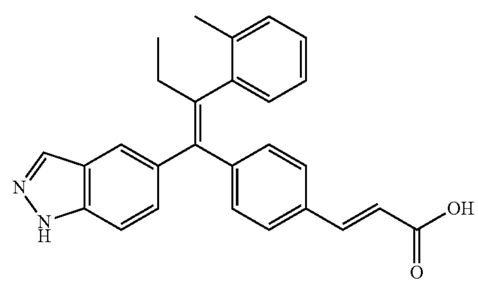 | 409 |
| 10 | (E)-3-(4-((E)-1-(1H-Indazol-5-yl)-2-(m-tolyl)but-1-en-1-yl)phenyl)acrylic acid | 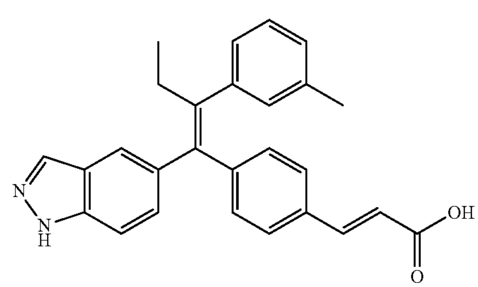 | 409 |

TABLE 1-continued

| Compound Name | | Structure | LCMS* [M + H]+ |
|---|---|---|---|
| 11 | (E)-3-(4-((E)-1-(1H-Indazol-5-yl)-2-(p-tolyl)but-1-en-1-yl)phenyl)acrylic acid | 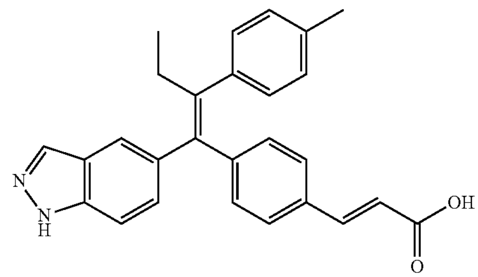 | 409 |
| 12 | (E)-3-(4-((E)-1-(1H-Indazol-5-yl)-2-(2-methoxyphenyl)but-1-en-1-yl)phenyl)acrylic acid | 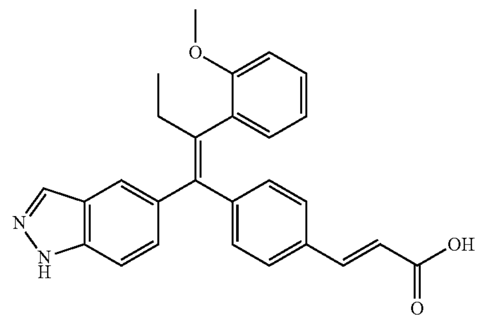 | 425 |
| 13 | (E)-3-(4-((E)-1-(1H-Indazol-5-yl)-2-(4-methoxyphenyl)but-1-en-1-yl)phenyl)acrylic acid | 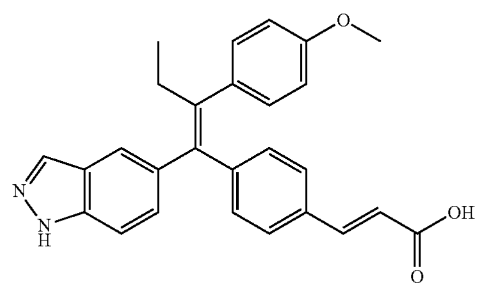 | 425 |
| 14 | ((E)-3-(4-((E)-2-(2-Chlorophenyl)-1-(1H-indazol-5-yl)but-1-en-1-yl)phenyl)acrylic acid | 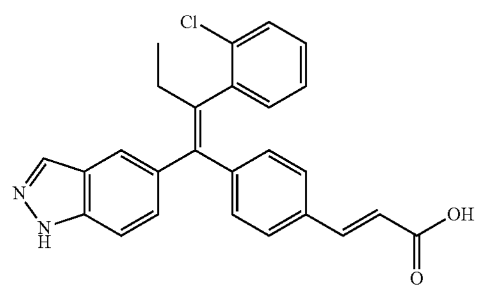 | 429 |
| 15 | (E)-3-(4-((E)-2-(3-Chlorophenyl)-1-(1H-indazol-5-yl)but-1-en-1-yl)phenyl)acrylic acid | 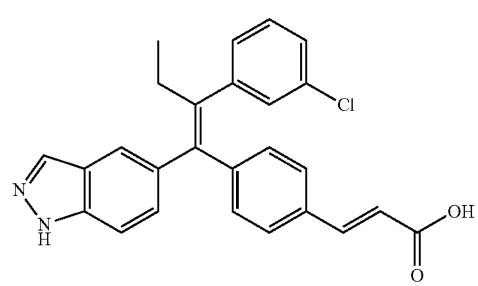 | 429 |

TABLE 1-continued

| Compound Name | | Structure | LCMS* [M + H]+ |
|---|---|---|---|
| 16 | (E)-3-(4-((E)-2-(2-Fluorophenyl)-1-(1H-indazol-5-yl)but-1-en-1-yl)phenyl)acrylic acid | 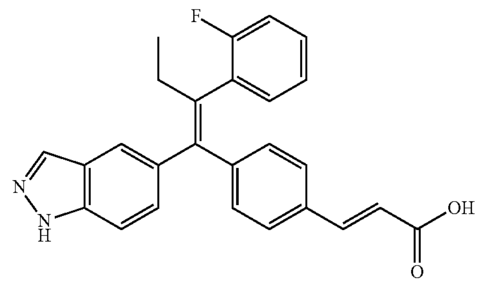 | 413 |
| 17 | (E)-3-(4-((E)-2-(3-Fluorophenyl)-1-(1H-indazol-5-yl)but-1-en-1-yl)phenyl)acrylic acid | 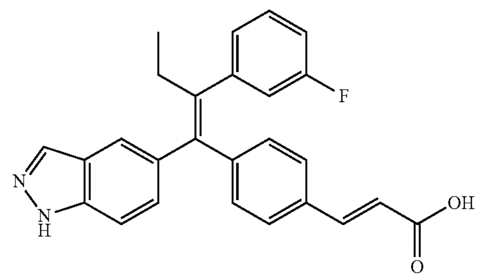 | 413 |
| 18 | (E)-3-(4-((E)-2-(2-Ethylphenyl)-1-(1H-indazol-5-yl)but-1-en-1-yl)phenyl)acrylic acid | 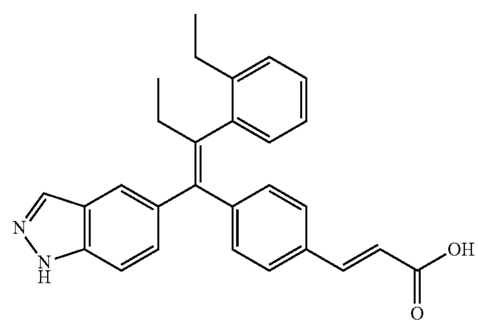 | 423 |
| 19 | (E)-3-(4-((E)-1-(1H-Indazol-5-yl)-2-(2-(trifluoromethyl)phenyl)but-1-en-1-yl)phenyl)acrylic acid | 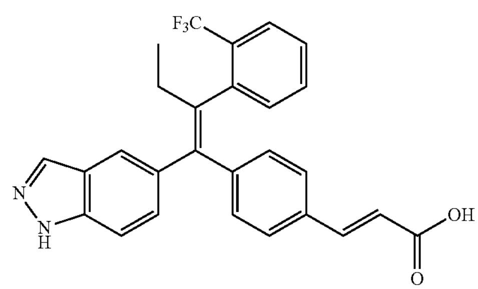 | 463 |
| 20 | (E)-3-(4-((E)-4-Chloro-1-(1H-indazol-5-yl)-2-phenylbut-1-en-1-yl)phenyl)acrylic acid | 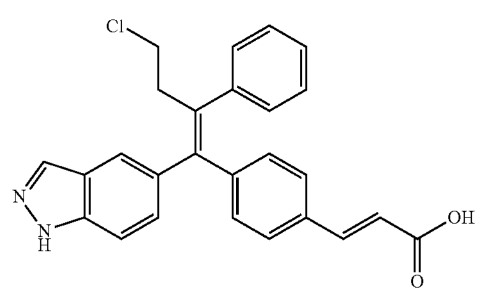 | 429 |

TABLE 1-continued

| Compound | Name | Structure | LCMS* [M + H]+ |
|---|---|---|---|
| 21 | (E)-3-(4-((E)-2-(2-Cyanophenyl)-1-(1H-indazol-5-yl)but-1-en-1-yl)phenyl)acrylic acid | 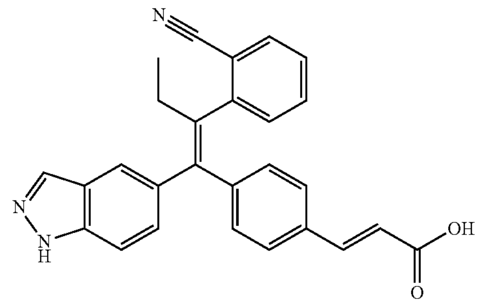 | 420 |
| 22 | (E)-3-(4-((E)-2-(2,4-Difluorophenyl)-1-(1H-indazol-5-yl)but-1-en-1-yl)phenyl)acrylic acid | 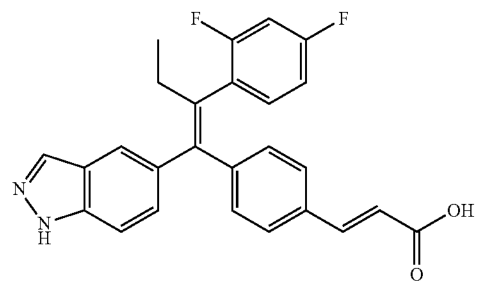 | 431 |
| 23 | (E)-3-(4-((E)-2-(2-Chloro-3-fluorophenyl)-1-(1H-indazol-5-yl)but-1-en-1-yl)phenyl)acrylic acid | 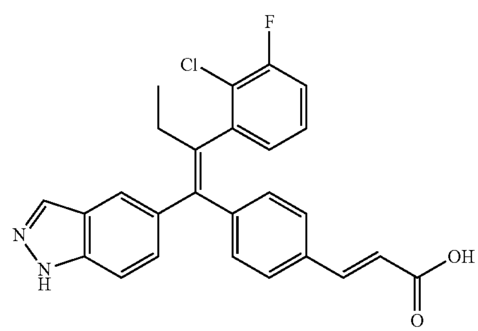 | 447 |
| 24 | (E)-3-(4-((E)-2-Cyclopropyl-1-(1H-indazol-5-yl)-2-phenylvinyl)phenyl)acrylic acid | 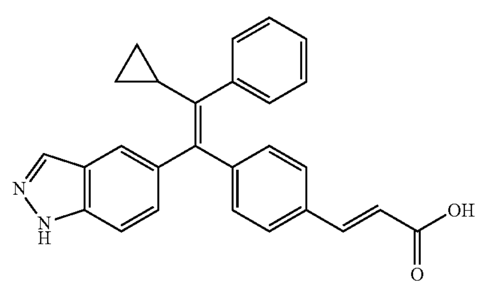 | 407 |
| 25 | (E)-3-(4-((E)-2-(4-Fluoro-2-methylphenyl)-1-(1H-indazol-5-yl)but-1-en-1-yl)phenyl)acrylic acid | 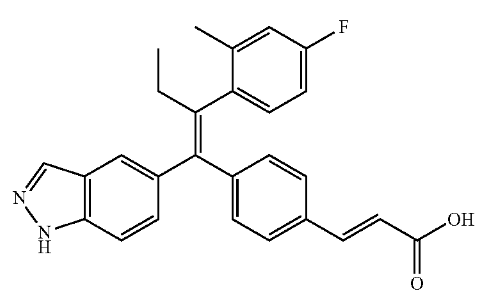 | 427 |

TABLE 1-continued

| Compound Name | | Structure | LCMS* [M + H]+ |
|---|---|---|---|
| 26 | (E)-3-(4-((E)-2-(2,6-Difluorophenyl)-1-(1H-indazol-5-yl)but-1-en-1-yl)phenyl)acrylic acid | 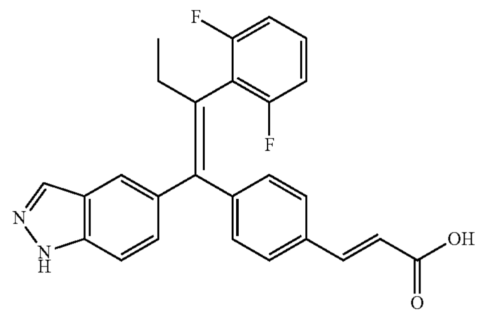 | 431 |
| 27 | (E)-3-(4-((E)-2-(2,6-Dichlorophenyl)-1-(1H-indazol-5-yl)but-1-en-1-yl)phenyl)acrylic acid | 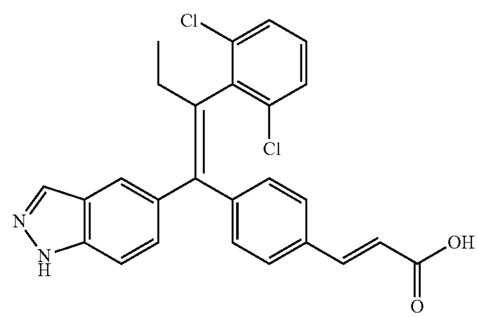 | 463 |
| 28 | (E)-3-(4-((E)-4,4,4-Trideutero-1-(1H-indazol-5-yl)-2-phenylbut-1-en-1-yl)phenyl)acrylic acid | 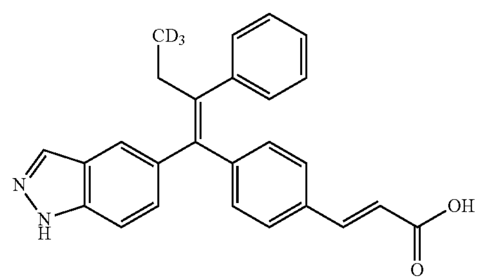 | 398 |
| 29 | (E)-3-(4-((E)-2-(4-Fluoro-3-methylphenyl)-1-(1H-indazol-5-yl)but-1-en-1-yl)phenyl)acrylic acid | 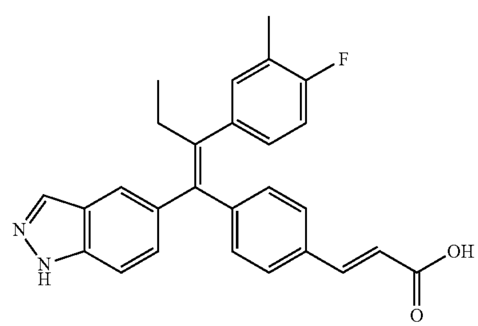 | 427 |
| 30 | (E)-3-(4-((E)-2-(5-Fluoro-2-methylphenyl)-1-(1H-indazol-5-yl)but-1-en-1-yl)phenyl)acrylic acid | 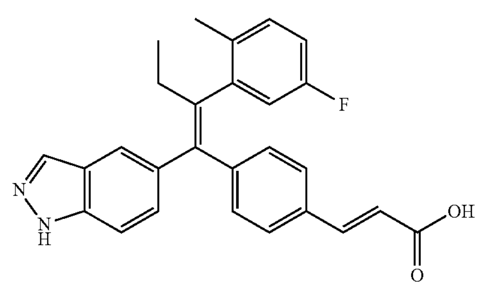 | 427 |

TABLE 1-continued

| Compound | Name | Structure | LCMS* [M + H]+ |
|---|---|---|---|
| 31 | (E)-3-(4-((E)-2-(2,3-Difluorophenyl)-1-(1H-indazol-5-yl)but-1-en-1-yl)phenyl)acrylic acid | 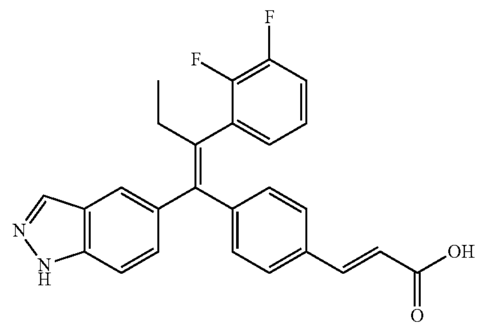 | 431 |
| 32 | (E)-3-(4-((E)-2-(2,5-Difluorophenyl)-1-(1H-indazol-5-yl)but-1-en-1-yl)phenyl)acrylic acid | 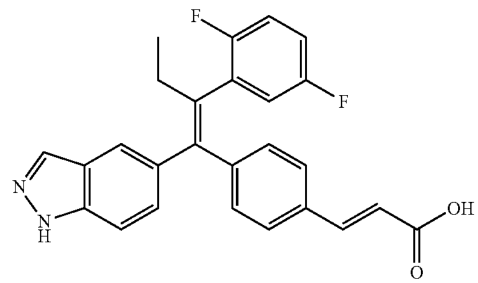 | 431 |
| 33 | (E)-3-(4-((E)-2-(2-Chloro-5-fluorophenyl)-1-(1H-indazol-5-yl)but-1-en-1-yl)phenyl)acrylic acid | 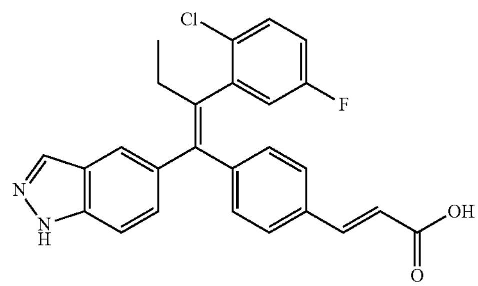 | 447 |
| 34 | (E)-3-(4-((E)-2-(2-Chloro-6-methylphenyl)-1-(1H-indazol-5-yl)but-1-en-1-yl)phenyl)acrylic acid | 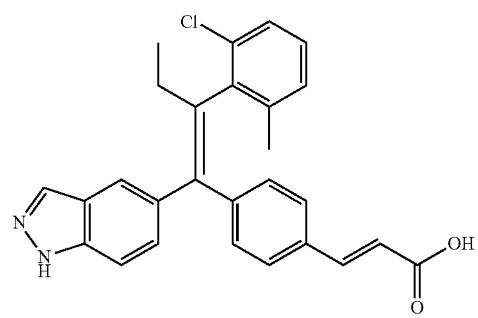 | 443 |
| 35 | (E)-3-(4-((E)-1-(7-Chloro-1H-indazol-5-yl)-2-phenylbut-1-en-1-yl)phenyl)acrylic acid | 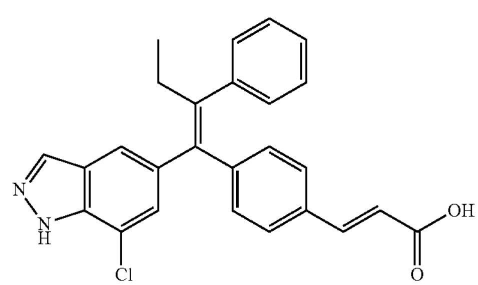 | 429 |

TABLE 1-continued

| Compound Name | | Structure | LCMS* [M + H]+ |
|---|---|---|---|
| 36 | (E)-3-(4-((E)-1-(4-Methyl-1H-indazol-5-yl)-2-phenylbut-1-en-1-yl)phenyl)acrylic acid | 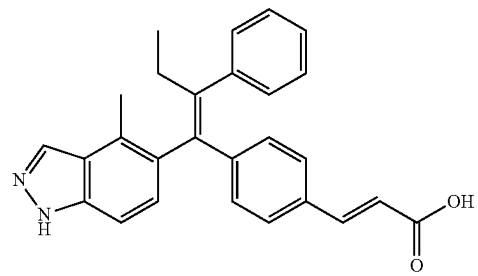 | 409 |
| 37 | (E)-3-(4-((E)-1-(7-Methyl-1H-indazol-5-yl)-2-phenylbut-1-en-1-yl)phenyl)acrylic acid | 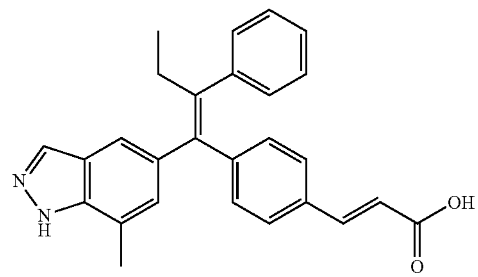 | 409 |
| 38 | (E)-3-(4-((E)-1-(6-Methyl-1H-indazol-5-yl)-2-phenylbut-1-en-1-yl)phenyl)acrylic acid | 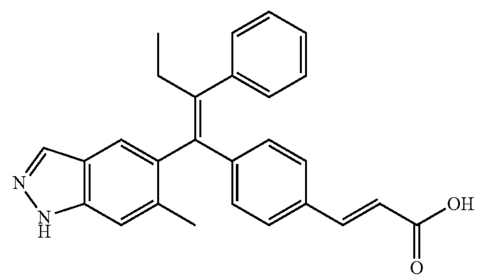 | 409 |
| 39 | (E)-3-(4-((E)-1-(3-Methyl-1H-indazol-5-yl)-2-phenylbut-1-en-1-yl)phenyl)acrylic acid | 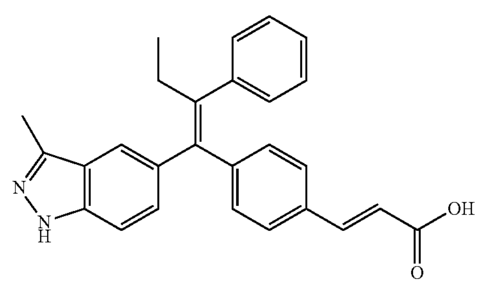 | 409 |
| 40 | (E)-3-(4-((E)-1-(3-Chloro-1H-indazol-5-yl)-2-phenylbut-1-en-1-yl)phenyl)acrylic acid | 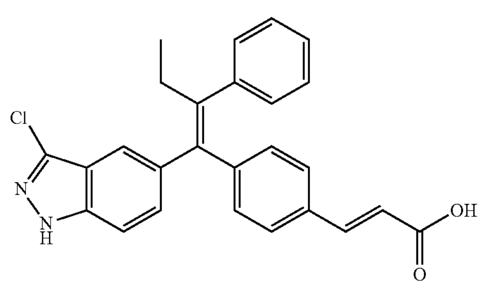 | 429 |

TABLE 1-continued

| Compound Name | | Structure | LCMS* [M + H]+ |
|---|---|---|---|
| 41 | (E)-3-(4-((E)-2-(4-Chloro-2-methylphenyl)-1-(1H-indazol-5-yl)but-1-en-1-yl)phenyl)acrylic acid | 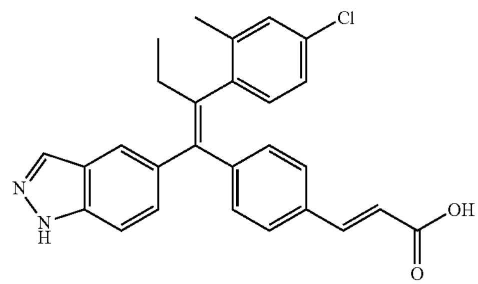 | 443 |
| 42 | (E)-3-(4-((E)-1-(1H-Indazol-5-yl)-2-phenylprop-1-en-1-yl)phenyl)acrylic acid | 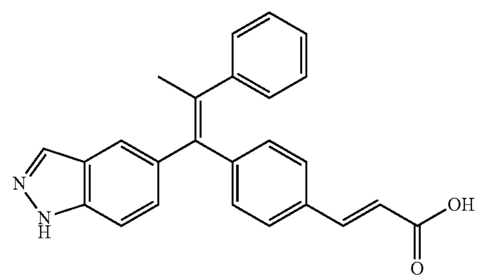 | 381 |
| 43 | (E)-3-(4-((E)-1-(1H-Indazol-5-yl)-2-phenylpent-1-en-1-yl)phenyl)acrylic acid | 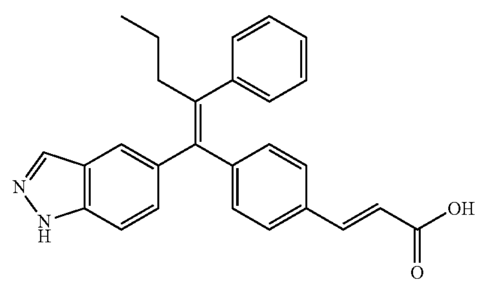 | 409 |
| 44 | (E)-3-(4-((E)-2-(3-Cyanophenyl)-1-(1H-indazol-5-yl)but-1-en-1-yl)phenyl)acrylic acid | 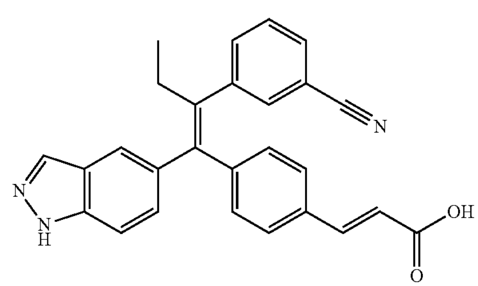 | 420 |
| 45 | (E)-3-(4-((E)-2-(4-Cyanophenyl)-1-(1H-indazol-5-yl)but-1-en-1-yl)phenyl)acrylic acid | 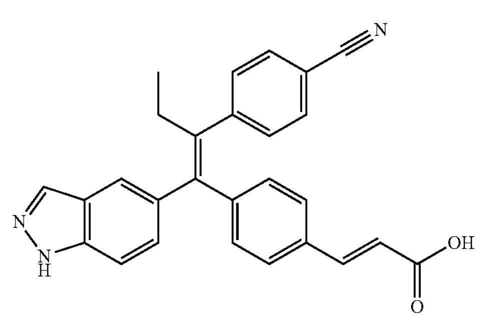 | 420 |

TABLE 1-continued

| Compound Name | | Structure | LCMS* [M + H]+ |
|---|---|---|---|
| 46 | (E)-3-(4-((E)-4-Hydroxy-1-(1H-indazol-5-yl)-2-phenylbut-1-en-1-yl)phenyl)acrylic acid | 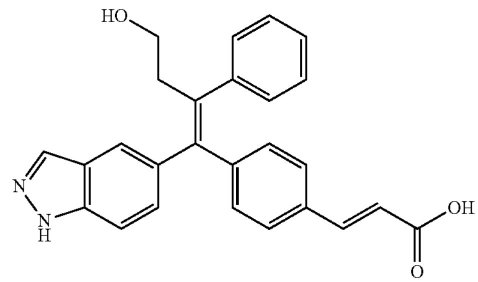 | 411 |
| 47 | (E)-3-(4-((E)-1-(1H-Indazol-5-yl)-4-methoxy-2-phenylbut-1-en-1-yl)phenyl)acrylic acid | 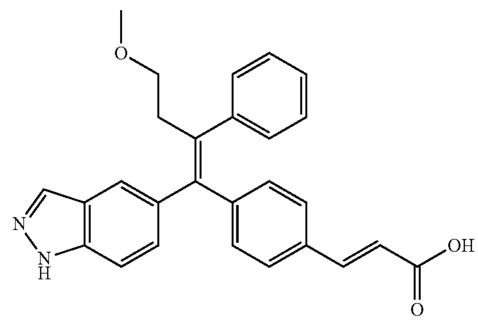 | 425 |
| 48 | (E)-3-(4-((Z)-1-(1H-Indazol-5-yl)-3-methoxy-2-phenylprop-1-en-1-yl)phenyl)acrylic acid | 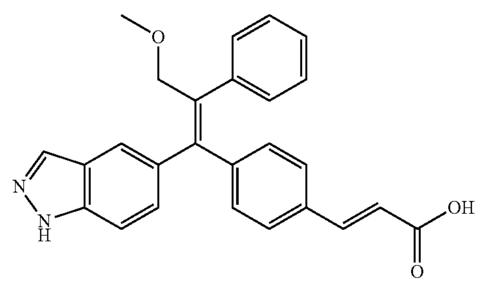 | 411 |
| 49 | (E)-3-(4-((E)-1-(4-Fluoro-1H-indazol-5-yl)-2-phenylbut-1-en-1-yl)phenyl)acrylic acid | 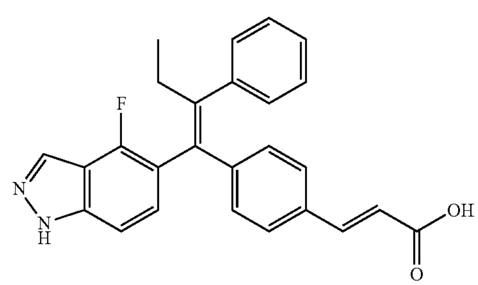 | 413 |
| 50 | (E)-3-(4-((E)-1-(6-Chloro-1H-indazol-5-yl)-2-phenylbut-1-en-1-yl)phenyl)acrylic acid | 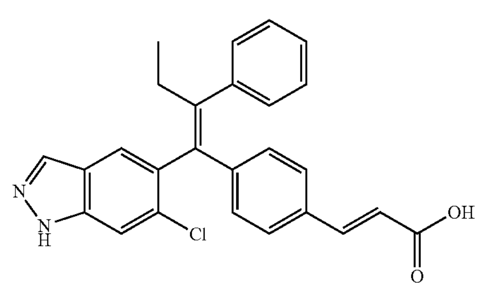 | 429 |

TABLE 1-continued

| Compound Name | Structure | LCMS* [M + H]+ |
|---|---|---|
| 51 (E)-3-(4-((E)-1-(1H-Indazol-5-yl)-4-methyl-2-phenylpent-1-en-1-yl)phenyl)acrylic acid | | 423 |
| 52 (E)-3-(4-((E)-1-(4-Chloro-1H-indazol-5-yl)-2-phenylbut-1-en-1-yl)phenyl)acrylic acid | | 429 |
| 53 (E)-3-(4-((E)-2-Cyclopentyl-1-(1H-indazol-5-yl)-2-phenylvinyl)phenyl)acrylic acid | | 435 |
| 54 (E)-3-(4-((E)-2-Cyclohexyl-1-(1H-indazol-5-yl)-2-phenylvinyl)phenyl)acrylic acid | | 449 |
| 55 (E)-3-(4-((E)-1-(1H-Indazol-5-yl)-3-methyl-2-phenylbut-1-en-1-yl)phenyl)acrylic acid | | 409 |

TABLE 1-continued

| Compound Name | | Structure | LCMS* [M + H]+ |
|---|---|---|---|
| 56 | (E)-3-(4-((E)-3-Cyclopropyl-1-(1H-indazol-5-yl)-2-phenylprop-1-en-1-yl)phenyl)acrylic acid | 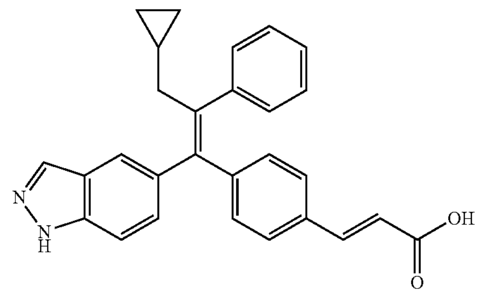 | 421 |
| 57 | (E)-3-(4-((E)-2-(2-Chlorophenyl)-2-cyclopropyl-1-(1H-indazol-5-yl)vinyl)phenyl)acrylic acid | 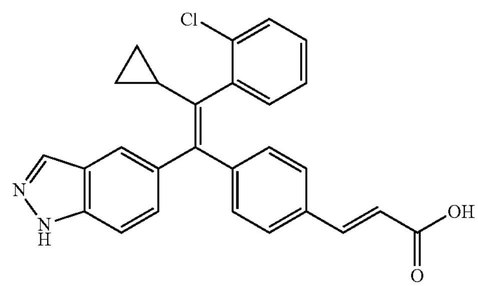 | 441 |
| 58 | (E)-3-(4-((E)-1-(6-Fluoro-1H-indazol-5-yl)-2-phenylbut-1-en-1-yl)phenyl)acrylic acid | 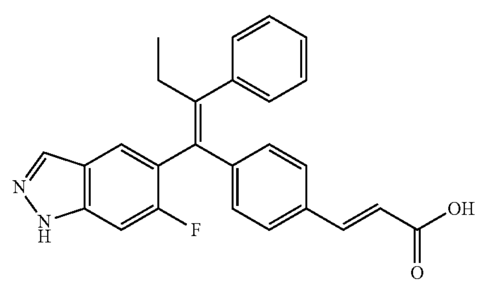 | 413 |
| 59 | (E)-3-(4-((E)-1-(1H-Indazol-5-yl)-2-phenylhex-1-en-1-yl)phenyl)acrylic acid | 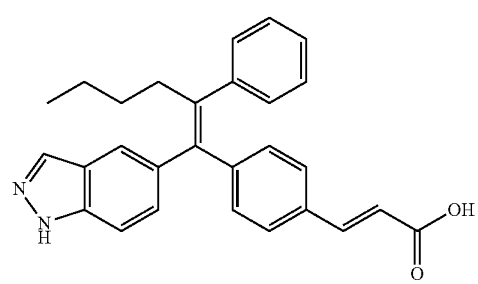 | 423 |
| 60 | (E)-3-(4-((E)-3-Cyclopentyl-1-(1H-indazol-5-yl)-2-phenylprop-1-en-1-yl)phenyl)acrylic acid | 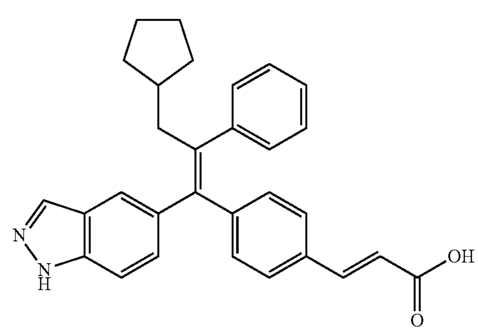 | 449 |

TABLE 1-continued

| Compound Name | | Structure | LCMS* [M + H]+ |
|---|---|---|---|
| 61 | (E)-3-(4-((E)-2-(2-Chloro-4-fluorophenyl)-1-(4-fluoro-1H-indazol-5-yl)but-1-en-1-yl)phenyl)acrylic acid | 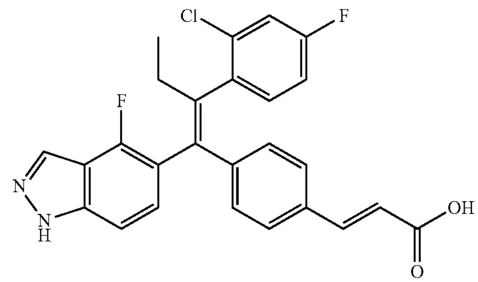 | 465 |
| 62 | (E)-3-(4-((E)-1-(7-Fluoro-1H-indazol-5-yl)-2-phenylbut-1-en-1-yl)phenyl)acrylic acid | 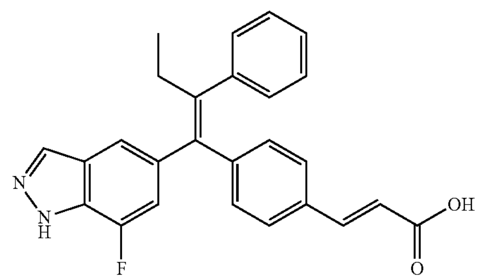 | 413 |
| 63 | (E)-3-(4-((E)-2-(2-Chloro-4-fluorophenyl)-1-(1H-indazol-5-yl)-4-methylpent-1-en-1-yl)phenyl)acrylic acid | 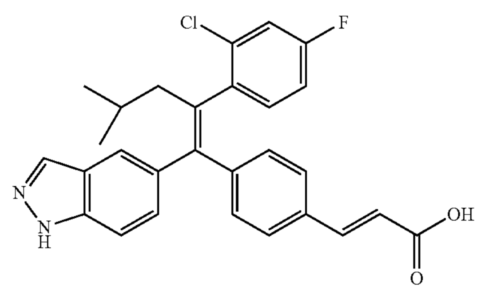 | 475 |
| 64 | (E)-3-(4-((Z)-3,3-Difluoro-1-(1H-indazol-5-yl)-2-phenylprop-1-en-1-yl)phenyl)acrylic acid | 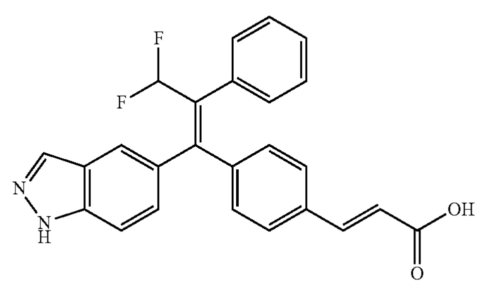 | 417 |
| 65 | (E)-3-(4-((E)-2-(2-Chloro-4-fluorophenyl)-1-(7-fluoro-1H-indazol-5-yl)but-1-en-1-yl)phenyl)acrylic acid | 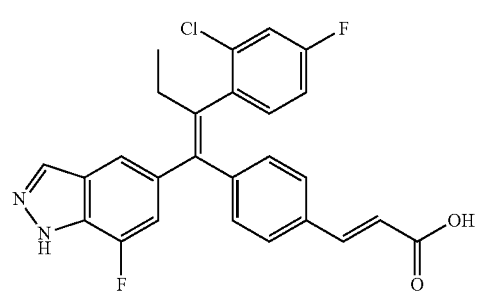 | 465 |

TABLE 1-continued

| Compound | Name | Structure | LCMS* [M + H]+ |
|---|---|---|---|
| 66 | (E)-3-(4-((E)-4-Fluoro-1-(1H-indazol-5-yl)-2-phenylbut-1-en-1-yl)phenyl)acrylic acid | 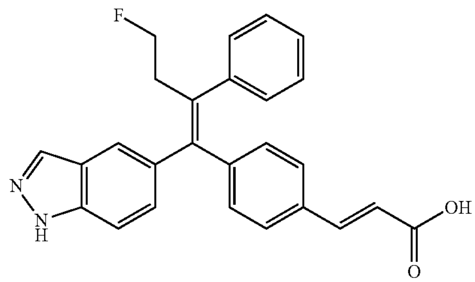 | 413 |
| 67 | (E)-3-(4-((E)-4-Chloro-2-(2-chloro-4-fluorophenyl)-1-(1H-indazol-5-yl)but-1-en-1-yl)phenyl)acrylic acid | 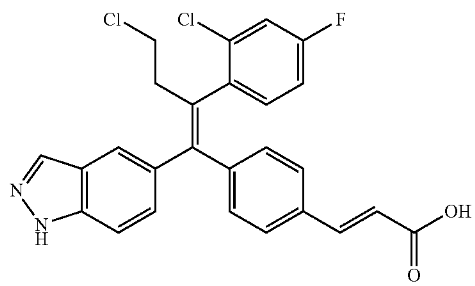 | 481 |
| 68 | (E)-3-(4-((Z)-3,3,3-Trifluoro-1-(1H-indazol-5-yl)-2-phenylprop-1-en-1-yl)phenyl)acrylic acid | 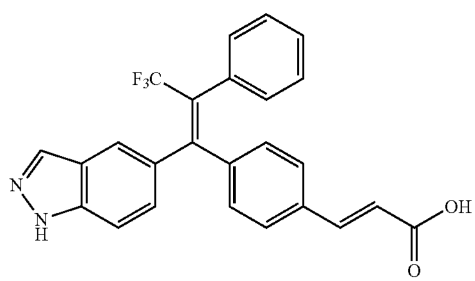 | not observed |
| 69 | (E)-3-(4-((E)-1-(4-Fluoro-1H-indazol-5-yl)-2-(4-fluoro-2-methylphenyl)but-1-en-1-yl)phenyl)acrylic acid | 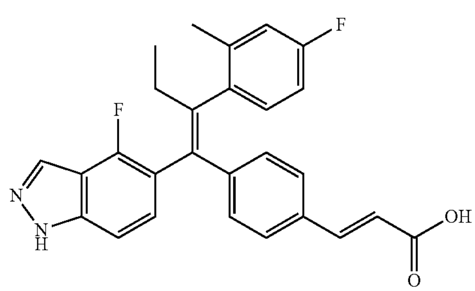 | 445 |
| 70 | (E)-3-(4-((E)-2-(4-Chloro-2-methylphenyl)-1-(4-fluoro-1H-indazol-5-yl)but-1-en-1-yl)phenyl)acrylic acid | 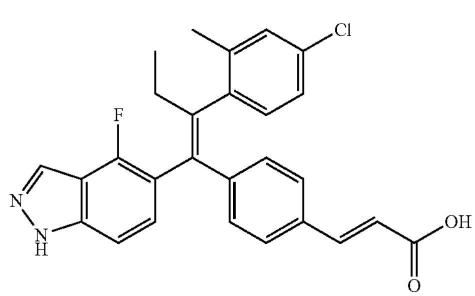 | 461 |

TABLE 1-continued

| Compound Name | Structure | LCMS* [M + H]+ |
|---|---|---|
| 71 (E)-3-(4-((E)-2-Cyclopropyl-1-(4-fluoro-1H-indazol-5-yl)-2-(4-fluoro-2-methylphenyl)vinyl)phenyl) acrylic acid | | 457 |
| 72 (E)-3-(4-((E)-2-(4-Chloro-2-methylphenyl)-2-cyclopropyl-1-(4-fluoro-1H-indazol-5-yl)vinyl)phenyl) acrylic acid | | 473 |
| 73 (E)-3-(4-((E)-1-(4-Chloro-1H-indazol-5-yl)-2-(2-chloro-4-fluorophenyl)but-1-en-1-yl)phenyl)acrylic acid | | 481 |
| 74 (E)-3-(4-((Z)-2-(2-Chloro-4-fluorophenyl)-3,3-difluoro-1-(1H-indazol-5-yl)prop-1-en-1-yl)phenyl)acrylic acid | | 469 |
| 75 (E)-3-(4-((E)-2-Cyclopropyl-1-(4-fluoro-1H-indazol-5-yl)-2-phenylvinyl)phenyl)acrylic acid | | 425 |

TABLE 1-continued

| Compound Name | Structure | LCMS* [M + H]+ |
|---|---|---|
| 76 (E)-3-(4-((E)-4-Chloro-1-(4-fluoro-1H-indazol-5-yl)-2-phenylbut-1-en-1-yl)phenyl)acrylic acid | 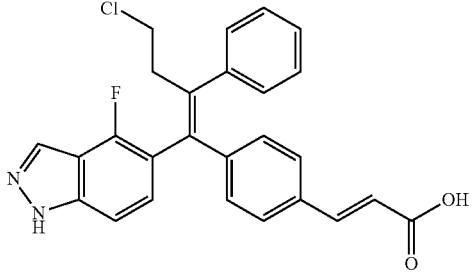 | 447 |
| 77 (E)-3-(4-((E)-4-Chloro-2-(2-chloro-4-fluorophenyl)-1-(4-fluoro-1H-indazol-5-yl)but-1-en-1-yl)phenyl)acrylic acid | 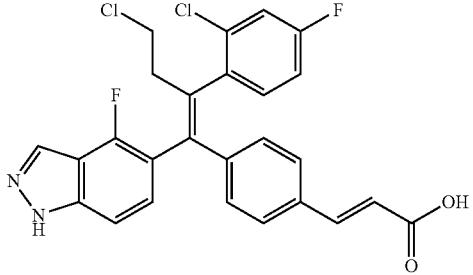 | 499 |
| 78 (E)-3-(4-((E)-4-Fluoro-2-(4-fluorophenyl)-1-(1H-indazol-5-yl)but-1-en-1-yl)phenyl)acrylic acid | 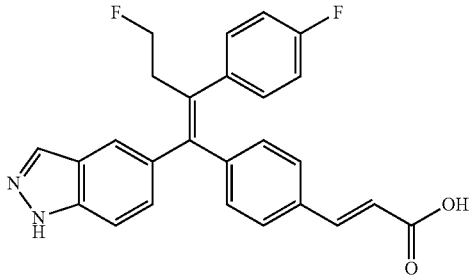 | 431 |
| 79 (E)-3-(4-((E)-4-Fluoro-1-(4-fluoro-1H-indazol-5-yl)-2-phenylbut-1-en-1-yl)phenyl)acrylic acid | 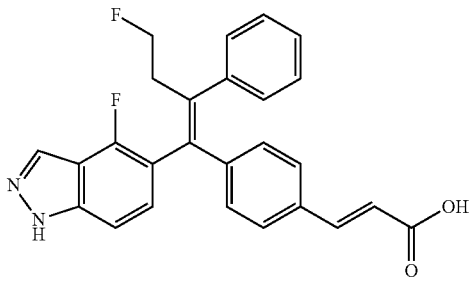 | 431 |
| 80 (E)-3-(4-((E)-1-(1H-Indazol-5-yl)-5-methoxy-2-phenylpent-1-en-1-yl)phenyl)acrylic acid | 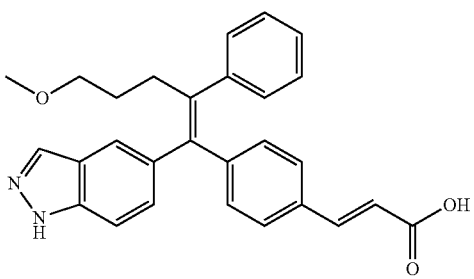 | 439 |

TABLE 1-continued

| Compound Name | Structure | LCMS* [M + H]+ |
|---|---|---|
| 81 (E)-3-(4-((E)-1-(1H-Indazol-5-yl)-6-methoxy-2-phenylhex-1-en-1-yl)phenyl)acrylic acid | | 453 |
| 82 (E)-3-(4-((E)-2-(2-Chloro-4-fluorophenyl)-1-(1H-indazol-5-yl)-3-methylbut-1-en-1-yl)phenyl)acrylic acid | | 461 |
| 83 (E)-3-(4-((E)-1-(1H-Indazol-5-yl)-2-(3-(trifluoromethoxy)phenyl)but-1-en-1-yl)phenyl)acrylic acid | | 479 |
| 84 (E)-3-(4-((E)-2-Cyclobutyl-1-(1H-indazol-5-yl)-2-phenylvinyl)phenyl)acrylic acid | | 421 |
| 85 (E)-3-(4-((E)-2-(2-Chloro-4-fluorophenyl)-2-cyclobutyl-1-(1H-indazol-5-ypvinyl)phenyl)acrylic acid | | 473 |

TABLE 1-continued

| Compound | Name | Structure | LCMS* [M + H]+ |
|---|---|---|---|
| 86 | (E)-3-(4-((E)-1-(3-Fluoro-1H-indazol-5-yl)-2-phenylbut-1-en-1-yl)phenyl)acrylic acid | 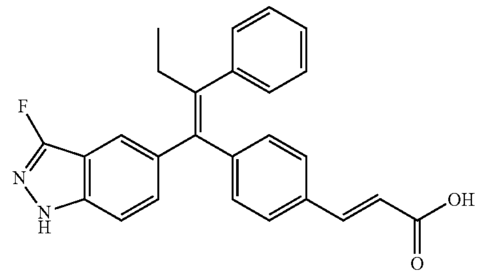 | 413 |
| 87 | (E)-3-(4-((E)-2-Cyclobutyl-1-(3-fluoro-1H-indazol-5-yl)-2-phenylvinyl)phenyl)acrylic acid | 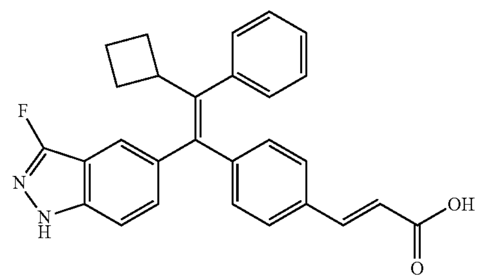 | 439 |
| 88 | (E)-3-(4-((E)-2-(2-Chloro-4-fluorophenyl)-1-(3-fluoro-1H-indazol-5-yl)but-1-en-1-yl)phenyl)acrylic acid | 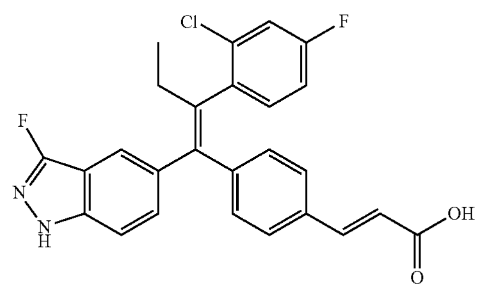 | 465 |
| 89 | (E)-3-(4-((E)-2-(2-Chloro-4-fluorophenyl)-2-cyclobutyl-1-(3-fluoro-1H-indazol-5-yl)vinyl)phenyl)acrylic acid | 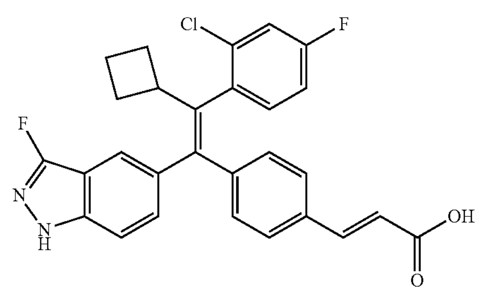 | 491 |
| 90 | (E)-Ethyl 3-(4-((E)-2-(4-fluorophenyl)-1-(1H-indazol-5-yl)but-1-en-1-yl)phenyl)acrylate | 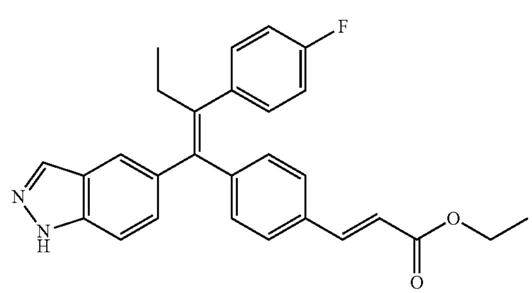 | 441 |

TABLE 1-continued

| Compound Name | | Structure | LCMS* [M + H]+ |
|---|---|---|---|
| 91 | (E)-Ethyl 3-(4-((E)-1-(1H-Indazol-5-yl)-2-(2-methoxyphenyl)but-1-en-1-yl)phenyl)acrylate | 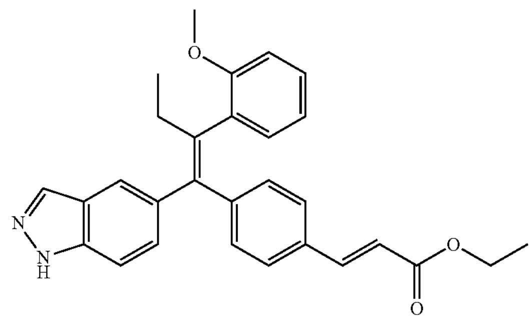 | 453 |
| 92 | (E)-Ethyl 3-(4-((E)-1-(1H-Indazol-5-yl)-2-(4-methoxyphenyl)but-1-en-1-yl)phenyl)acrylate | 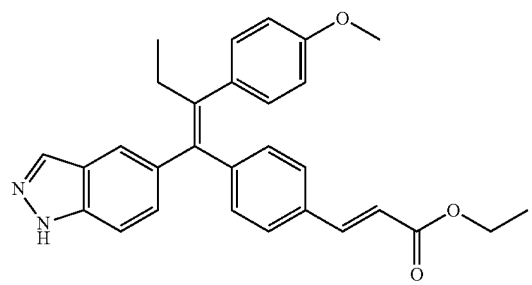 | 453 |
| 93 | (E)-3-(4-((E)-2-(3-Hydroxyphenyl)-1-(1H-indazol-5-yl)but-1-en-1-yl)phenyl)acrylic acid | 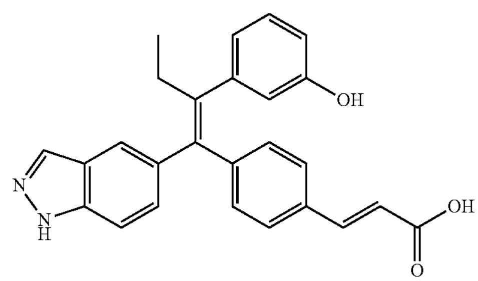 | 411 |
| 94 | (E)-3-(4-((E)-2-(2-Hydroxyphenyl)-1-(1H-indazol-5-yl)but-1-en-1-yl)phenyl)acrylic acid | 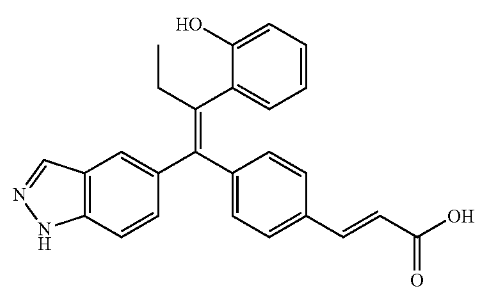 | 411 |
| 95 | (E)-3-(4-((E)-2-(4-Hydroxyphenyl)-1-(1H-indazol-5-yl)but-1-en-1-yl)phenyl)acrylic acid | 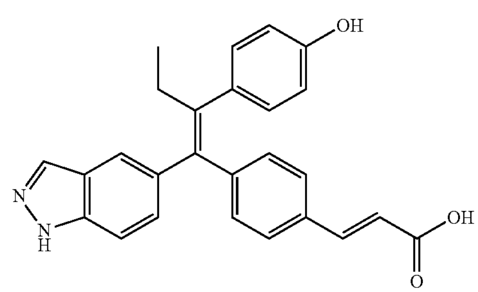 | 411 |

TABLE 1-continued

| Compound Name | Structure | LCMS* [M + H]+ |
|---|---|---|
| 96 (E)-3-(4-((E)-2-(3-Butoxyphenyl)-1-(1H-indazol-5-yl)but-1-en-1-yl)phenyl)acrylic acid | | 467 |
| 97 (E)-3-(4-((E)-2-(4-Butoxyphenyl)-1-(1H-indazol-5-yl)but-1-en-1-yl)phenyl)acrylic acid | | 467 |
| 98 (E)-3-(4-((E)-1-(1H-Indazol-5-yl)-2-(2-(methylsulfonyl)phenyl)but-1-en-1-yl)phenyl)acrylic acid | | 473 |
| 99 (E)-3-(4-((E)-1-(1H-Indazol-5-yl)-2-phenylbut-1-en-1-yl)phenyl)-2-methylacrylic acid | | 409 |
| 100 (E)-3-(4-((Z)-1-(1H-Indazol-5-yl)-2-phenylbut-1-en-1-yl)-3-methylphenyl)acrylic acid | | 409 |

TABLE 1-continued

| Compound Name | | Structure | LCMS* [M + H]+ |
|---|---|---|---|
| 101 | (E)-3-(4-((E)-1-(1H-Indazol-5-yl)-2-phenylbut-1-en-1-yl)-2-methylphenyl)acrylic acid | 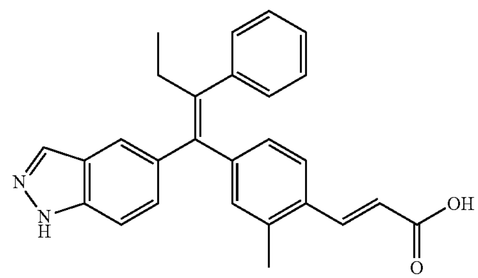 | 409 |
| 102 | (E)-3-(4-((Z)-1-(1H-Indazol-5-yl)-2-phenylbut-1-en-1-yl)-2-chlorophenyl)acrylic acid | 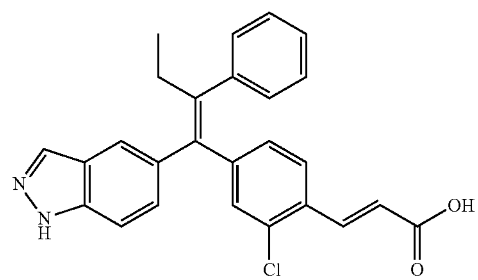 | 429 |
| 103 | (Z)-3-(4-((E)-1-(1H-Indazol-5-yl)-2-phenylbut-1-en-1-yl)phenyl)-2-fluoroacrylic acid | 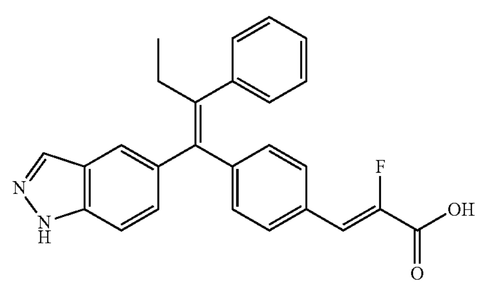 | 413 |
| 104 | (Z)-3-(4-((E)-1-(1H-Indazol-5-yl)-2-phenylbut-1-en-1-yl)phenyl)-2-chloroacrylic acid | 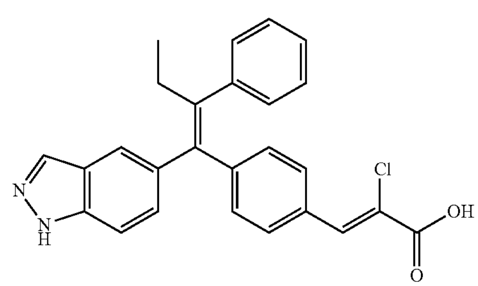 | 429 |
| 105 | (E)-3-(4-((Z)-1-(1H-Indazol-5-yl)-2-phenylbut-1-en-1-yl)-3-fluorophenyl)acrylic acid | 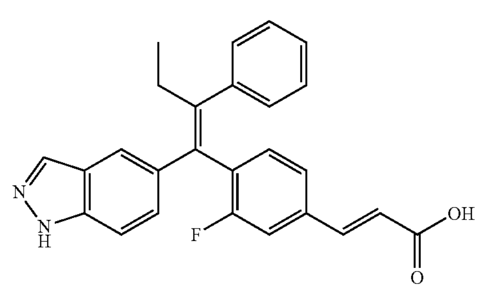 | 413 |

TABLE 1-continued

| Compound Name | Structure | LCMS* [M + H]+ |
|---|---|---|
| 106 (E)-3-(4-((Z)-1-(1H-Indazol-5-yl)-2-phenylbut-1-en-1-yl)-2-fluorophenyl)acrylic acid | 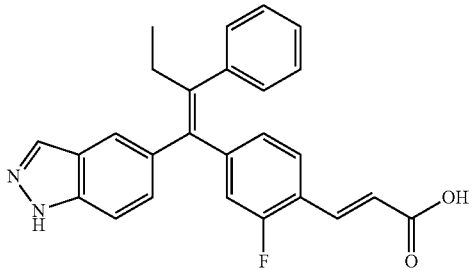 | 413 |
| 107 (E)-3-(4-((Z)-1-(1H-Indazol-5-yl)-2-phenylbut-1-en-1-yl)-2-(trifluoromethyl)phenyl)acrylic acid | 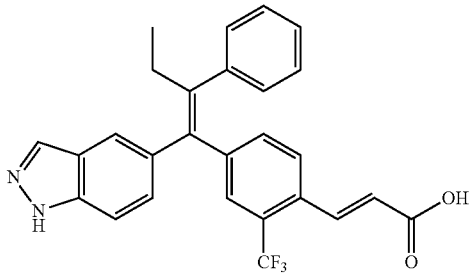 | 463 |
| 108 (E)-3-(4-((Z)-1-(1H-Indazol-5-yl)-2-phenylbut-1-en-1-yl)-3-methoxyphenyl)acrylic acid | 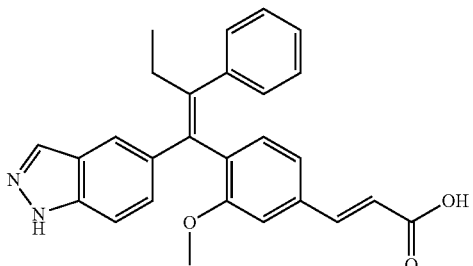 | 425 |
| 109 (E)-3-(4-((Z)-1-(1H-Indazol-5-yl)-2-phenylbut-1-en-1-yl)-2-methoxyphenyl)acrylic acid | 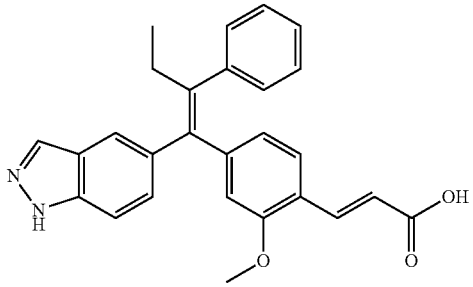 | 425 |
| 110 (E)-Ethyl 3-(4-((E)-2-(2-chloro-4-fluorophenyl)-1-(1H-indazol-5-yl)but-1-en-1-yl)phenyl)acrylate hydrochloride | 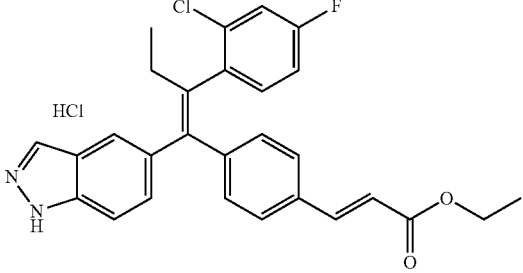 | 475 |

TABLE 1-continued

| Compound | Name | Structure | LCMS* [M + H]+ |
|---|---|---|---|
| 111 | (E)-3-(4-((E)-2-(2-Chloro-4-fluorophenyl)-1-(1H-indazol-5-yl)but-1-en-1-yl)phenyl)acrylic acid | 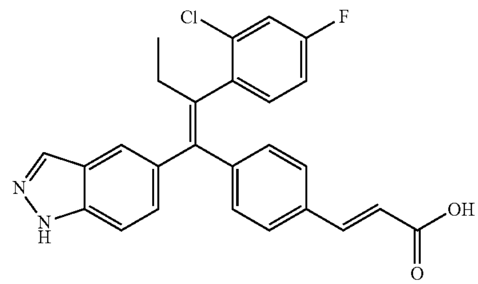 | 447 |
| 112 | (E)-Ethyl 3-(4-((E)-2-(2,4-dichlorophenyl)-1-(1H-indazol-5-yl)but-1-en-1-yl)phenyl)acrylate | 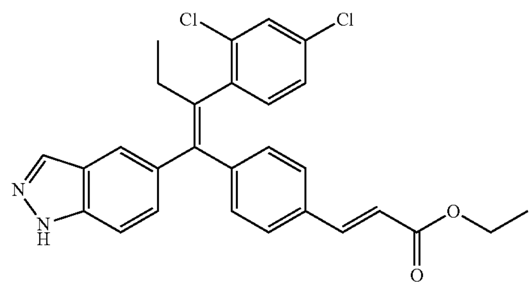 | 491 |
| 113 | (E)-3-(4-((E)-2-(2,4-Dichlorophenyl)-1-(1H-indazol-5-yl)but-1-en-1-yl)phenyl)acrylic acid | 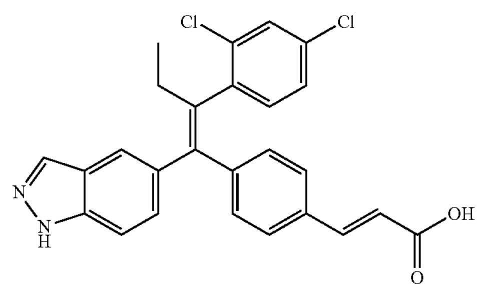 | 463 |
| 114 | (E)-3-(4-((E)-2-(4-Chloro-2-(trifluoromethyl)phenyl)-1-(1H-indazol-5-yl)but-1-en-1-yl)phenyl)acrylic acid | 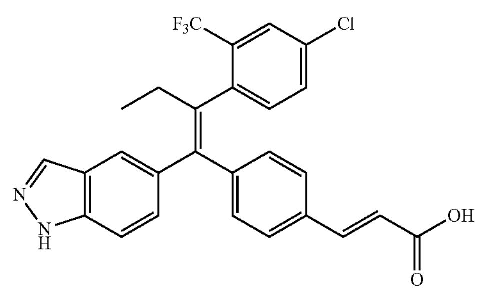 | 497 |
| 115 | (E)-3-(4-((E)-2-(2-Chloro-4-fluorophenyl)-2-cyclopropyl-1-(1H-indazol-5-yl)vinyl)phenyl)acrylic acid | 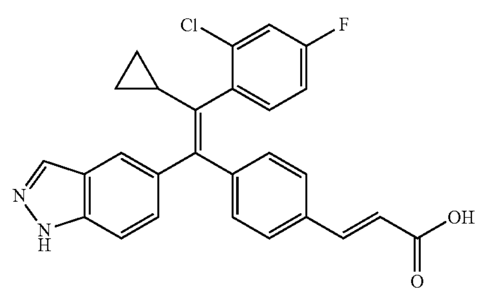 | 459 |

TABLE 1-continued

| | Compound Name | Structure | LCMS* [M + H]+ |
|---|---|---|---|
| 116 | (E)-3-(4-((E)-2-(4-Fluoro-2-(trifluoromethyl)phenyl)-1-(1H-indazol-5-yl)but-1-en-1-yl)phenyl)acrylic acid | 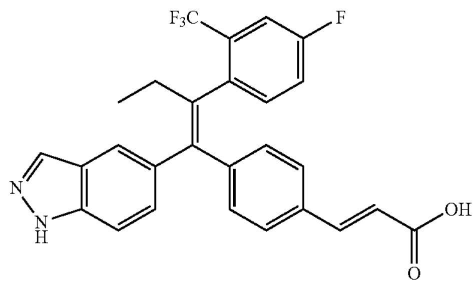 | 481 |
| 117 | (E)-3-(4-(1-(4-Fluoro-1H-indazol-5-yl)-2-(4-fluoro-2-(trifluoromethyl)phenyl)butyl)phenyl)acrylic acid | 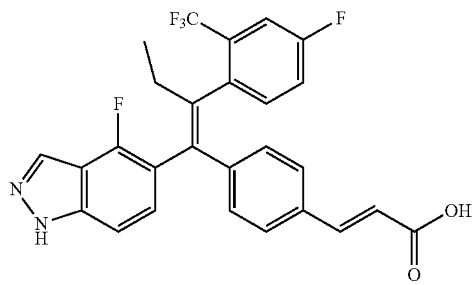 | 499 |
| 118 | (E)-3-(4-((E)-2-(2,4-Dichlorophenyl)-1-(4-fluoro-1H-indazol-5-yl)but-1-en-1-yl)phenyl)acrylic acid | 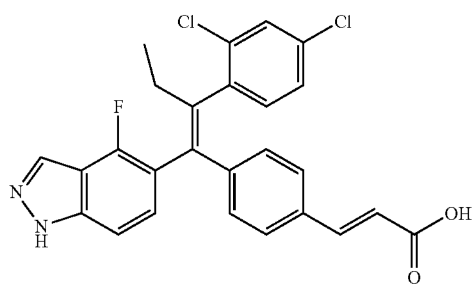 | 481 |
| 119 | (E)-3-(4-((E)-2-(4-Chloro-2-(trifluoromethyl)phenyl)-1-(4-fluoro-1H-indazol-5-yl)but-1-en-1-yl)phenyl)acrylic acid | 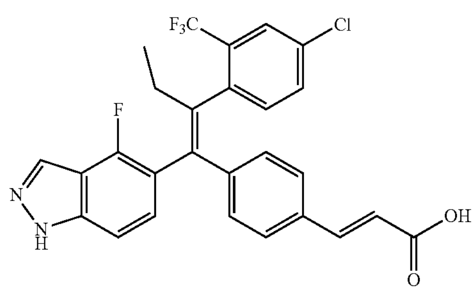 | 515 |
| 120 | (E)-3-(4-((E)-2-(2-Chloro-4-fluorophenyl)-4-fluoro-1-(1H-indazol-5-yl)but-1-en-1-yl)phenyl)acrylic acid | 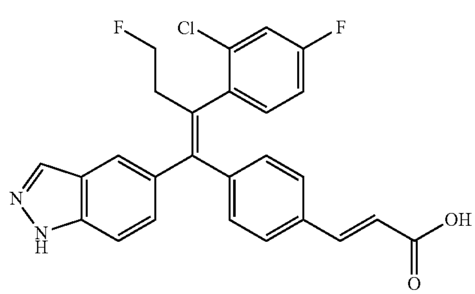 | 465 |

TABLE 1-continued

| Compound Name | | LCMS* [M + H]+ |
|---|---|---|
| 121 | (E)-3-(4-((E)-2-(2-Chloro-4-methoxyphenyl)-1-(1H-indazol-5-yl)but-1-en-1-yl)phenyl)acrylic acid | 459 |
| 122 | (E)-3-(4-((E)-2-(2,4-Dichlorophenyl)-4-fluoro-1-(4-fluoro-1H-indazol-5-yl)but-1-en-1-yl)phenyl)acrylic acid | 499 |
| 123 | (E)-3-(4-((E)-2-Cyclopropyl-2-(2,4-dichlorophenyl)-1-(4-fluoro-1H-indazol-5-yl)vinyl)phenyl)acrylic acid | 493 |
| 124 | (E)-3-(4-((E)-2-(2-Chloro-4-fluorophenyl)-2-cyclopropyl-1-(4-fluoro-1H-indazol-5-yl)vinyl)phenyl)acrylic acid | 477 |
| 125 | (E)-3-(4-((E)-2-Cyclopropyl-2-(2,4-dichlorophenyl)-1-(1H-indazol-5-yl)vinyl)phenyl)acrylic acid | 475 |

TABLE 1-continued

| Compound Name | | Structure | LCMS* [M + H]+ |
|---|---|---|---|
| 126 | (E)-3-(4-((E)-2-(4-Chloro-2-methylphenyl)-2-cyclopropyl-1-(1H-indazol-5-yl)vinyl)phenyl)acrylic acid | 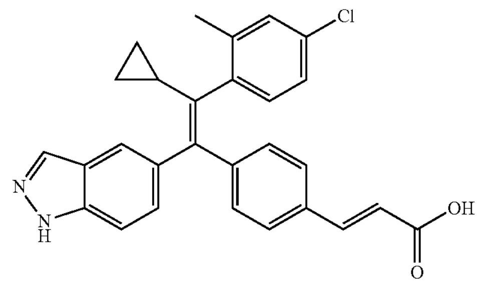 | 455 |
| 127 | (E)-3-(4-((E)-1-(1H-Indazol-5-yl)-2-(2-methyl-5-(methylsulfonyl)phenyl)but-1-en-1-yl)phenyl)acrylic acid | 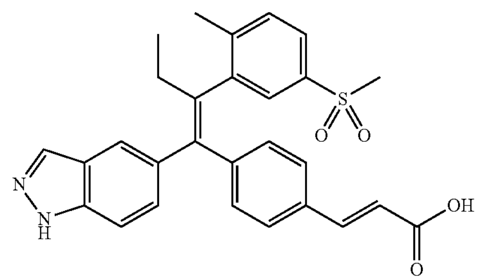 | 487 |
| 128 | (E)-3-(4-((E)-1-(1H-Indazol-5-yl)-2-(4-methoxy-2-methylphenyl)but-1-en-1-yl)phenyl)acrylic acid | 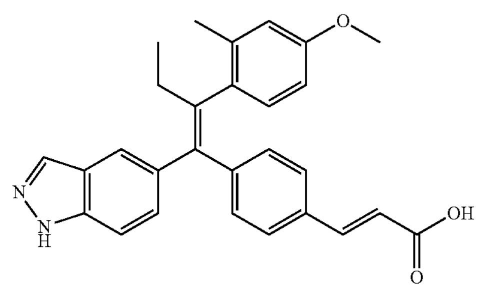 | 439 |
| 129 | (E)-3-(4-((E)-2-(2-Fluoro-4-methoxyphenyl)-1-(1H-indazol-5-yl)but-1-en-1-yl)phenyl)acrylic acid | 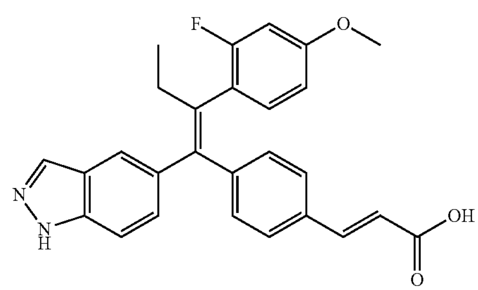 | 443 |
| 130 | (E)-3-(4-((E)-2-(2-Chloro-5-methoxyphenyl)-1-(1H-indazol-5-yl)but-1-en-1-yl)phenyl)acrylic acid | 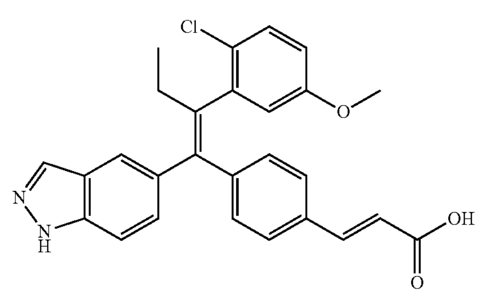 | 459 |

TABLE 1-continued

| Compound | Name | Structure | LCMS* [M + H]+ |
|---|---|---|---|
| 131 | (E)-3-(4-((E)-2-(2-Fluoro-4-(methylsulfonyl)phenyl)-1-(1H-indazol-5-yl)but-1-en-1-yl)phenyl)acrylic acid | 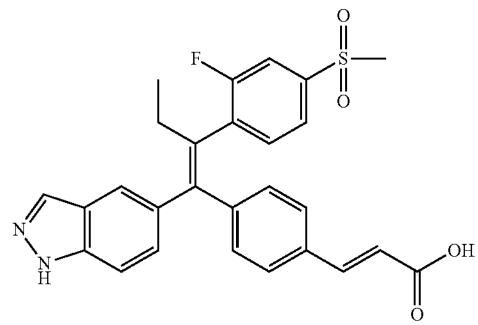 | 491 |
| 132 | (E)-3-(4-((E)-2-(2,4-Dichlorophenyl)-3,3,4,4,4-pentadeutero-1-(1H-indazol-5-yl)but-1-en-1-yl)phenyl)acrylic acid | 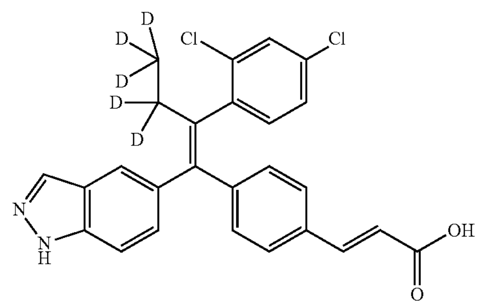 | 468 |
| 133 | (E)-3-(4-((E)-1-(1H-Indazol-5-yl)-2-(3-(methylsulfonyl)phenyl)but-1-en-1-yl)phenyl)acrylic acid | 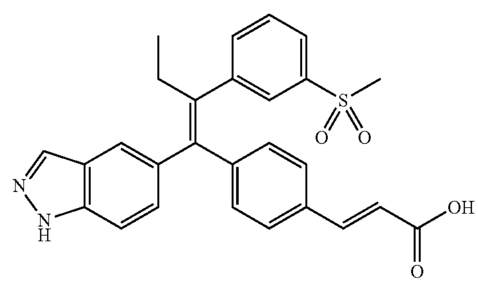 | 473 |
| 134 | (E)-3-(4-((E)-2-(2,4-Dichlorophenyl)-1-(7-fluoro-1H-indazol-5-yl)but-1-en-1-yl)phenyl)acrylic acid | 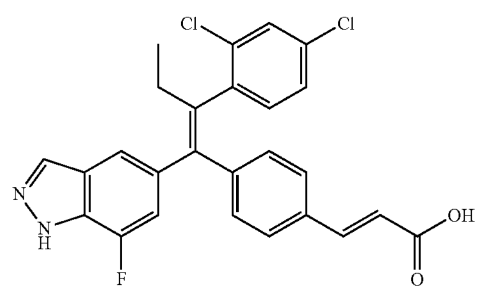 | 481 |
| 135 | (E)-3-(4-((E)-2-(2-Chloro-3-methoxyphenyl)-1-(1H-indazol-5-yl)but-1-en-1-yl)phenyl)acrylic acid | 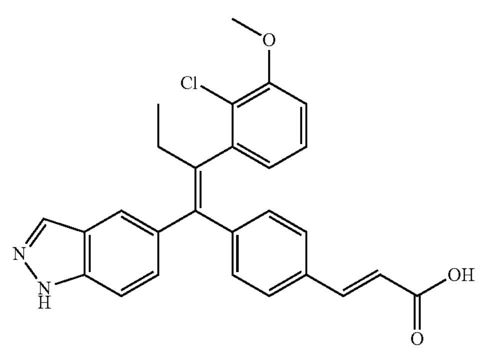 | 459 |

TABLE 1-continued

| Compound Name | | Structure | LCMS* [M + H]+ |
|---|---|---|---|
| 136 | (E)-3-(4-((E)-2-(2-Chloro-4-fluorophenyl)-3,3,4,4,4-pentadeutero-1-(1H-indazol-5-yl)but-1-en-1-yl)phenyl)acrylic acid | 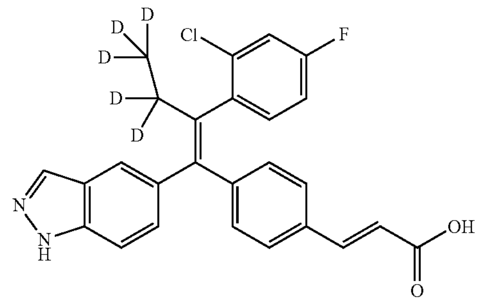 | 452 |
| 137 | (E)-3-(4-((E)-2-(4-Chloro-2-cyanophenyl)-1-(1H-indazol-5-yl)but-1-en-1-yl)phenyl)acrylic acid | 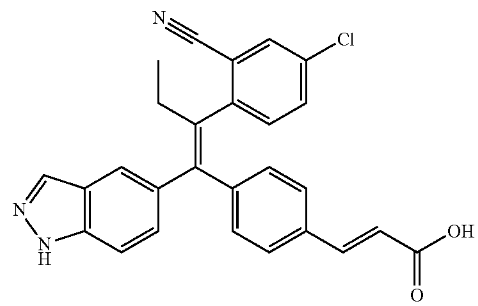 | 454 |
| 138 | (E)-3-(4-((E)-2-(2-Cyano-4-fluorophenyl)-1-(1H-indazol-5-yl)but-1-en-1-yl)phenyl)acrylic acid | 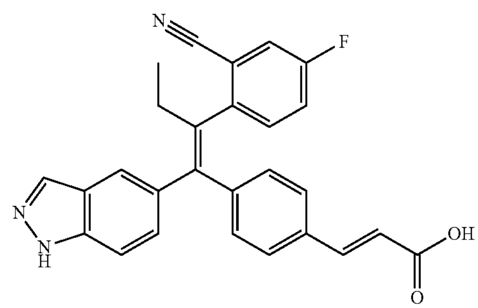 | 438 |
| 139 | (E)-3-(4-((E)-2-(2-Cyano-4-(trifluoromethyl)phenyl)-1-(1H-indazol-5-yl)but-1-en-1-yl)phenyl)acrylic acid | 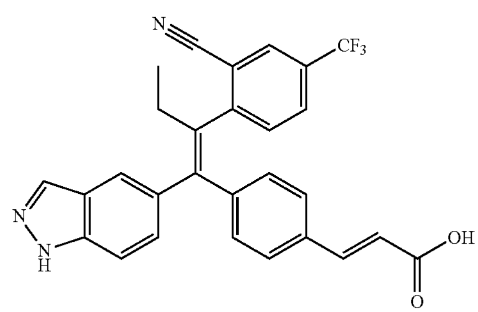 | 488 |
| 140 | (E)-3-(4-((E)-2-(2-Chloro-4-cyanophenyl)-1-(1H-indazol-5-yl)but-1-en-1-yl)phenyl)acrylic acid | 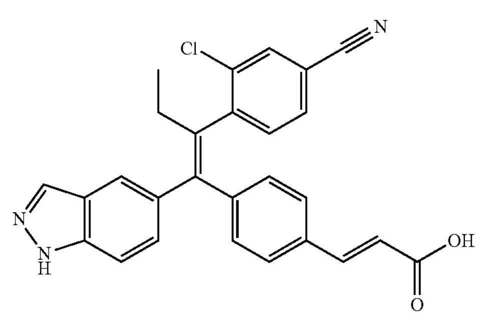 | 454 |

TABLE 1-continued

| Compound Name | | Structure | LCMS* [M + H]+ |
|---|---|---|---|
| 141 | (E)-3-(4-((E)-2-(3-Cyano-2-methylphenyl)-1-(1H-indazol-5-yl)but-1-en-1-yl)phenyl)acrylic acid | 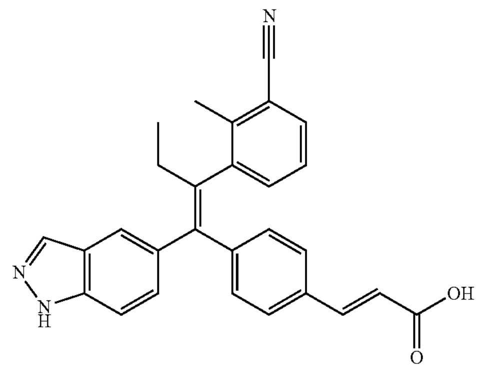 | 434 |
| 142 | (E)-3-(4-((E)-2-(4-Cyano-2-methylphenyl)-1-(1H-indazol-5-yl)but-1-en-1-yl)phenyl)acrylic acid | 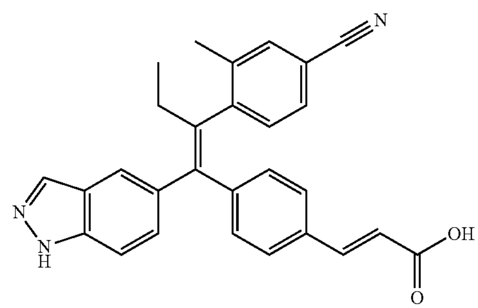 | 434 |
| 143 | (E)-3-(4-((E)-2-(5-Cyano-2-methylphenyl)-1-(1H-indazol-5-yl)but-1-en-1-yl)phenyl)acrylic acid | 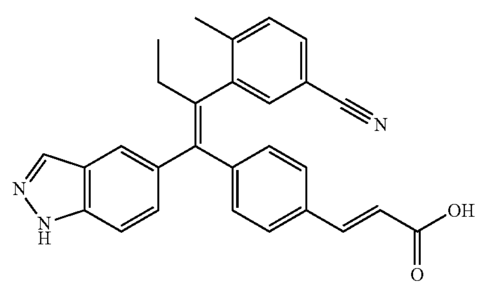 | 434 |
| 144 | (E)-3-(4-((E)-2-(2-Cyano-4-methoxyphenyl)-1-(1H-indazol-5-yl)but-1-en-1-yl)phenyl)acrylic acid | 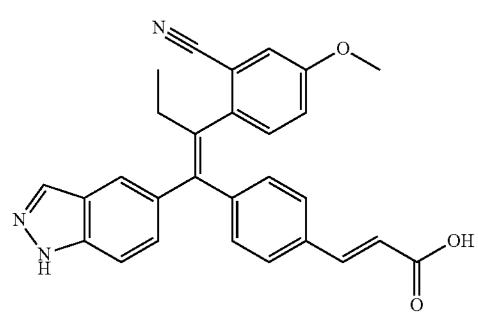 | 450 |

TABLE 1-continued

| Compound Name | | Structure | LCMS* [M + H]+ |
|---|---|---|---|
| 145 | (E)-3-(4-((E)-2-(2-Chlorophenyl)-1-(1-methyl-1H-indazol-5-yl)but-1-en-1-yl)phenyl)acrylic acid | 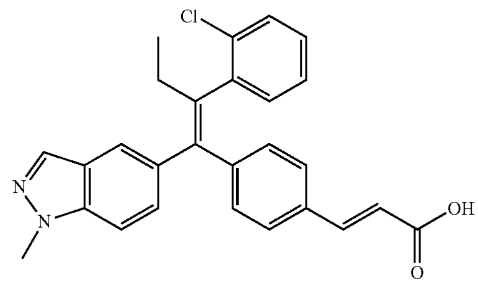 | 443 |
| 146 | (E)-3-(4-((E)-2-Cyclobutyl-1-(1-methyl-1H-indazol-5-yl)-2-phenylvinyl)phenyl)acrylic acid | 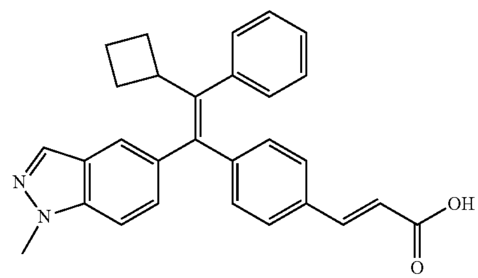 | 435 |
| 147 | (E)-3-(4-((E)-2-(2-Chloro-4-fluorophenyl)-1-(1-methyl-1H-indazol-5-yl)but-1-en-1-yl)phenyl)acrylic acid | 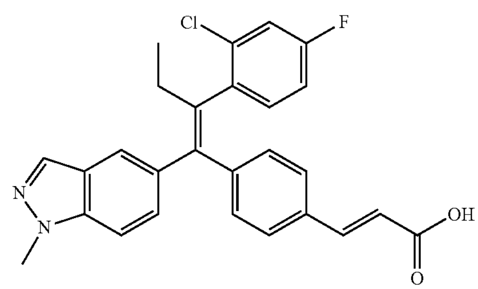 | 461 |
| 148 | (E)-3-(4-((E)-2-(2-Chloro-4-fluorophenyl)-1-(1-(difluoromethyl)-1H-indazol-5-yl)but-1-en-1-yl)phenyl)acrylic acid | 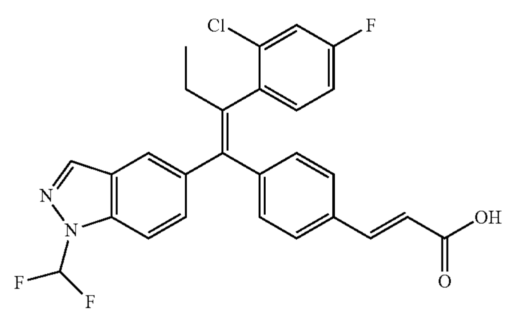 | 497 |

*mass spectrometric data

Synthesis of Compounds

Compounds of Formula (I), described herein, are synthesized using standard synthetic techniques or using methods known in the art in combination with methods described herein. In addition, solvents, temperatures and other reaction conditions presented herein may vary.

The starting material used for the synthesis of the compounds of Formula (I) are either synthesized or obtained from commercial sources, such as, but not limited to, Sigma-Aldrich, Fluka, Acros Organics, Alfa Aesar, and the like. The compounds described herein, and other related compounds having different substituents are synthesized using techniques and materials described herein or otherwise known, including those found in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999). General methods for the preparation of compounds is optionally modified by the use of appropriate reagents and conditions for the introduction of the various moieties found in the formulae as provided herein.

In some embodiments, exemplary compounds of Formula (I) are prepared as outlined in the following Schemes.

Scheme 1:

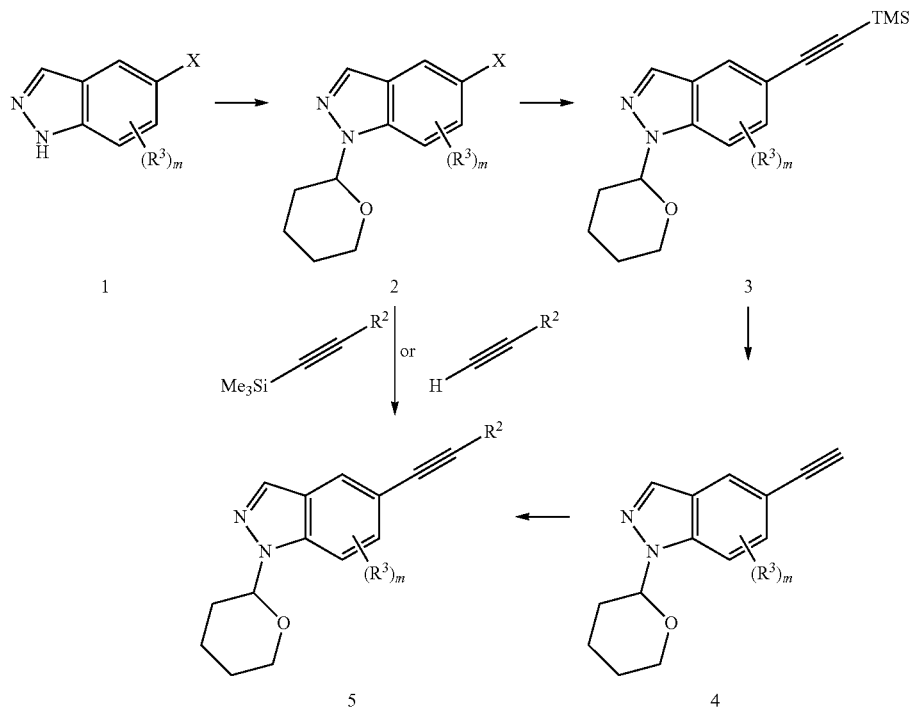

Protection of the acidic proton bearing nitrogen of compounds of structure 1 with a protecting group provides compounds of Structure 2. In some embodiments, the protecting group is tetrahydro-2H-pyran (THP). In some embodiments, the conditions for nitrogen protection require 3,4-dihydro-2H-pyran (DHP), an organic acid and a suitable solvent. In some embodiments, the organic acid is pyridinium p-toluenesulfonate (PPTS) or p-toluenesulfonic acid (p-TSA or p-TsOH) and the suitable solvent is dichloromethane. In some embodiments, the reaction is performed at room temperature. Other conditions to protect the nitrogen of the starting material are known. A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Compounds of structure 2, where X is a halogen or other suitable leaving group, are reacted with a protected acetylene (e.g., trimethylsilylacetylene) under Sonogashira reaction conditions to provide compounds of Structure 3. In some embodiments, the Sonogashira coupling reaction conditions include the use of a palladium catalyst and a copper halide salt. In some embodiments, the Sonogashira reaction conditions in the use of Pd(Ph$_3$P)$_2$Cl$_2$, CuI, and triethylamine. In one embodiment, the reaction is performed at about 80° C. Other suitable reaction conditions are described in Rafael Chinchilla and Carmen Nájera (2007). Chem. Rev. 107 (3): 874-922.

The silyl protecting group of compounds of structure 3 is removed under suitable reaction conditions to provide compounds of structure 4. In some embodiments, the silyl protecting group is removed with potassium carbonate (K$_2$CO$_3$) in methanol. In other embodiments, the silyl protecting group is removed with tetrabutylammoniumfluoride (TBAF) in tetrahydrofuran.

In some embodiments, acetylenes of Structure 4 are reacted with R$^2$—X under basic condition to prepare compounds of Structure 5. In these instances, R$^2$ is C$_1$-C$_6$alkyl or C$_1$-C$_6$fluoroalkyl or C$_1$-C$_4$alkoxy or C$_1$-C$_4$fluoroalkoxy or C$_3$-C$_6$cycloalkyl, or the like, and X is a suitable leaving group. In some embodiments, R$^2$ moieties are installed by other suitable conditions.

In some embodiments, compounds of structure 2 are coupled with an alkynyl-trimethylsilane or a terminal-alkyne under Sonogashira reaction conditions to provide compounds of structure 5. In some embodiments, the coupling of an alkynyl-trimethylsilane with compounds of structure 2 includes the use of a base (e.g. cesium carbonate), a palladium catalyst (e.g. Pd(OAc)$_2$, dppf) and a copper halide salt (e.g. CuI) in a suitable solvent (e.g. dimethylacetamide), at elevated temperatures (e.g. about 80-90° C.). In some embodiments, the coupling of a terminal-alkyne with compounds of structure 2 includes the use of Pd(PPh$_3$)$_2$Cl$_2$), CuI, and triethylamine, with the reaction performed with at elevated temperatures (e.g. about 80-120° C.).

Scheme 2.

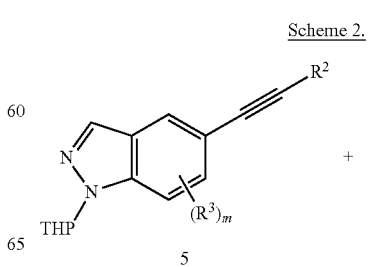

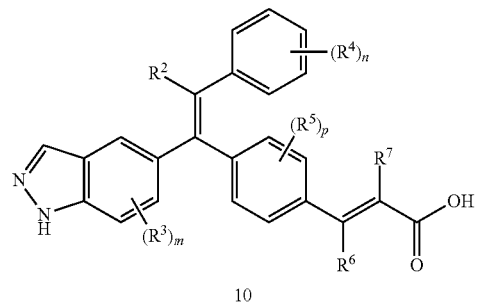

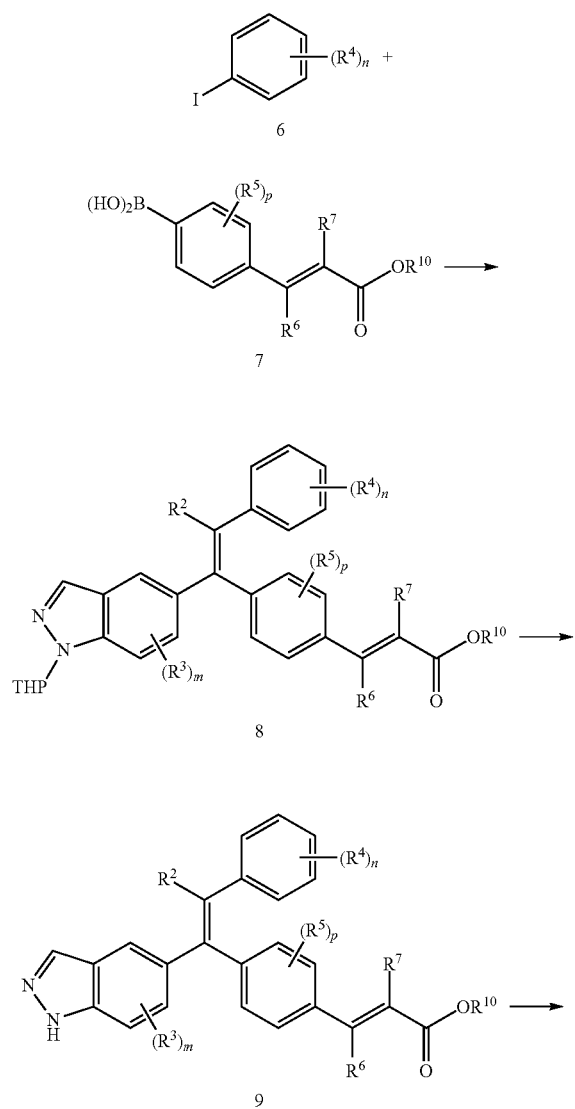

Compounds of Structures 5, 6 and 7 are then coupled together under suitable reaction conditions to afford compounds of Structure 8. In some embodiments, the suitable reaction conditions include the use of organometallic reagent(s). In some embodiments, the suitable reaction conditions include the use of a palladium catalyst. In some embodiments, the suitable reaction conditions include the use of $Pd(PhCN)_2Cl_2$, $K_2CO_3$ in dimethylformamide/water. Other suitable reaction conditions include those described in Chengxiang Zhou and Richard C. Larock, Journal of Organic Chemistry, 2005, 70, 3765-3777; Chengxiang Zhou, Daniel E. Emrich, and Richard C. Larock Organic Letters 2003, 1579-1582; Tsutomu Konno, Ken-ichi Taku, Takashi Ishihara, Journal of Fluorine Chemistry 127 (2006) 966-972.

The protecting group of compounds of structure 8 is then removed under suitable reaction conditions to provide compounds of structure 9. In some embodiments, the suitable reaction conditions include the use of an acid. In some embodiments, the suitable reaction conditions include the use of hydrochloric acid, ethanol, with the reaction performed at about 70° C.

Hydrolysis of the ester group of compounds of structure 9 provides carboxylic acid compounds of structure 10. In some embodiments, the hydrolysis reaction includes the use of lithium hydroxide in a mixture of tetrahydrofuran and ethanol. Other hydrolysis reaction conditions are known.

In some embodiments, compounds disclosed herein are prepared as outlined in Scheme 3.

Scheme 3:

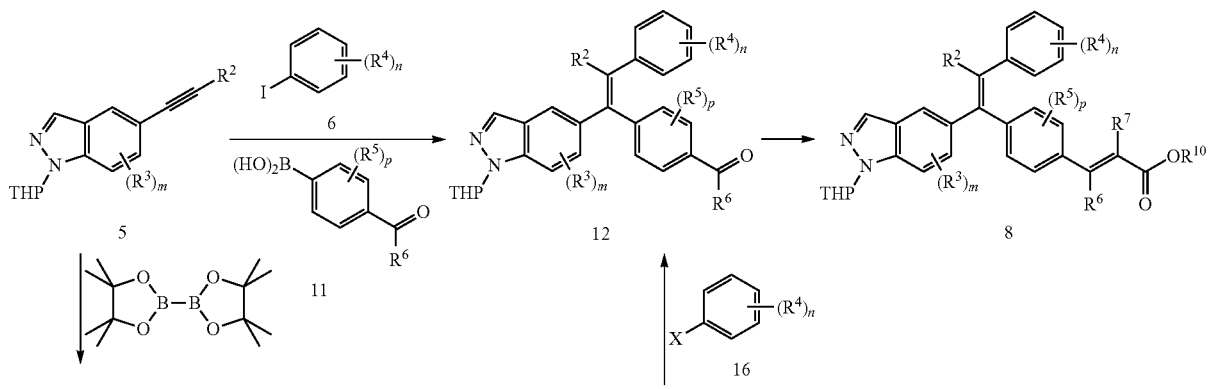

-continued

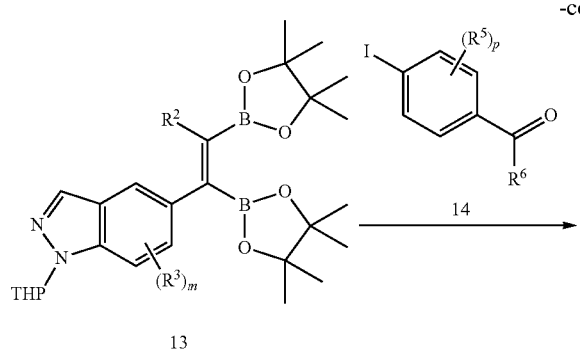
13

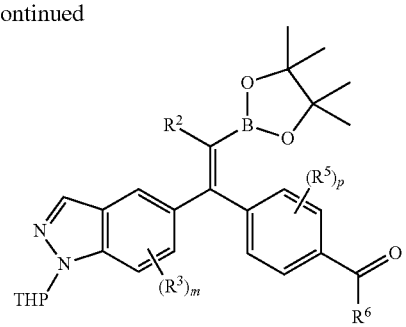
15

In some embodiments, compounds of structure 5 are reacted with phenyl halides of structure 6 and boronic acids of structure 11 under suitable reaction conditions to provide compounds of structure 12. In some embodiments, the suitable reaction conditions include the use of organometallic reagent(s). In some embodiments, the suitable organometallic reagent is a palladium catalyst. The aldehyde of compounds of structure 12 is then transformed to an alkene under suitable reaction conditions to provide compounds of structure 8. Suitable reaction conditions include a Horner-Wadsworth-Emmons olefination reaction or a Wittig olefination reaction conditions.

Alternatively, compounds of structure 5 are reacted with a borylating agent in the presence of a suitable catalyst to provide compounds of structure 13. In some embodiments, the suitable catalyst is an organometallic reagent such as a platinum catalyst. In some embodiments, the amount of catalyst impacts the rate of the reaction, but generally, not the yield or purity. In some embodiments, the solvent has a small impact on the rate of the reaction, but generally, not the yield or purity. In some embodiments, the temperature has a significant impact on the rate of the reaction, but generally, not the yield or purity. A Suzuki cross-coupling is then performed with compounds of structure 13 and phenyl halides of structure 14 to provide compounds of structure 15. In some embodiments, 2 or 3 equivalents of base (e.g. $Cs_2CO_3$) is used in the Suzuki cross-coupling. In some embodiments, 1.3 equivalents of base (e.g. $Cs_2CO_3$) is used in the Suzuki cross-coupling. In some embodiments, the solvent has a significant impact on the rate and regioselectivity of this reaction. In some embodiments, dioxane, DME, or 2-MeTHF is used. In some embodiments, water content has a significant impact on the rate and regioselectivity of this the Suzuki cross-coupling. A subsequent Suzuki cross-coupling is then performed between compounds of structure 15 and phenyl halides of structure 16 to provide compounds of structure 12.

A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Further Forms of Compounds

In instances where the compound of Formula (I) possesses one or more stereocenters, each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Stereoisomers are obtained, if desired, by methods such as, stereoselective synthesis and/or the separation of stereoisomers by chiral chromatographic columns and/or use of optically active resolving agents. Jean Jacques, Andre Collet, Samuel H. Wilen, "Enantiomers, Racemates and Resolutions", John Wiley And Sons, Inc., 1981.

In certain embodiments, the compounds presented herein are present as atropisomers. Atropisomers refer to stereoisomers resulting from hindered rotation about single bonds where the steric strain barrier to rotation allows for the isolation of conformers. Atropisomers display axial chirality. Separation of atropisomers is possible. In some embodiments, separation of atropisomers is possible by chiral resolution methods such as selective crystallization. Atropisomers are optionally characterized by NMR or other suitable characterization means.

The methods and compositions described herein include the use of amorphous forms as well as crystalline forms (also known as polymorphs). In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In some embodiments, compounds described herein are prepared as prodrugs. A "prodrug" refers to an agent that is converted into the parent drug in vivo. Prodrugs are often useful because, in some situations, they are easier to administer than the parent drug or they are bioavailable by oral administration or they have improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. In certain embodiments, upon in vivo administration, a prodrug is chemically converted to the biologically, pharmaceutically or therapeutically active form of the compound.

In some embodiments, sites on the aromatic ring portion of compounds of Formula (I) are susceptible to various metabolic reactions. Incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, deuterium or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

In additional or further embodiments, the compounds described herein are metabolized upon administration to an organism in need to produce a metabolite that is then used to produce a desired effect, including a desired therapeutic effect.

"Pharmaceutically acceptable," as used herein, refers to a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound of Formula (I) with an acid. Pharmaceutically acceptable salts are also obtained by reacting a compound of Formula (I) with a base to form a salt.

Compounds described herein are optionally formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like. In some embodiments, the compounds provided herein are prepared as lysine salts, sodium salts and other suitable amino acid salts. In some embodiments, the compounds provided herein are prepared as a sodium salt. In some embodiments, the compounds provided herein are prepared as an N-methylglucamine salt. In some embodiments, the compounds provided herein are prepared as a hydrochloride salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts of compounds having the structure of Formula (I), as well as active metabolites of these compounds having the same type of activity.

Certain Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" group refers to an aliphatic hydrocarbon group. The alkyl group is saturated or unsaturated. The alkyl moiety, whether saturated or unsaturated, is branched or straight chain. In one aspect the alkyl is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, sec-butyl, tertiary butyl, pentyl, neopentyl, hexyl, allyl, vinyl, acetylene, but-2-enyl, but-3-enyl, and the like.

"Deuteroalkyl" refers to an alkyl group where 1 or more hydrogen atoms of an alkyl are replaced with deuterium.

An "alkoxy" group refers to a (alkyl)O— group, where alkyl is as defined herein.

The term "cycloalkyl" refers to cyclopropyl, cyclobutyl, cyclopentyl, cyclopentenyl, cyclohexyl or cyclohexenyl.

The term "halo" or, alternatively, "halogen" or "halide" means fluoro, chloro, bromo or iodo.

The term "fluoroalkyl" refers to an alkyl in which one or more hydrogen atoms are replaced by a fluorine atom.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. In one aspect, a heteroalkyl is a $C_1$-$C_6$ heteroalkyl.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader.

"Selective estrogen receptor modulator" or "SERM" as used herein, refers to a molecule that differentially modulates the activity of estrogen receptors in different tissues. For example, in some embodiments, a SERM displays ER antagonist activity in some tissues and ER agonist activity in other tissues. In some embodiments, a SERM displays ER antagonist activity in some tissues and minimal or no ER agonist activity in other tissues. In some embodiments, a SERM displays ER antagonist activity in breast tissues, ovarian tissues, endometrial tissues, and/or cervical tissues but minimal or no ER agonist activity in uterine tissues.

The term "antagonist" as used herein, refers to a small-molecule agent that binds to a nuclear hormone receptor and subsequently decreases the agonist induced transcriptional activity of the nuclear hormone receptor.

The term "agonist" as used herein, refers to a small-molecule agent that binds to a nuclear hormone receptor and subsequently increases nuclear hormone receptor transcriptional activity in the absence of a known agonist.

The term "inverse agonist" as used herein, refers to a small-molecule agent that binds to a nuclear hormone receptor and subsequently decreases the basal level of nuclear hormone receptor transcriptional activity that is present in the absence of a known agonist.

The term "degrader" as used herein, refers to a small molecule agent that binds to a nuclear hormone receptor and subsequently lowers the steady state protein levels of said receptor. In some embodiments, a degrader as described herein lowers steady state estrogen receptor levels by at least 10%, at least 20%, at least 30%, at least 40%, at least 50%, at least 60%, at least 65%, at least 70%, at least 75%, at least 80%, at least 85%, at least 90% or at least 95%.

The term "selective estrogen receptor degrader" or "SERD" as used herein, refers to a small molecule agent that preferentially binds to estrogen receptors versus other receptors and subsequently lowers the steady state estrogen receptor levels.

The term "ER-dependent", as used herein, refers to diseases or conditions that would not occur, or would not occur to the same extent, in the absence of estrogen receptors.

The term "ER-mediated", as used herein, refers to diseases or conditions that occur in the absence of estrogen receptors but can occur in the presence of estrogen receptors.

The term "ER-sensitive", as used herein, refers to diseases or conditions that would not occur, or would not occur to the same extent, in the absence of estrogens.

The term "cancer" as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Additional non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenström macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sézary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenström macroglobulinemia, Wilms tumor.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), and a co-agent, are both administered to a patient simultaneously in the form of a single entity or dosage. The term "non-fixed combination" means that the active ingredients, e.g. a compound of Formula (I), and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "subject" or "patient" encompasses mammals. Examples of mammals include, but are not limited to, humans, chimpanzees, apes, monkeys, cattle, horses, sheep, goats, swine, rabbits, dogs, cats, rats, mice, guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration

Suitable routes of administration include, but are not limited to, oral, parenteral (e.g., intravenous, subcutaneous, intramuscular), intranasal, buccal, topical, rectal, aerosol, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections. In certain embodiments, a compound as described herein is administered in a systemic manner. In certain other embodiments, a compound as described herein is administered in a local rather than systemic manner.

Pharmaceutical Compositions/Formulations

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound of Formula (I), with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, antifoaming agents, antioxidants, preservatives, or one or more combination thereof. The pharmaceutical composition facilitates administration of the compound to a mammal.

The pharmaceutical compositions will include at least one compound of Formula (I), or a pharmaceutically acceptable salt thereof, as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, compounds described herein exist in unsolvated form or in solvated forms with pharmaceutically acceptable solvents such as water, ethanol, and the like.

The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, enteric coated formulations, pulsatile release formulations, multiparticulate formulations, and mixed immediate and controlled release formulations.

In some embodiments, the compound of Formula (I), or a pharmaceutically acceptable salt thereof, is administered systemically.

In some embodiments, the compound of Formula (I), or a pharmaceutically acceptable salt thereof, is administered orally. All formulations for oral administration are in dosages suitable for such administration. In some embodiments, the solid dosage forms disclosed herein are in the form of a tablet, a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder. In still other embodiments, the pharmaceutical formulation is in the form of a tablet. In still other embodiments, the pharmaceutical formulation is in the form of a suspension tablet, a fast-melt tablet, a bite-disintegration tablet, a rapid-disintegration tablet, an effervescent tablet, or a caplet. In other embodiments, pharmaceutical formulation is in the form of a capsule.

In some embodiments, the pharmaceutical solid oral dosage forms are formulated to provide a controlled release of the active compound. Controlled release profiles include, for example, sustained release, prolonged release, pulsatile release, and delayed release profiles.

In one aspect, liquid formulation dosage forms for oral administration are in the form of aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002).

For buccal or sublingual administration, the compositions optionally take the form of tablets, lozenges, or gels formulated in a conventional manner.

In one aspect, a compound of Formula (I), or a pharmaceutically acceptable salt thereof, is formulated into a pharmaceutical composition suitable for intramuscular, subcutaneous, or intravenous injection. Parenteral injections involve either bolus injection and/or continuous infusion.

In some embodiments, the compound of Formula (I), or a pharmaceutically acceptable salt thereof, is administered intravenously. In some embodiments, the compound of Formula (I), or a pharmaceutically acceptable salt thereof, is administered subcutaneously.

In some embodiments, the compound of Formula (I), or a pharmaceutically acceptable salt thereof, is administered topically. In such embodiments, the compound of Formula (I), or a pharmaceutically acceptable salt thereof, is formulated into a variety of topically administrable compositions, such as solutions, suspensions, lotions, gels, pastes, shampoos, scrubs, rubs, smears, medicated sticks, medicated bandages, balms, creams or ointments. In some embodiments, the compound of Formula (I), or a pharmaceutically acceptable salt thereof, is administered topically to the skin of mammal. In some embodiments, the compound of Formula (I), is prepared as a transdermal dosage form.

In another aspect is the use of a compound of Formula (I), or a pharmaceutically acceptable salt thereof, in the manufacture of a medicament for treating a disease, disorder or conditions in which the activity of estrogen receptors contributes to the pathology and/or symptoms of the disease or condition. In one aspect, the disease or condition is any of the diseases or conditions specified herein.

Methods of Dosing and Treatment Regimens

In one embodiment, the compound of Formula (I), or a pharmaceutically acceptable salt thereof, is used in the preparation of medicaments for the treatment of diseases or conditions in a mammal that would benefit from a reduction of estrogen receptor activity. Methods for treating any of the diseases or conditions described herein in a mammal in need of such treatment, involves administration of pharmaceutical compositions that include at least one compound of Formula (I), or a pharmaceutically acceptable salt, N-oxide, active metabolite, prodrug, or pharmaceutically acceptable solvate thereof, in therapeutically effective amounts to said mammal.

Therapeutically effective amounts depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In any of the method of treatments described herein, the effective amount of the compound of Formula (I) is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In some situations the methods of treatment comprise single administration of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain embodiments wherein the patient's condition does not improve, upon the doctor's discretion the compound is administered chronically, that is, for an extended period of time.

In certain embodiments wherein a patient's status does improve, the dose of drug being administered is temporarily reduced or temporarily suspended for a certain length of time (i.e., a "drug holiday").

In some embodiments, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day. In one embodiment, the daily dosages appropriate for the compound of Formula (I), or a pharmaceutically acceptable salt thereof, described herein are from about 0.01 to about 50 mg/kg per body weight.

Combination Therapy

In certain instances, it is appropriate to administer at least one compound of Formula (I), or a pharmaceutically acceptable salt thereof, in combination with one or more other therapeutic agents. In certain embodiments, the pharmaceutical composition further comprises one or more anti-cancer agents.

In one specific embodiment, a compound of Formula (I), or a pharmaceutically acceptable salt thereof, is co-administered with a second therapeutic agent, wherein the compound of Formula (I), or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is the additive effect of the two therapeutic agents or the patient may experience a synergistic benefit.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

In some embodiments, methods for treatment of estrogen receptor-dependent or estrogen receptor-mediated conditions or diseases, such as proliferative disorders, including cancer, comprises administration to a mammal a compound of Formula (I), or a pharmaceutically acceptable salt thereof, in combination with at least one additional therapeutic agent.

In some embodiments, a compound of Formula (I), or a pharmaceutically acceptable salt thereof, in combination with hormone blocking therapy, chemotherapy, radiation therapy, monoclonal antibodies, or combinations thereof.

In some embodiments, the at least one additional therapeutic agent for use in combination with a compound of Formula (I), or a pharmaceutically acceptable salt thereof, include one or more of the following: abiraterone; abarelix; adriamycin; actinomycin; acivicin; aclarubicin; acodazole hydrochloride; acronine; adozelesin; aldesleukin; alemtuzumab; allopurinol; alitretinoin; altretamine; ambomycin; ametantrone acetate; aminoglutethimide; aminolevulinic acid; amifostine; amsacrine; anastrozole; anthramycin; aprepitant; arsenic trioxide; asparaginase; asperlin; azacitidine; azetepa; azotomycin; batimastat; bendamustine hydrochloride; benzodepa; bevacizumab; bexarotene; bicalutamide; bisantrene hydrochloride; bisnafide dimesylate; bizelesin; bleomycin; bleomycin sulfate; bortezomib; brequinar sodium; bropirimine; busulfan; cactinomycin; calusterone; caracemide; carbetimer; carboplatin; carmustine; carubicin hydrochloride; carzelesin; capecitabine; cedefingol; cetuximab; chlorambucil; cirolemycin; cisplatin; cladribine; clofarabine; crisnatol mesylate; cyclophosphamide; cytarabine; dacarbazine; dasatinib; daunorubicin hydrochloride; dactinomycin; darbepoetin alfa; decitabine; degarelix; denileukin diftitox; dexormaplatin; dexrazoxane hydrochloride; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; eltrombopag olamine; enloplatin; enpromate; epipropidine; epirubicin hydrochloride; epoetin alfa; erbulozole; erlotinib hydrochloride; esorubicin hydrochloride; estramustine; estramustine phosphate sodium; etanidazole; etoposide; etoposide phosphate; etoprine; everolimus; exemestane; fadrozole hydrochloride; fazarabine; fenretinide; filgrastim; floxuridine; fludarabine phosphate; fluorouracil; fluorocitabine; fosquidone; fostriecin sodium; fulvestrant; gefitinib; gemcitabine; gemcitabine hydrochloride; gemcitabine-cisplatin; gemtuzumab ozogamicin; goserelin acetate; histrelin acetate; hydroxyurea; idarubicin hydrochloride; ifosfamide; iimofosine; ibritumomab tiuxetan; idarubicin; ifosfamide; imatinib mesylate; imiquimod; interleukin II (including recombinant interleukin II, or rIL2), interferon alfa-2a; interferon alfa-2b; interferon alfa-n1; interferon alfa-n3; interferon beta-1a; interferon gamma-1b; iproplatin; irinotecan hydrochloride; ixabepilone; lanreotide acetate; lapatinib; lenalidomide; letrozole; leuprolide acetate; leucovorin calcium; leuprolide acetate; levamisole; liposomal cytarabine; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; methoxsalen; metoprine; meturedepa; mitindomide; mitocarcin; mitocromin; mitogillin; mitomalcin; mitomycin C; mitosper; mitotane; mitoxantrone hydrochloride; mycophenolic acid; nandrolone phenpropionate; nelarabine; nilotinib; nocodazoie; nofetumomab; nogalamycin; ofatumumab; oprelvekin; ormaplatin; oxaliplatin; oxisuran; paclitaxel; palifermin; palonosetron hydrochloride; pamidronate; pegfilgrastim; pemetrexed disodium; pentostatin; panitumumab; pazopanib hydrochloride; pemetrexed disodium; plerixafor; pralatrexate; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; quinacrine; raloxifene hydrochloride; rasburicase; recombinant HPV bivalent vaccine; recombinant HPV quadrivalent vaccine; riboprine; rogletimide; rituximab; romidepsin; romiplostim; safingol; safingol hydrochloride; sargramostim; semustine; simtrazene; sipuleucel-T; sorafenib; sparfosate sodium; sparsomycin; spirogermanium hydrochloride; spiromustine; spiroplatin; streptonigrin; streptozocin; sulofenur; sunitinib malate; talisomycin; tamoxifen citrate; tecogalan sodium; tegafur; teloxantrone hydrochloride; temozolomide; temoporfin; temsirolimus; teniposide; teroxirone; testolactone; thalidomide; thiamiprine; thioguanine; thiotepa; tiazofurin; tirapazamine; topotecan hydrochloride; toremifene; tositumomab and I 131 Iodine tositumomab; trastuzumab; trestolone acetate; tretinoin; triciribine phosphate; trimetrexate; trimetrexate glucuronate; triptorelin; tubulozole hydrochloride; uracil mustard; uredepa; valrubicin; vapreotide; verteporfin; vinblastine; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorinostat; vorozole; zeniplatin; zinostatin; zoledronic acid; and zorubicin hydrochloride.

In some embodiments, a compound of Formula (I), or a pharmaceutically acceptable salt thereof, is used in combination with anti-emetic agents to treat nausea or emesis, which result from the use of a compound of Formula (I), anti-cancer agent(s) and/or radiation therapy.

In some embodiments, a compound of Formula (I), or a pharmaceutically acceptable salt thereof, is used in combination with an agent useful in the treatment of anemia or neutropenia.

In some embodiments, a compound of Formula (I), or a pharmaceutically acceptable salt thereof, is administered with corticosteroids.

In some embodiments, a compound of Formula (I), or a pharmaceutically acceptable salt thereof, is coadministered with analgesics.

In some embodiments, a compound of Formula (I), or a pharmaceutically acceptable salt thereof, is used in combination with radiation therapy (or radiotherapy). Radiation therapy is the treatment of cancer and other diseases with ionizing radiation. Radiation therapy is optionally used to treat localized solid tumors, such as cancers of the skin, tongue, larynx, brain, breast, prostate, colon, uterus and/or cervix. It is also optionally used to treat leukemia and lymphoma (cancers of the blood-forming cells and lymphatic system, respectively).

A technique for delivering radiation to cancer cells is to place radioactive implants directly in a tumor or body cavity. This is called internal radiotherapy (brachytherapy, interstitial irradiation, and intracavitary irradiation are types of internal radiotherapy.) Using internal radiotherapy, the radiation dose is concentrated in a small area, and the patient stays in the hospital for a few days. Internal radiotherapy is frequently used for cancers of the tongue, uterus, prostate, colon, and cervix. The term "radiotherapy" or "ionizing radiation" include all forms of radiation, including but not limited to α, β, and γ radiation and ultraviolet light.

EXAMPLES

These examples are provided for illustrative purposes only and not to limit the scope of the claims provided herein.

Example 1

Preparation of 5-Bromo-1-(tetrahydro-2H-pyran-2-yl)-1H-indazole (Intermediate 1)

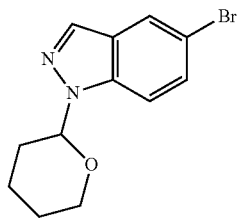

A 250-mL round-bottom flask equipped with a magnetic stir bar, a rubber septum, and a N$_2$ inlet was charged with 5-bromo-1H-indazole (10 g, 50.7 mmol) and anhydrous DCM (101 mL). To this solution, DHP (23 mL, 253.8 mmol) was added in one portion at room temperature followed by addition of PPTS (1.28 g, 5 mmol). The resulting mixture was stirred at room temperature for 48 h. Upon completion by TLC, the reaction mixture was quenched with water and extracted with DCM (3×100 mL). The combined organic extracts were washed with water (100 mL), washed with brine (50 mL), dried over sodium sulfate, filtered, concentrated, and purified by silica gel chromatography (0-10% ethyl acetate in hexanes) to give the title compound (13 g) as a pale yellow oil. $^1$H NMR (300 MHz, DMSO-d$_6$): δ 8.10 (s, 1H), 8.02 (d, 1H), 7.73 (d, 1H), 7.53 (dd, 1H), 5.86 (dd, 1H), 3.89-3.85 (m, 1H), 3.73-3.69 (m, 1H), 2.43-2.31 (m, 1H), 2.06-1.92 (m, 2H), 1.80-1.64 (m, 1H), 1.60-150 (m, 2H).

Example 2

Preparation of 5-Ethynyl-1-(tetrahydro-2H-pyran-2-yl)-1H-indazole (Intermediate 2)

Step 1: 1-(Tetrahydro-2H-pyran-2-yl)-5-((trimethylsilyl)ethynyl)-1H-indazole

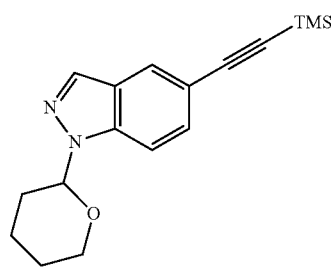

To a 250-mL pressure tube, 5-bromo-1-(tetrahydro-2H-pyran-2-yl)-1H-indazole (11.9 g, 42.3 mmol; Intermediate 1), Pd(Ph$_3$P)$_2$Cl$_2$ (1.48 g, 0.05 mmol), CuI (0.8 g, 4.2 mmol) and THF/triethylamine (5:1, 85 mL) were added. This mixture was degassed with three vacuum/N$_2$ cycles, and then trimethylsilylacetylene (9 mL, 63.5 mmol) was added. The pressure tube was sealed and heated at 80° C. for 2 days. Upon completion by LCMS, the reaction mixture was cooled down to room temperature and filtered through Celite with ethyl acetate (200 mL). The filtrate was concentrated to give the crude product that was used directly in the next step. LCMS: 299 (M+H)$^+$.

Note: For this compound and other compounds synthesized using this reaction, alternate procedures have been employed using an amine, such as triethylamine or pyrrolidine, as the sole solvent.

Step 2: 5-Ethynyl-1-(tetrahydro-2,1-pyran-2-yl)-1H-indazole

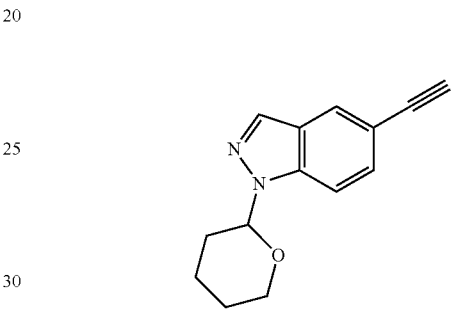

A 250-mL round-bottom flask equipped with a magnetic stir bar, a rubber septum, and a N$_2$ inlet was charged with a solution of 1-(tetrahydro-2H-pyran-2-yl)-5-((trimethylsilypethynyl)-1H-indazole (12.6 g, 42.2 mmol) in MeOH. To this solution, solid K$_2$CO$_3$ (0.58 g, 4.2 mmol) was added in one portion. The resulting mixture was stirred at room temperature for 4 h. Upon completion by TLC, the reaction mixture was filtered, concentrated, and purified by silica gel chromatography (0-10% ethyl acetate in hexanes) to give the title compound (4.7 g) as a pale yellow solid. $^1$H NMR (300 MHz, DMSO-d$_6$): δ 8.13 (s, 1H), 7.96 (s, 1H), 7.75 (d, 1H), 7.47 (dd, 1H), 5.86 (dd, 1H), 4.10 (s, 1H), 3.90-3.86 (m, 1H), 3.78-3.68 (m, 1H), 2.43-2.32 (m, 1H), 2.06-1.93 (m, 2H), 1.81-1.66 (m, 1H), 1.60-1.50 (m, 2H).

Example 3

Preparation of 5-(But-1-yn-1-yl)-1-(tetrahydro-2H-pyran-2-yl)-1H-indazole (Intermediate 3)

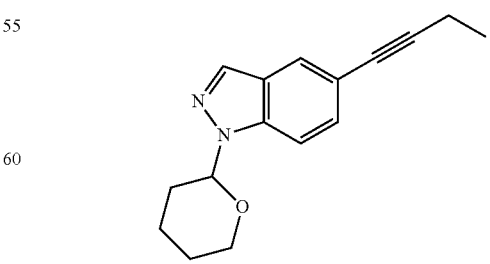

A 250-mL round-bottom flask equipped with a magnetic stir bar, a rubber septum, and a N$_2$ inlet was charged with 5-ethynyl-1-(tetrahydro-2H-pyran-2-yl)-1H-indazole (4.2 g, 18.6 mmol; Intermediate 2) and anhydrous THF/TMEDA (9:1, 93 mL). This solution was cooled to −78° C. in an IPA/dry ice bath, and n-BuLi (17.4 mL solution in hexanes, 27.84 mmol) was added dropwise over 15 minutes. The resulting mixture was stirred for 30 minutes at −78° C., and then iodoethane (2.23 mL, 27.84 mmol) was added dropwise over 5 minutes. The mixture was gradually warmed to room temperature, stirred for 1 h, and then heated at 40° C. overnight. Upon completion by LCMS, the reaction mixture was cooled to room temperature, quenched with water (100 mL), and extracted with ethyl acetate (2×100 mL). The combined organics were washed with water (100 mL), washed with brine (50 mL), dried over sodium sulfate, filtered, concentrated, and purified by silica gel chromatography (0-10% ethyl acetate in hexanes) to give the title compound (1.42 g) as a pale yellow solid. $^1$H NMR (300 MHz, DMSO-$d_6$): δ 8.08 (s, 1H), 7.82 (s, 1H), 7.69 (d, 1H), 7.39 (d, 1H), 5.84 (dd, 1H), 3.89-3.86 (m, 1H), 3.76-3.72 (m, 1H), 2.45-2.36 (m, 3H), 2.04-1.94 (m, 2H), 1.74 (m, 1H), 1.57-1.20 (m, 2H), 1.16 (t, 3H); LCMS: 255 (M+H)$^+$.

Note: For this compound and other compounds prepared using this reaction, lithium bis(trimethylsilyl)amide has been employed as the base in THF at 0° C. followed by alkylation with alkyl-halide at reflux.

The Intermediates in Table 2 were prepared from known or commercial starting materials following the procedures outlined for Intermediates 1-3.

TABLE 2

| Intermediate 4 | 1-(Tetrahydro-2H-pyran-2-yl)-5-(4,4,4-trideuterobut-1-yn-1-yl)-1H-indazole | 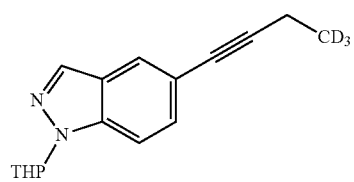 |
| --- | --- | --- |
| Intermediate 5 | 5-(But-1-yn-1-yl)-7-chloro-1-(tetrahydro-2H-pyran-2-yl)-1H-indazole | 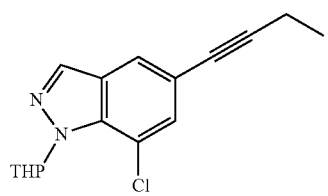 |
| Intermediate 6 | 5-(But-1-yn-1-yl)-7-methyl-1-(tetrahydro-2H-pyran-2-yl)-1H-indazole | 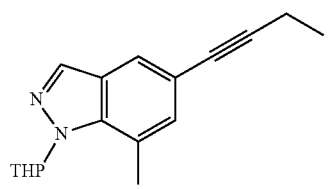 |
| Intermediate 7 | 5-(But-1-yn-1-yl)-3-methyl-1-(tetrahydro-2H-pyran-2-yl)-1H-indazole | 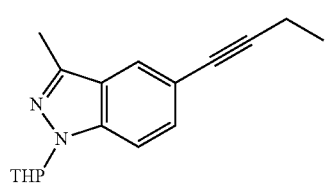 |
| Intermediate 8 | 5-(But-1-yn-1-yl)-3-chloro-1-(tetrahydro-2H-pyran-2-yl)-1H-indazole | 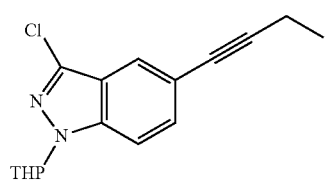 |
| Intermediate 9 | 5-(Prop-1-yn-1-yl)-1-(tetrahydro-2H-pyran-2-yl)-1H-indazole | 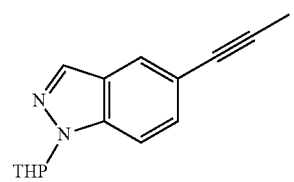 |

TABLE 2-continued

| Intermediate 10 | 5-(Pent-1-yn-1-yl)-1-(tetrahydro-2H-pyran-2-yl)-1H-indazole | 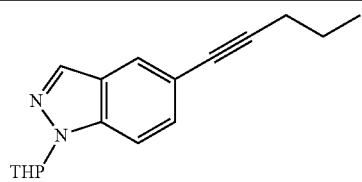 |
| Intermediate 11 | 5-(Perdeuterobut-1-yn-1-yl)-1-(tetrahydro-2H-pyran-2-yl)-1H-indazole | 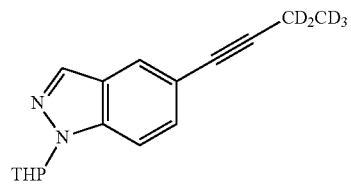 |

Example 4

Preparation of 5-(But-1-yn-1-yl)-4-methyl-1-(tetrahydro-2H-pyran-2-yl)-1H-indazole (Intermediate 12)

Step 1: 4-Methyl-1-(tetrahydro-2H-pyran-2-yl)-5-((trimethylsilyl)ethynyl)-1H-indazole

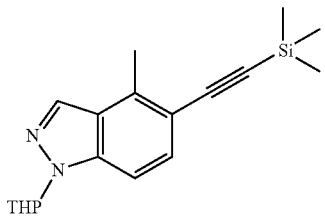

A mixture of 5-bromo-4-methyl-1-(tetrahydro-2H-pyran-2-yl)-1H-indazole (915 mg, 3.10 mmol; prepared from 5-bromo-4-methyl-1H-indazole following the procedure outlined for Intermediate 1), copper iodide (72 mg, 0.38 mmol), sodium tetrachloropalladate (55 mg, 0.19 mmol), 2-(di-tert-butylphosphino) -1-phenyl-1H-indole (128 mg, 0.379 mmol), and TMEDA:H$_2$O (9:1, 10 mL) was degassed with three vacuum/nitrogen cycles. Ethynyltrimethylsilane was added to the reaction, and the mixture was heated at 80° C. for 90 min and then cooled to room temperature. The reaction mixture was filtered through Celite and the Celite was washed with ethyl acetate (100 mL). The filtrate was washed (2×50 mL sat'd NaHCO$_3$), dried (Na$_2$SO$_4$), and concentrated under reduced pressure. The crude material was purified on a silica gel column to yield the desired compound. $^1$H NMR (300 MHz, DMSO-d$_6$): δ 8.24 (s, 1H), 7.54 (d, 1H), 7.39 (d, 1H), 5.82 (dd, 1H), 3.88 (m, 1H), 3.71 (m, 1H), 2.63 (s, 3H), 2.39 (m, 1H), 2.00 (m, 2H), 1.72 (m, 1H), 1.58 (m, 2H), 0.24 (s, 9H); LCMS: 313 (M+H)$^+$.

Step 2: 5-(But-1-yn-1-yl)-4-methyl-1-(tetrahydro-2H-pyran-2-yl)-1H-indazole

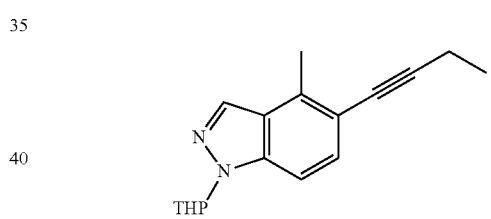

The title compound was prepared from 4-methyl-1-(tetrahydro-2H-pyran-2-yl)-5-((trimethylsilypethynyl)-1H-indazole following the procedures outlined for Intermediate 2 (step 2) and Intermediate 3. $^1$H NMR (300 MHz, DMSO-d$_6$): δ 7.97 (s, 1H), 7.27 (d, 1H), 7.11 (d, 1H), 5.59 (dd, 1H), 3.58 (m, 1H), 3.50 (m, 1H), 2.38 (s, 3H), 2.17 (q, 2H), 2.13 (m, 1H), 1.77 (m, 2H), 1.50 (m, 1H), 1.36 (m, 2H), 0.98 (t, 3H).

The Intermediate in Table 3 was prepared from 5-bromo-6-methyl-1H-indazole following the procedures outlined for Intermediate 12.

TABLE 3

| Intermediate 13 | 5-(But-1-yn-1-yl)-6-methyl-1-(tetrahydro-2H-pyran-2-yl)-1H-indazole | 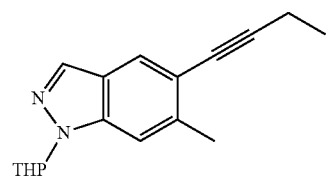 |

Example 5

Preparation of 5-(Cyclopropylethynyl)-1-(tetrahydro-2H-pyran-2-yl)-1H-indazole (Intermediate 14)

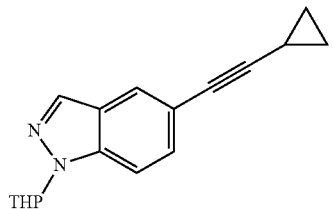

A 1 L three-necked round bottom flask was charged with 5-bromo-1-(tetrahydro-2H-pyran-2-yl)-1H-indazole (31.2 g, 111 mmol; Intermediate 1) and triethylamine (500 mL). The flask was degassed with three vacuum/$N_2$ cycles, followed by the addition of Pd(PPh$_3$)$_2$Cl$_2$ (7.7 g, 11 mmol) and CuI (2.1 g, 11 mmol) under $N_2$ atmosphere. The flask was again degassed with three vacuum/$N_2$ cycles. Ethynylcyclopropane (70% in toluene, 20.9 g, 222 mmol) was then added via syringe and the reaction mixture was stirred at 80° C. for 16 hours. Upon completion, the solvent was evaporated. The residue was diluted with dichloromethane (600 mL), washed with water (2×200 mL) and brine (200 mL), dried over anhydrous sodium sulfate, and concentrated in vacuo. The residue was further purified on silica gel column (1:100-1:20 EtOAc/petroleum ether) affording the title compound (27.0 g). $^1$H NMR (400 MHz, DMSO-d$_6$): δ 8.09 (s, 1H), 7.82 (s, 1H), 7.70 (d, 1H), 7.39 (m, 1H), 5.84 (dd, 1H), 3.91-3.87 (m, 1H), 3.78-3.73 (m, 1H), 2.52-2.37 (m, 1H), 2.05-1.94 (m, 2H), 1.76-1.72 (m, 1H), 1.60-1.52 (m, 3H), 0.92-0.87 (m, 2H), 0.78-0.73 (m, 2H); LCMS: 267 (M+H)$^+$.

Example 6

Preparation of 5-(4-Methylpent-1-yn-1-yl)-1-(tetrahydro-2H-pyran-2-yl)-1H-indazole (Intermediate 15)

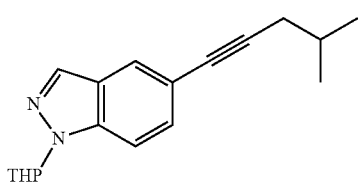

To a mixture of 5-bromo-1-(tetrahydro-2H-pyran-2-yl)-1H-indazole (3.0 g, 10.7 mmol; Intermediate 1), Pd(PPh$_3$)$_2$Cl$_2$ (1.03 g, 1.07 mmol) and CuI (203 mg, 1.07 mmol) in triethylamine (30 mL), was added 4-methylpent-1-yne (2.23 g, 27.8 mmol) under $N_2$ atmosphere. The resulting mixture was stirred at 80° C. for 16 hours under $N_2$ atmosphere. Upon completion, the reaction mixture was diluted with EtOAc and filtered. The filtrate was washed with water (3×10 mL), dried over Na$_2$SO$_4$ and concentrated in vacuo. The residue was purified by column chromatography on silica gel (0~10% EtOAc in petroleum ether) affording the title compound (2.2 g) as yellow solid. $^1$H NMR (400 MHz, DMSO-d$_6$): δ 8.09 (s, 1H), 7.84 (s, 1H), 7.69 (d, 1H), 7.39 (dd, 1H), 5.83 (dd, 1H), 3.90-3.86 (m, 1H), 3.77-3.73 (m, 1H), 2.42-2.32 (m, 1H), 2.33 (d, 2H), 2.05-1.94 (m, 2H), 1.86 (m, 1H), 1.76-1.71 (m, 1H), 1.60-1.54 (m, 2H), 1.02 (d, 6H); LCMS: 283 (M+H)$^+$.

Example 7

Preparation of 3-(1-(Tetrahydro-2H-pyran-2-yl)-1H-indazol-5-yl)prop-2-yn-1-ol (Intermediate 16)

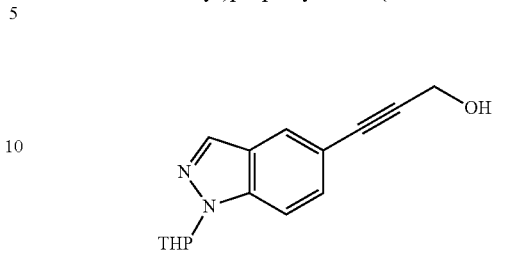

A 500 mL three-necked round bottom flask was charged with 5-bromo-1-(tetrahydro-2H-pyran-2-yl)-1H-indazole (14.0 g, 50 mmol; Intermediate 1) and triethylamine (300 mL). The flask was degassed with 3 cycles of vacuum/$N_2$, followed by the addition of Pd(PPh$_3$)$_2$Cl$_2$ (3.5 g, 5 mmol) and CuI (0.95 g, 5 mmol) under $N_2$ atmosphere. The flask was again degassed with 3 cycles of vacuum/$N_2$. Prop-2-yn-1-ol (8.4 g, 150 mmol) was added via syringe and the reaction mixture was stirred at 80° C. for 16 hours. Upon completion, the solvent was evaporated. The residue was diluted with dichloromethane (400 mL), washed with water (3×200 mL) and brine (200 mL), dried over anhydrous sodium sulfate, and concentrated in vacuo. The residue was further purified on silica gel column (1:100-1:20 EtOAc/petroleum ether) affording the title compound (11.1 g). $^1$H NMR (400 MHz, DMSO-d$_6$): δ 8.13 (s, 1H), 7.90 (s, 1H), 7.75 (d, 1H), 7.44 (d, 1H), 5.86 (dd, 1H), 5.33 (t, 1H), 4.33 (d, 2H), 3.89-3.86 (m, 1H), 3.79-3.73 (m, 1H), 2.45-2.35 (m, 1H), 2.05-1.95 (m, 2H), 1.80-1.70 (m, 1H), 1.60-1.56 (m, 2H); LCMS: 257 (M+H)$^+$.

Example 8

Preparation of: 4-(1-(Tetrahydro-2H-pyran-2-yl)-1H-indazol-5-yl)but-3-yn-1-ol (Intermediate 17)

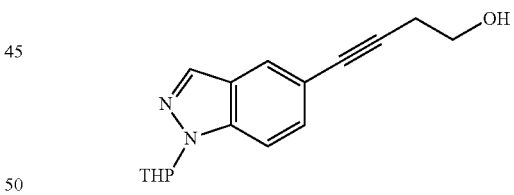

To a mixture of 5-bromo-1-(tetrahydro-2H-pyran-2-yl)-1H-indazole (17.0 g, 60.7 mmol; Intermediate 1), Pd(PPh$_3$)$_2$Cl$_2$ (5.80 g, 6.07 mmol), CuI (1.20 g, 6.07 mmol), and triethylamine (170 mL) was added but-3-yn-1-ol (6.80 g, 97.2 mmol) under $N_2$ atmosphere. The resulting mixture was stirred at 80° C. for 16 hours under $N_2$ atmosphere. Upon completion, the reaction mixture was diluted with EtOAc and washed with water (3×50 mL). The organic layer was dried over Na$_2$SO$_4$ and concentrated in vacuo. The residue was purified by column chromatography on silica gel (30-50% EtOAc in petroleum ether) affording the title compound (8.0 g). $^1$H NMR (400 MHz, DMSO-d$_6$): δ 8.09 (s, 1H), 7.83 (s, 1H), 7.70 (d, 1H), 7.40 (d, 1H), 5.84 (dd, 1H), 4.90 (br, 1H), 3.91-3.87 (m, 1H), 3.77-3.70 (m, 1H), 3.60 (t, 2H), 2.56 (t, 2H), 2.48-2.33 (m, 1H), 2.04-1.94 (m, 2H), 1.76-1.69 (m, 1H), 1.60-1.55 (m, 2H); LCMS: 271 (M+H)$^+$.

Example 9

Preparation of 5-Bromo-4-fluoro-1-(tetrahydro-2H-pyran-2-yl)-1H-indazole (Intermediate 18)

Step 1: 4-Bromo-3-fluoro-2-methylaniline

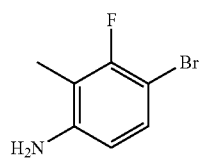

To a solution of 3-fluoro-2-methylaniline (20 g, 0.16 mol) in CH$_3$CN (500 mL) was added NBS (31.3 g, 0.176 mol) in portions at 10° C. The resulting mixture was stirred at room temperature for 30 minutes. Upon completion, saturated Na$_2$S$_2$O$_3$ (500 mL) was added slowly into the reaction mixture at 10° C. The organic layer was separated, and the aqueous layer was extracted with EtOAc. The combined organic layers were dried over Na$_2$SO$_4$ and concentrated in vacuo. The residue was washed with petroleum ether affording the title compound (20 g), which was used in the next step without further purification. $^1$H NMR (300 MHz, DMSO-d$_6$): δ 7.08 (t, 1H), 6.40 (dd, 1H), 5.35 (br, 2H), 1.98 (d, 3H).

Step 2: 5-Bromo-4-fluoro-1H-indazole

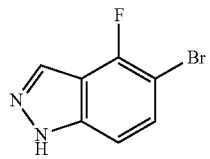

To a solution of 4-bromo-3-fluoro-2-methylaniline (20 g, 98.0 mmol) in CH$_3$CO$_2$H (600 mL) was added NaNO$_2$ (8.1 g, 118 mmol) at 10° C. The resulting mixture was stirred at room temperature for 4 hours. Upon completion, aqueous NaOH (50%) was added to the reaction mixture until pH was ~7-8. The mixture was extracted with EtOAc. The organic layer was dried over Na$_2$SO$_4$ and concentrated in vacuo. The residue was purified by column chromatography on silica gel (0~40% EtOAc in petroleum ether) affording the title compound (16 g). $^1$H NMR (300 MHz, DMSO-d$_6$): δ 13.58 (br, 1H), 8.22 (s, 1H), 7.53 (t, 1H), 7.38 (d, 1H).

Step 3: 5-Bromo-4-fluoro-1-(tetrahydro-2H-pyran-2-yl)-1H-indazole

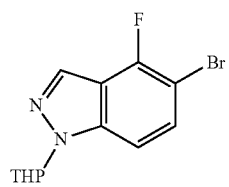

To a mixture of 5-bromo-4-fluoro-1H-indazole (50 g, 0.23 mol) and DHP (23 g, 0.28 mol) in dry dichloromethane (1000 mL) was added PTSA (2.2 g, 11.5 mmol) at room temperature. The resulting mixture was stirred overnight at that temperature. Upon completion, saturated aqueous NaHCO$_3$ (100 mL) was added slowly into the reaction mixture. The organic layer was separated, dried over Na$_2$SO$_4$, and concentrated in vacuo. The residue was purified by column chromatography on silica gel (0~2% EtOAc in petroleum ether) and then re-crystallized from petroleum ether to afford the title compound (55 g). $^1$H NMR (300 MHz, DMSO-d$_6$,): δ 8.28 (s, 1H), 7.58-7.66 (m, 2H), 5.89 (dd, 1H), 3.90-3.85 (m, 1H), 3.79-3.70 (m, 1H), 2.42-2.29 (m, 1H), 2.06-1.94 (m, 2H), 1.77-1.68 (m, 1H), 1.60-1.53 (m, 2H); LCMS: 299 (M+H)$^+$.

Example 10

Preparation of 5-(Cyclopropylethynyl)-4-fluoro-1-(tetrahydro-2H-pyran-2-yl)-1H-indazole (Intermediate 19)

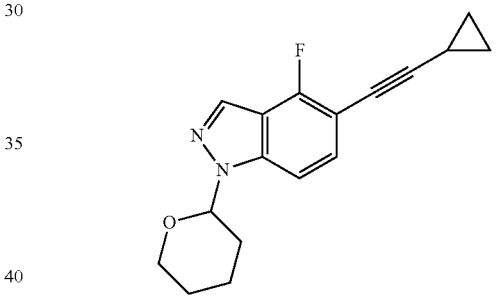

In a high pressure tube, a mixture of 5-bromo-4-fluoro-1-(tetrahydro-2H-pyran-2-yl)-1H-indazole (8.0 g, 26.8 mmol; Intermediate 18), PdCl$_2$(PPh$_3$)$_2$ (3.7 g, 5.35 mmol), CuI (1.0 g, 5.35 mmol), and triethylamine (30 mL) was deoxygenated with three cycles of vacuum/nitrogen. Ethynylcyclopropane (8.9 g, 134 mmol) was added under N$_2$ atmosphere. The tube was sealed and the reaction mixture was heated at 120° C. for 63 hours. Upon completion, the reaction mixture was diluted with ethyl acetate and filtered through Celite. The filtrate was concentrated in vacuo and the residue was purified by column chromatography on silica gel (0~10% ethyl acetate in petroleum ether) affording the title compound (4.3 g). $^1$H NMR (400 MHz, DMSO-d$_6$): δ 8.25 (s, 1H), 7.55 (d, 1H), 7.40 (dd, 1H), 5.88 (dd, 1H), 3.88-3.85 (m, 1H), 3.76-3.73 (m, 2H), 2.43-2.33 (m, 1H), 2.05-1.95 (m, 2H), 1.76-1.72 (m, 1H), 1.62-1.56 (m, 3H), 0.93-0.89 (m, 2H), 0.79-0.74 (m, 2H); LCMS: 285 (M+H)$^+$.

The Intermediates in Table 4 were prepared from Intermediate 1 following the procedures outlined for Intermediates 14-17, and 19.

TABLE 4

| Intermediate 20 | 5-(Cyclopentylethynyl)-1-(tetrahydro-2H-pyran-2-yl)-1H-indazole | 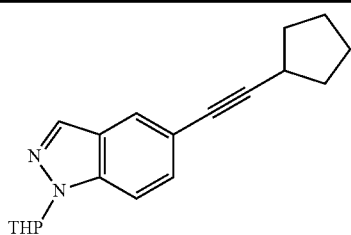 |
| Intermediate 21 | 5-(Cyclohexylethynyl)-1-(tetrahydro-2H-pyran-2-yl)-1H-indazole | 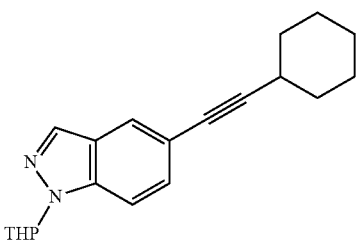 |
| Intermediate 22 | 5-(3-Methylbut-1-yn-1-yl)-1-(tetrahydro-2H-pyran-2-yl)-1H-indazole | 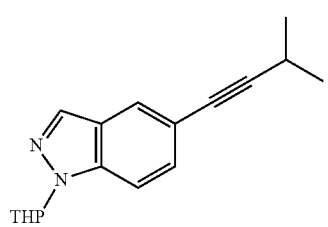 |
| Intermediate 23 | 5-(Hex-1-yn-1-yl)-1-(tetrahydro-2H-pyran-2-yl)-1H-indazole | 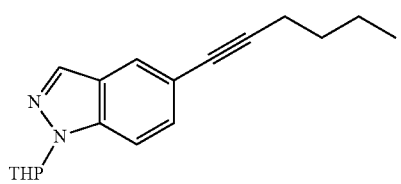 |
| Intermediate 24 | 5-(3-Cyclopentylprop-1-yn-1-yl)-1-(tetrahydro-2H-pyran-2-yl)-1H-indazole | 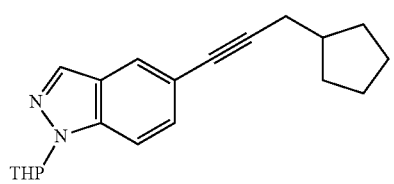 |

Example 11

Preparation of 5-(4-Chlorobut-1-yn-1-yl)-1-(tetrahydro-2H-pyran-2-yl)-1H-indazole (Intermediate 25)

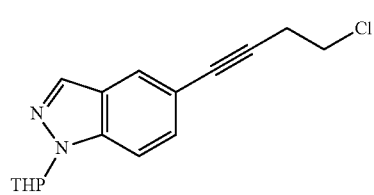

To a solution of 4-(1-(tetrahydro-2H-pyran-2-yl)-1H-indazol-5-yl)but-3-yn-1-ol (1.0 g, 3.7 mmol; Intermediate 17) in dry pyridine (10 mL) was added dropwise $POCl_3$ (2.4 g, 14.7 mmol) under $N_2$ atmosphere. The resulting solution was stirred at room temperature for 16 hours. Upon completion, the reaction mixture was concentrated in vacuo. The residue was poured into ice-water and extracted with EtOAc (2×10 mL). The combined organic layers were washed with brine, dried over $Na_2SO_4$ and concentrated in vacuo. The residue was further purified on silica gel column (0~20% EtOAc in petroleum ether) affording the title compound (400 mg). $^1$H NMR (400 MHz, DMSO-$d_6$): δ 8.11 (s, 1H), 7.86 (s, 1H), 7.72 (d, 1H), 7.42 (dd, 1H), 5.86 (dd, 1H), 3.90-3.86 (m, 1H), 3.81 (t, 2H), 3.77-3.70 (m, 1H), 2.93 (t, 2H), 2.41-2.34 (m, 1H), 2.05-1.94 (m, 2H), 1.75-1.71 (m, 1H), 1.60-1.55 (m, 2H); LCMS: 289 (M+H)$^+$.

Example 12

Preparation of 5-(3,3-Difluoroprop-1-yn-1-yl)-1-(tetrahydro-2,1-pyran-2-yl)-1H-indazole (Intermediate 26)

Step 1: 3-(1-(Tetrahydro-2H-pyran-2-yl)-1H-indazol-5-yl)propiolaldehyde

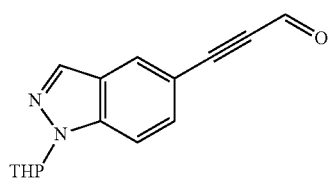

A 500 mL three-necked round bottom flask was charged with 3-(1-(tetrahydro-2H-pyran-2-yl)-1H-indazol-5-yl)prop-2-yn-1-ol (11.4 g, 44.2 mmol; Intermediate 16), dichloromethane (300 mL) and MnO$_2$ (38.4 g, 442 mmol). The resulting mixture was stirred at room temperature for 16 hours. Upon completion, the reaction mixture was filtered. The filtrate was dried over anhydrous sodium sulfate and concentrated in vacuo. The residue was purified by column chromatography on silica gel (1:100-1:20 EtOAc/petroleum ether) affording the title compound (6.4 g). $^1$H NMR (400 MHz, DMSO-d$_6$): δ 9.45 (s, 1H), 8.27-8.25 (m, 2H), 7.87 (d, 1H), 7.66 (dd, 1H), 5.86 (dd, 1H), 3.91-3.87 (m, 1H), 3.79-3.72 (m, 1H), 2.40-2.36 (m, 1H), 2.05-1.96 (m, 2H), 1.78-1.72 (m, 1H), 1.61-1.56 (m, 2H); LCMS: 255 (M+H)$^+$.

Step 2: 5-(3,3-Difluoroprop-1-yn-1-yl)-1-(tetrahydro-2H-pyran-2-yl)-1H-indazole

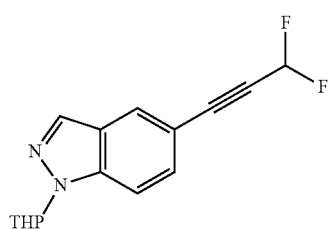

A 500 mL round bottom flask was charged with dry dichloromethane (200 mL), triethylamine.3HF (8.06 g, 50.1 mmol) and XtalFluor-E (8.61 g, 37.6 mmol) under N$_2$ atmosphere. The resulting solution was stirred at room temperature for 10 minutes. 3-(1-(Tetrahydro-2H-pyran-2-yl)-1H-indazol-5-yl)propiolaldehyde (3.21 g, 12.5 mmol) was added, and the mixture was stirred at room temperature for 1 hour. Upon completion, saturated NaHCO$_3$ (100 mL) was added into the mixture. The organic layer was separated, and the aqueous layer was extracted with dichloromethane (2×100 mL). The combined organic layers were dried over Na$_2$SO$_4$ and concentrated in vacuo. The residue was purified by column chromatography on silica gel (1:100-1:20 EtOAc/petroleum ether) affording the title compound (1.71 g). $^1$H NMR (400 MHz, DMSO-d$_6$): δ 8.20 (s, 1H), 8.14 (s, 1H), 7.83 (d, 1H), 7.58 (dd, 1H), 6.99 (t, 1H), 5.90 (dd, 1H), 3.90-3.87 (m, 1H), 3.79-3.73 (m, 1H), 2.45-2.37 (m, 1H), 2.05-1.96 (m, 2H), 1.79-1.65 (m, 1H), 1.60-1.56 (m, 2H); LCMS: 277 (M+H)$^+$.

Example 13

Preparation of 5-(4-Fluorobut-1-yn-1-yl)-1-(tetrahydro-2H-pyran-2-yl)-1H-indazole (Intermediate 27)

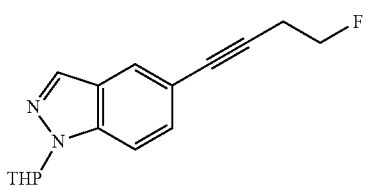

To a solution of 4-(1-(tetrahydro-2H-pyran-2-yl)-1H-indazol-5-yl)but-3-yn-1-ol (1.0 g, 3.7 mmol; Intermediate 17) in dry dichloromethane (25 mL), was added triethylamine.3HF (1.2 g, 7.4 mmol). XtalFluor-E (1.2 g, 5.5 mmol) was then added. The resulting solution was stirred at room temperature for 30 minutes. Upon completion, the reaction solution was neutralized by slow addition of saturated NaHCO$_3$ (10 mL). The organic layer was dried over Na$_2$SO$_4$ and concentrated in vacuo. The residue was purified by column chromatography on silica gel (0-20% EtOAc in petroleum ether) affording the title compound (100 mg). $^1$H NMR (400 MHz, DMSO-d$_6$): δ 8.12 (s, 1H), 7.88 (s, 1H), 7.73 (d, 1H), 7.42 (dd, 1H), 5.86 (dd, 1H), 4.60 (dt, 2H), 3.88 (m, 1H), 3.78-3.71 (m, 1H), 2.89 (dt, 2H), 2.48-2.34 (m, 1H), 2.06-1.95 (m, 2H), 1.78-1.72 (m, 1H), 1.58 (m, 2H); LCMS: 273 (M+H)$^+$.

Example 14

Preparation of 1-(Tetrahydro-2H-pyran-2-yl)-5-(3,3,3-trifluoroprop-1-yn-1-yl)-1H-indazole (Intermediate 28)

Step 1: 5-Iodo-1H-indazole

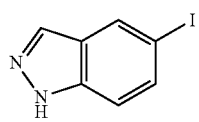

To a solution of 4-iodo-2-methylaniline (1.09 g, 4.68 mmol) in CH$_3$CO$_2$H (40 mL), were added NaNO$_2$ (0.39 g, 5.65 mmol) and water (1 mL) at 10° C. The resulting mixture was stirred at room temperature for 6 hours. Upon completion, the reaction mixture was extracted with EtOAc. The combined organic layers were dried over Na$_2$SO$_4$ and concentrated in vacuo. The residue was purified by column chromatography on silica gel (0~40% EtOAc in petroleum ether) affording the title compound (0.90 g). $^1$H NMR (DMSO-d$_6$, 400 MHz): δ 13.23 (br, 1H), 8.18 (s, 1H), 8.02 (s, 1H), 7.57 (d, 1H), 7.41 (d, 1H).

Step 2: 5-Iodo-1-(tetrahydro-2H-pyran-2-yl)-1H-indazole

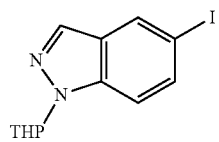

To a mixture of 5-iodo-1H-indazole (0.90 g, 3.69 mmol) and DHP (1.57 g, 18.7 mmol) in dry dichloromethane (20 mL), was added PTSA (0.08 g, 0.41 mmol) at room temperature. The resulting mixture was stirred overnight. Upon completion, saturated aqueous NaHCO₃ (30 mL) was added slowly into the reaction mixture. The organic layer was separated, dried over Na₂SO₄, and concentrated in vacuo. The residue was purified by column chromatography on silica gel (0-5% EtOAc in petroleum ether) affording the title compound (1.0 g). $^1$H NMR (400 MHz, DMSO-$d_6$): δ 8.21 (s, 1H), 8.08 (s, 1H), 7.67 (dd, 1H), 7.61 (d, 1H), 5.85 (dd, 1H), 3.88-3.85 (m, 1H), 3.78-3.72 (m, 1H), 2.41-2.29 (m, 1H), 2.05-1.95 (m, 2H), 1.77-1.72 (m, 1H), 1.61-1.56 (m, 2H).

Step 3: 1-(Tetrahydro-2H-pyran-2-yl)-5-(3,3,3-trifluoroprop-1-yn-1-yl)-1H-indazole

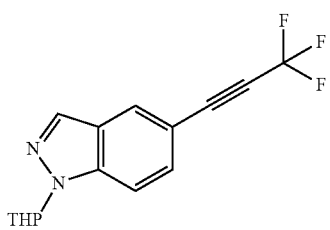

To a solution of LDA (2 M in THF, 3.2 mL, 6.4 mmol) in anhydrous THF (10 mL) was added dropwise 2-bromo-3,3,3-trifluoroprop-1-ene (0.55 g, 3.1 mmol) at −78° C. The resulting mixture was stirred at that temperature for 15 minutes, followed by the addition of ZnCl₂ (1 M in ethyl ether, 6.5 mL, 6.5 mmol) and TMEDA (1 mL, 6.5 mmol). The mixture was stirred at −78° C. for further 30 minutes and then 30 minutes at room temperature. 5-Iodo-1-(tetrahydro-2H-pyran-2-yl)-1H-indazole (0.99 g, 3.0 mmol) and Pd(PPh₃)₄ (0.21 g, 0.18 mmol) were added. The reaction mixture was heated at 80° C. for 6 hours under N₂ atmosphere. Upon completion, the reaction mixture was quenched with water (100 mL) and then diluted with ethyl acetate (300 mL). The organic layer was separated, dried over Na₂SO₄ and concentrated in vacuo. The residue was purified by column chromatography on silica gel (0~20% EtOAc in petroleum ether) affording the title compound (299 mg). $^1$H NMR (300 MHz, DMSO-$d_6$): δ 8.28 (s, 1H), 8.24 (s, 1H), 7.87 (d, 1H), 7.68 (dd, 1H), 5.91 (dd, 1H), 3.90-3.86 (m, 1H), 3.79-3.72 (m, 1H), 2.41-2.36 (m, 1H), 2.05-1.96 (m, 2H), 1.76-1.72 (m, 1H), 1.60-1.56 (m, 2H); LCMS: 295 (M+H)⁺.

Example 15

Preparation of 5-(4-Chlorobut-1-yn-1-yl)-4-fluoro-1-(tetrahydro-2H-pyran-2-yl)-1H-indazole (Intermediate 29)

Step 1: 4-(4-Fluoro-1-(tetrahydro-2H-pyran-2-yl)-1H-indazol-5-yl)but-3-yn-1-ol

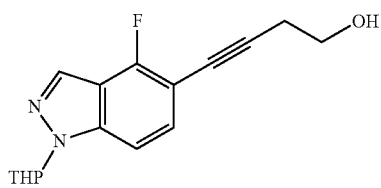

To a mixture of 5-bromo-4-fluoro-1-(tetrahydro-2H-pyran-2-yl)-1H-indazole (2.80 g, 9.36 mmol, Intermediate 18), Pd(PPh₃)₂Cl₂ (660 mg, 0.94 mmol), CuI (180 mg, 0.94 mmol), and triethylamine (50 mL) was added but-3-yn-1-ol (2.0 g, 28.1 mmol) under N₂ atmosphere. The resulting mixture was stirred at 60° C. for 16 hours. Upon completion, the reaction mixture was diluted with EtOAc, and washed with water (3×10 mL). The organic layer was dried over Na₂SO₄ and concentrated in vacuo. The residue was purified on silica gel column (0~20% EtOAc in petroleum ether) affording the title compound (2.0 g). $^1$H NMR (300 MHz, DMSO-$d_6$): δ 8.33 (s, 1H), 7.64 (d, 1H), 7.49 (dd, 1H), 5.94 (dd, 1H), 4.99 (t, 1H), 3.98-3.92 (m, 1H), 3.85-3.77 (m, 1H), 3.68 (t, 2H), 2.67 (t, 2H), 2.48-2.35 (m, 1H), 2.12-2.02 (m, 2H), 1.84-1.78 (m, 1H), 1.68-1.62 (m, 2H).

Step 2: 5-(4-Chlorobut-1-yn-1-yl)-4-fluoro-1-(tetrahydro-2H-pyran-2-yl)-1H-indazole

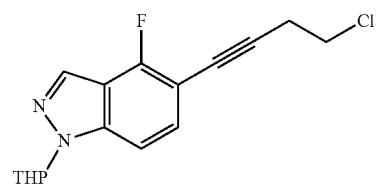

To a mixture of 4-(4-fluoro-1-(tetrahydro-2H-pyran-2-yl)-1H-indazol-5-yl)but-3-yn-1-ol (4.6 g, 16.0 mmol) in pyridine (50 mL), was added POCl₃ (10.3 g, 67.3 mmol). The resulting solution was stirred at room temperature for 2 hours. Upon completion, the reaction solution was poured into water (250 mL) and extracted with EtOAc. The organic layer was dried over Na₂SO₄ and concentrated in vacuo. The residue was purified on silica gel column (0~10% EtOAc in petroleum ether) affording the title compound (2.62 g). $^1$H NMR (300 MHz, DMSO-$d_6$): δ 8.13 (s, 1H), 7.58 (d, 1H), 7.43 (dd, 1H), 5.87 (dd, 1H), 3.90-3.69 (m, 2H), 3.83 (t, 2H), 2.98 (t, 1H), 2.41-2.29 (m, 1H), 2.06-1.94 (m, 2H), 1.78-1.70 (m, 1H), 1.60-1.54 (m, 2H); LCMS: 307 (M+H)⁺.

Example 16

Preparation of 4-Fluoro-5-(4-fluorobut-1-yn-1-yl)-1-(tetrahydro-2H-pyran-2-yl)-1H-indazole (Intermediate 30)

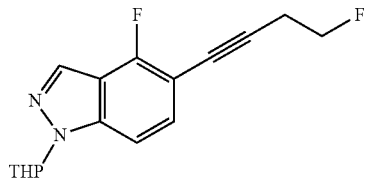

To a solution of 4-(4-fluoro-1-(tetrahydro-2H-pyran-2-yl)-1H-indazol-5-yl)but-3-yn-1-ol (3.4 g, 11.8 mmol; Intermediate 29, Step 1) in dry dichloromethane (100 mL), was added triethylamine.3HF (7.6 g, 47.2 mmol). XtalFluor-E (8.0 g, 34.9 mmol) was then added. The resulting solution was stirred at room temperature for 30 minutes. Upon completion, the reaction solution was neutralized by slow addition of saturated $NaHCO_3$ (30 mL). The organic layer was dried over $Na_2SO_4$ and concentrated in vacuo. The residue was purified by column chromatography on silica gel (0~20% EtOAc in petroleum ether), and then re-crystallized from petroleum ether to afford the title compound (1.3 g). $^1$H NMR (300 MHz, DMSO-$d_6$): δ 8.27 (s, 1H), 7.58 (d, 1H), 7.44 (dd, 1H), 5.89 (dd, 1H), 4.60 (dt, 2H), 3.91-3.85 (m, 1H), 3.80-3.69 (m, 1H), 2.93 (dt, 2H), 2.46-2.28 (m, 1H), 2.06-1.95 (m, 2H), 1.78-1.67 (m, 1H), 1.60-1.52 (m, 2H); LCMS: 291 (M+H)$^+$.

Example 17

Preparation of: 5-(3-Methoxyprop-1-yn-1-yl)-1-(tetrahydro-2H-pyran-2-yl)-1H-indazole (Intermediate 31)

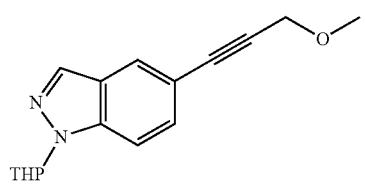

Sodium hydride (60% in mineral oil, 0.42 g, 10.5 mmol) was added to a solution of 3-(1-(tetrahydro-2H-pyran-2-yl)-1H-indazol-5-yl)prop-2-yn-1-ol (1.01 g, 3.94 mmol; Intermediate 16) in THF (20 mL) at 0° C. The mixture was stirred at 0° C. for 30 minutes, and then iodomethane (1.67 g, 11.8 mmol) was added. The resulting mixture was stirred at room temperature for 16 h. The reaction mixture was poured into ice water (100 mL) and extracted with EtOAc (3×100 mL). The combined organic layers were washed with brine (100 mL), dried over anhydrous sodium sulfate, and concentrated in vacuo. The residue was purified by column chromatography on silica gel (EtOAc/petroleum ether=1:30) to afford the title compound (0.714 g, yield 67.3%). $^1$H NMR (DMSO-$d_6$, 300 MHz): δ 8.21 (s, 1H), 7.93 (s, 1H), 7.73 (d, 1H), 7.47-7.45 (m, 1H), 5.85-5.83 (m, 1H), 4.38 (s, 2H), 3.76-3.71 (m, 2H), 3.35 (s, 3H), 2.40-2.37 (m, 1H), 2.03-1.94 (m, 2H), 1.73-1.72 (m, 1H), 1.57-1.55 (m, 2H). LCMS: 271 (M+H)$^+$.

The Intermediates in Table 5 were prepared from Intermediate 1 following the procedures outlined for Intermediates 16, 17 & 31.

TABLE 5

| Intermediate | Name | Structure |
|---|---|---|
| Intermediate 32 | 5-(4-Methoxybut-1-yn-1-yl)-1-(tetrahydro-2H-pyran-2-yl)-1H-indazole | 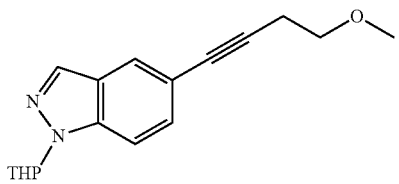 |
| Intermediate 33 | 5-(5-Methoxypent-1-yn-1-yl)-1-(tetrahydro-2H-pyran-2-yl)-1H-indazole | 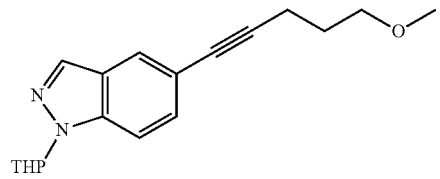 |
| Intermediate 34 | 5-(6-Methoxyhex-1-yn-1-yl)-1-(tetrahydro-2H-pyran-2-yl)-1H-indazole | 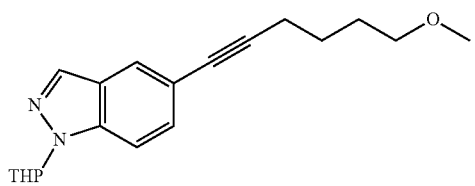 |

Example 18

Preparation of But-1-yn-1-yltrimethylsilane (Intermediate 35)

A 3 L three-necked round bottom flask was charged with (trimethylsilyl)acetylene (116 g, 1.19 mol) and dry THF (400 mL). The solution was cooled to −78° C. To this solution, butyllithium in hexane (2.5 M, 500 mL, 1.25 mol) was added dropwise over 2 hours. The resulting mixture was warmed to 0° C. for 10 minutes and then re-cooled to −78° C. HMPA (234 g, 1.31 mol) was added, and the mixture was stirred at −78° C. for 30 minutes. To this solution, iodoethane (200 g, 1.28 mol) was added. The reaction mixture was allowed to warm to room temperature and stirred overnight. Upon completion, the reaction mixture was washed with water (4×600 mL) and then brine (2×500 mL). The organic layer was dried over anhydrous sodium sulfate and filtered. Hexane and THF were distilled off at 75~110° C. But-1-yn-1-yltrimethylsilane was distilled between 125 to 135° C. affording 91 g of a colorless liquid (61%). $^1$H NMR (400 MHz, DMSO-d$_6$) δ 2.20 (q, 2H), 1.05 (t, 3H), 0.11 (s, 9H); $^{13}$C NMR (100 MHz, CDCl$_3$): δ 108.8, 83.3, 13.7, 13.4, 0.0.

Example 19

Alternate Preparation of Intermediate 3

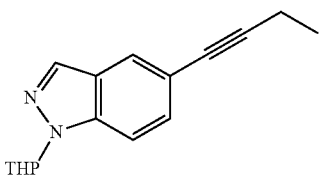

A mixture of 5-bromo-1-(tetrahydro-2H-pyran-2-yl)-1H-indazole (39.6 g, 0.142 mol; Intermediate 1), Cs$_2$CO$_3$ (60.0 g, 184 mmol), CuI (1.35 g, 7.08 mmol), Pd(OAc)$_2$ (1.59 g, 7.08 mmol), dppf (3.93 g, 7.08 mmol), and DMA (160 mL) was degassed with three vacuum/nitrogen cycles. But-1-yn-1-yltrimethylsilane (23.2 g, 184 mmol; Intermediate 35) was added, and the resulting mixture was heated at 80° C. for 5 h under N$_2$. Upon completion by LCMS, the reaction mixture was diluted with EtOAc (300 mL) and H$_2$O (300 mL) and then filtered. The organic layer of the filtrate was separated, and the aqueous layer was extracted with EtOAc (3×150 mL). The combined organic layers were washed with brine (2×100 mL), dried over anhydrous Na$_2$SO$_4$, filtered and concentrated. The residue was purified on silica gel column (300-400 mesh, 20 cm in diameter and 15 cm in height) using EtOAc/petroleum ether (1 L of petroleum ether; then 1 L of EtOAc/petroleum ether=1/50; and then EtOAc/Petroleum ether=1/30 until the by-product was washed out; then EtOAc/petroleum ether=1/10 to collect the product) affording a yellow oil (33 g) which solidified over time in the 4° C. refrigerator. The resulting solid was further washed with petroleum ether (200 mL, then 3×50 mL) affording the title compound as an off-white solid (26 g, 73%).

Example 20

Preparation of 5-(But-1-yn-1-yl)-4-fluoro-1-(tetrahydro-2,1-pyran-2-yl)-1H-indazole (Intermediate 36)

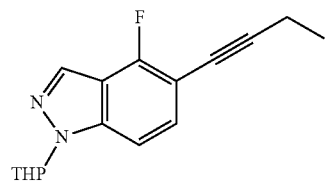

Nitrogen was bubbled into a solution of 5-bromo-4-fluoro-1-(tetrahydro-2H-pyran-2-yl)-1H-indazole (19.7 g, 65.9 mmol; Intermediate 18) and DMA (60 mL). After 5 min, CuI (1.25 g, 6.6 mmol), Pd(OAc)$_2$ (1.48 g, 6.6 mmol), dppf (3.66 g, 6.6 mmol), Cs$_2$CO$_3$ (34.3 g, 105.4 mmol), and but-1-yn-1-yltrimethylsilane (11.6 g, 92.3 mmol; Intermediate 35) were added sequentially with continued N$_2$ bubbling. The resulting mixture was heated at 80° C. for 18 h under N$_2$. The reaction mixture was diluted with EtOAc (900 mL) and H$_2$O (500 mL) and then filtered. The organic layer of the filtrate was separated, and the aqueous layer was extracted with EtOAc (2×100 mL). The combined organic layers were washed with brine (3×100 mL), dried over anhydrous Na$_2$SO$_4$, concentrated, and purified by silica gel chromatography (1:30 EtOAc/petroleum ether) to give the title compound (15.2 g) as a white solid. $^1$H NMR (DMSO-d$_6$, 400 MHz): δ 8.26 (s, 1H), 7.57 (d, 1H), 7.42 (dd, 1H), 5.87 (dd, 1H), 3.90-3.86 (m, 1H), 3.78-3.71 (m, 1H), 2.48 (q, 2H), 2.40-2.30 (m, 1H), 2.05-1.95 (m, 2H), 1.77-1.71 (m, 1H), 1.59-1.57 (m, 2H), 1.19 (t, 3H); LCMS: 273 (M+H)$^+$.

Example 21

Preparation of 5-(But-1-yn-1-yl)-4-chloro-1-(tetrahydro-2H-pyran-2-yl)-1H-indazole (Intermediate 37)

Step 1: 4-Bromo-3-chloro-2-methylaniline

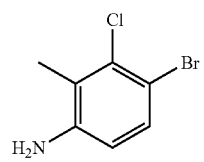

To a solution of 3-chloro-2-methylaniline (30 g, 0.212 mol) in CH$_3$CN (300 mL) was added NBS (45.2 g, 0.254 mol) in portions at 10° C. The resulting mixture was stirred at room temperature for 30 minutes. Upon completion, saturated Na$_2$S$_2$O$_3$ (500 mL) was added slowly into the reaction mixture at 10° C. The organic layer was separated, and the aqueous layer was extracted with EtOAc. The combined organic layers were dried over Na$_2$SO$_4$ and concentrated in vacuo. The residue was washed with petroleum ether to afford the title compound (30 g), which was used in the next step without further purification. ¹H NMR (300 MHz, CDCl₃): δ 7.24 (d, 1H), 6.48 (d, 1H), 3.70 (br, 2H), 2.28 (s, 3H).

Step 2: 5-Bromo-4-chloro-1H-indazole

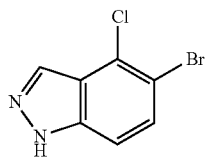

To a solution of 4-bromo-3-chloro-2-methylaniline (11 g, 49.9 mmol) in CH₃CO₂H (450 mL) was added NaNO₂ (5.4 g, 78.3 mmol) in H₂O (15 mL) at 10° C. The resulting mixture was stirred at room temperature for 30 minutes. Upon completion, the reaction mixture was diluted with H₂O (500 mL) and extracted with EtOAc. The organic layer was dried over Na₂SO₄ and concentrated in vacuo. The residue was triturated with petroleum ether affording the title compound (4.5 g) as yellow solid. ¹H NMR (400 MHz, DMSO-d₆): δ 13.60 (s, 1H), 8.15 (s, 1H), 7.62 (d, 1H), 7.52 (d, 1H).

Step 3: 5-Bromo-4-chloro-1-(tetrahydro-2H-pyran-2-yl)-1H-indazole

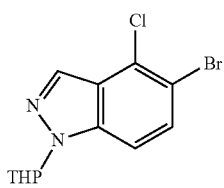

To a mixture of 5-bromo-4-chloro-1H-indazole (8.0 g, 34.6 mmol) and DHP (8.72 g, 0.104 mol) in dry dichloromethane (200 mL) was added PTSA (0.657 g, 3.46 mmol) at room temperature. The resulting mixture was stirred at room temperature overnight. Upon completion, saturated aqueous NaHCO₃ (100 mL) was added slowly to the reaction mixture. The organic layer was separated, dried over Na₂SO₄, and concentrated in vacuo. The residue was purified by column chromatography on silica gel (0-3% EtOAc in petroleum ether) affording the title compound (8.9 g). ¹H NMR (300 MHz, DMSO-d₆): δ 8.19 (s, 1H), 7.71 (m, 2H), 5.88 (dd, 1H), 3.89-3.84 (m, 1H), 3.79-3.73 (m, 1H), 2.42-2.32 (m, 1H), 2.05-1.95 (m, 2H), 1.75-1.70 (m, 1H), 1.60-1.54 (m, 2H).

Step 4: 5-(But-1-yn-1-yl)-4-chloro-1-(tetrahydro-2,1-pyran-2-yl)-1H-indazole

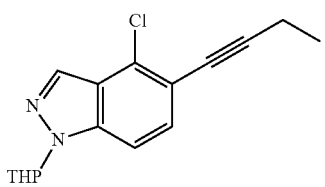

In a 20 mL microwave tube, nitrogen was bubbled through triethylamine (6 mL) for 10 minutes. 5-bromo-4-chloro-1-(tetrahydro-2H-pyran-2-yl)-1H-indazole (2.00 g, 6.34 mmol), tetrabutylammonium fluoride (3.70 g, 14.3 mmol), CuI (0.24 g, 1.3 mmol) and Pd(PPh₃)₄ (1.46 g, 1.26 mmol) were added under nitrogen atmosphere, and bubbling of nitrogen was continued for another 5 minutes. But-1-yn-1-yltrimethylsilane (1.80 g, 14.3 mmol; Intermediate 35) was then added and the tube was sealed immediately. The reaction mixture was heated in a microwave reactor at 120° C. for 3 hours. Four of these reactions (4×2 g scale per run) were combined, mixed with water (100 mL), and extracted with ethyl acetate (2×100 mL). The combined organic layers were dried over Na₂SO₄ and concentrated in vacuo. The residue was purified by column chromatography on silica gel (0~3% ethyl acetate in petroleum ether) affording the title compound (4.5 g, 90%), which was then triturated with petroleum ether (8 mL). The solid was collected and dried to afford a pale yellow powder (3.5 g). This powder was re-crystallized from ethyl acetate (2 mL) to afford the pure title compound as pale yellow crystals (3.0 g). ¹H NMR (400 MHz, DMSO-d₆): δ 8.19 (s, 1H), 7.72 (d, 1H), 7.49 (d, 1H), 5.88 (dd, 1H), 3.89-3.85 (m, 1H), 3.79-3.73 (m, 1H), 2.50 (q, 2H), 2.43-2.33 (m, 1H), 2.05-1.95 (m, 2H), 1.75-1.70 (m, 1H), 1.60-1.55 (m, 2H), 1.21 (t, 3H); LCMS: 289 (M+H)⁺.

Example 22

Preparation of 5-(But-1-yn-1-yl)-7-fluoro-1-(tetrahydro-2H-pyran-2-yl)-1H-indazole (Intermediate 38)

Step 1: 5-Bromo-2,3-difluorobenzaldehyde

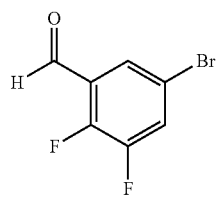

To a solution of 2,3-difluorobenzaldehyde (42 g, 0.296 mol) in H₂SO₄ (150 mL), was added NBS (63 g, 0.354 mol) in three portions over a period of 30 minutes at 60° C. The resulting mixture was heated for 6 hours at this temperature under N₂. Work-up: the reaction mixture was poured into ice water. Petroleum ether (300 mL) was added, and the mixture was stirred for 10 minutes. The organic layer was separated, and the aqueous layer was extracted with more petroleum ether (300 mL). The combined organic layers were dried over Na₂SO₄ and concentrated in vacuo. The residue was purified by column chromatography on silica gel (0~0.5% EtOAc in petroleum ether) to give 5-bromo-2,3-difluorobenzaldehyde (17.4 g). ¹H NMR (300 MHz, CDCl₃): δ 10.32 (s, 1H), 7.81-7.79 (m, 1H), 7.65-7.60 (m, 1H).

Step 2: (E)-5-Bromo-2,3-difluorobenzaldehyde O-methyl oxime

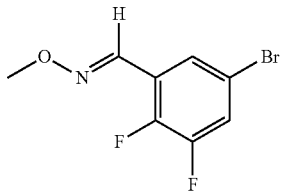

A mixture of 5-bromo-2,3-difluorobenzaldehyde (17.38 g, 78.6 mmol), O-methylhydroxylamine hydrochloride (7.23 g, 86.46 mmol), and $K_2CO_3$ (13 g, 94.32 mmol) in DME (80 mL) was heated at 40° C. for 14 h. Work-up: the reaction mixture was filtered. The filtrate was concentrated in vacuo, and the residue was purified by column chromatography on silica gel (0-2% EtOAc in petroleum ether), to give (E)-5-bromo-2,3-difluorobenzaldehyde O-methyl oxime (19.65 g). $^1$H NMR (CDCl$_3$, 300 MHz): δ 8.20 (s, 1H), 7.76-7.73 (m, 1H), 7.35-7.29 (m, 1H), 4.01 (s, 3H).

Step 3: 5-Bromo-7-fluoro-1H-indazole

A mixture of (E)-5-bromo-2,3-difluorobenzaldehyde O-methyl oxime (19.65 g, 78.6 mmol), hydrazine hydrate (80 mL), and dry THF (80 mL), was heated at 90° C. for 84 h. Work-up: the organic solvent was evaporated. The resulting mixture was diluted with EtOAc (400 mL), washed with water (150 mL), dried over $Na_2SO_4$, and concentrated in vacuo. The residue was purified by column chromatography on silica gel (0=20% EtOAc in petroleum ether) to give 5-bromo-7-fluoro-1H-indazole as a white solid (9.3 g). $^1$H NMR (300 MHz, CDCl$_3$): δ 13.83 (br, 1H), 8.16 (s, 1H), 7.87 (s, 1H), 7.45 (d, 1H).

Step 4: 5-Bromo-7-fluoro-1-(tetrahydro-2H-pyran-2-yl)-1H-indazole

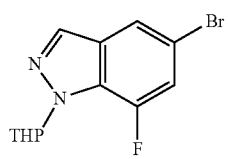

To a mixture of 5-bromo-7-fluoro-1H-indazole (9.3 g, 43.26 mmol) and DHP (4.36 g, 51.9 mmol) in dry dichloromethane (100 mL), was added PTSA (424 mg, 2.16 mmol) at room temperature. The resulting mixture was stirred overnight. Work-up: saturated aqueous NaHCO$_3$ (30 mL) was slowly added to the reaction mixture. The organic layer was separated, dried over Na$_2$SO$_4$, and concentrated in vacuo. The residue was purified by column chromatography on silica gel (0-10% EtOAc in petroleum ether) to give 5-bromo-7-fluoro-1-(tetrahydro-2H-pyran-2-yl)-1H-indazole as a light yellow solid. (7.8 g). $^1$H NMR (300 MHz, CDCl$_3$): δ 7.98 (s, 1H), 7.64 (s, 1H), 7.22 (dd, 1H), 5.84 (dd, 1H), 4.07-4.02 (m, 1H), 3.78-3.71 (m, 1H), 2.62-2.53 (m, 1H), 2.16-2.07 (m, 2H), 1.79-1.71 (m, 2H), 1.63-1.33 (m, 1H).

Step 5: 5-(But-1-yn-1-yl)-7-fluoro-1-(tetrahydro-2H-pyran-2-yl)-1H-indazole

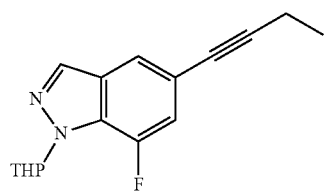

Nitrogen was bubbled into a solution of 5-bromo-7-fluoro-1-(tetrahydro-2H-pyran-2-yl)-1H-indazole (7.5 g, 25.33 mmol) and DMA (100 mL). After 5 min, CuI (241 mg, 1.27 mmol), Pd(OAc)$_2$ (284 mg, 1.27 mmol), dppf (704 mg, 1.27 mmol), K$_2$CO$_3$ (4.89 g, 35.46 mmol), and but-1-yn-1-yltrimethylsilane (4.46 g, 35.46 mmol) were added sequentially with continued N$_2$ bubbling. The resulting mixture was heated at 80° C. for 10 h under N$_2$. The reaction mixture was diluted with EtOAc (250 mL) and H$_2$O (200 mL) and filtered. The organic layer of the filtrate was separated, and the aqueous layer was extracted with EtOAc (2×100 mL). The combined organic layers were washed with brine (3×50 mL), dried over anhydrous Na$_2$SO$_4$, concentrated, and purified by silica gel chromatography (1:30 EtOAc/petroleum ether) to give the pure product as a yellow solid (3.6 g) and an impure product (2 g; further purified to give additional 1.47 g). $^1$H NMR (300 MHz, DMSO-d$_6$): δ 8.19 (d, 1H), 7.68 (d, 1H), 7.26 (dd, 1H), 5.79 (dd, 1H), 3.92-3.87 (m, 1H), 3.69-3.60 (m, 1H), 2.47-2.34 (m, 1H), 2.43 (q, 2H), 2.07-2.02 (m, 2H), 1.76-1.69 (m, 1H), 1.57-1.50 (m, 2H), 1.17 (t, 3H); LCMS: 273 (M+H)$^+$.

Example 23

Preparation of 5-Bromo-3-fluoro-1-(tetrahydro-2H-pyran-2-yl)-1H-indazole (Intermediate 39)

Step 1: 5-Bromo-3-fluoro-1H-indazole

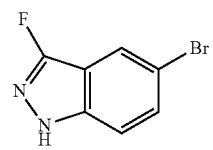

A mixture of 5-bromo-1-(tetrahydro-2H-pyran-2-yl)-1H-indazole (10.0 g, 35.7 mmol; Intermediate 1), acetic acid (4 mL), Selectfluor (25.3 g, 71.4 mmol), and acetonitrile (100 mL) was refluxed under N$_2$ for 2 h. The reaction was allowed to cool to rt, diluted with ethyl acetate (420 mL), and then washed with water (270 mL). The organic layer was dried over Na$_2$SO$_4$ and concentrated in vacuo. The residue was purified on a silica gel column using EtOAc in petroleum ether (1:20) to afford the title compound as yellow solids (6.0 g, yield 78.1%). $^1$H NMR (DMSO-d$_6$, 400 MHz): δ 12.77 (s, 1H), 7.96 (s, 1H), 7.54 (d, 1H), 7.48 (d, 1H).

Step 2: 5-Bromo-3-fluoro-1-(tetrahydro-2H-pyran-2-yl)-1H-indazole

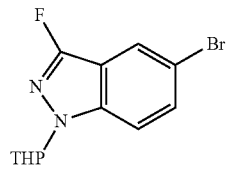

A mixture of 5-bromo-3-fluoro-1H-indazole (6.0 g, 27.9 mmol), PTSA (530.7 mg, 2.79 mmol) and DHP (3.05 g, 36.3 mmol) in dichloromethane (80 mL) was stirred at room temperature for 18 h. The reaction mixture was diluted with dichloromethane (370 mL) and washed with water (230 mL). The organic layer was dried over Na$_2$SO$_4$ and concentrated in vacuo. The residue was purified on a silica gel column using EtOAc in petroleum ether (1:100 to 1:15) to afford the title compound as a yellow solid (6.2 g, yield 74.3%). $^1$H NMR (DMSO-d$_6$, 400 MHz): δ 7.96 (s, 1H), 7.70 (d, 1H), 7.60 (d, 1H), 5.76 (dd, 1H), 3.84-3.80 (m, 1H), 3.71-3.64 (m, 1H), 2.20-2.15 (m, 1H), 1.97-1.87 (m, 2H), 1.69-1.64 (m, 1H), 1.53-1.47 (m, 2H).

Example 24

Preparation of 5-(But-1-yn-1-yl)-3-fluoro-1-(tetrahydro-2H-pyran-2-yl)-1H-indazole (Intermediate 40)

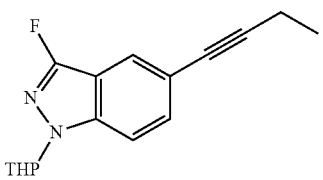

A 100 mL round bottom flask was charged with 5-bromo-3-fluoro-1-(tetrahydro-2H-pyran-2-yl)-1H-indazole (6.2 g, 20.7 mmol; Intermediate 39), DMA (20 mL), CuI (393.3 mg, 2.07 mmol), Pd(OAc)$_2$ (465.0 mg, 2.07 mmol), dppf (1.1 g, 2.07 mmol), Cs$_2$CO$_3$ (10.8 g, 33.1 mmol), and but-1-yn-1-yltrimethylsilane (3.4 g, 26.9 mmol; Intermediate 35) sequentially while N$_2$ was bubbled through the solution. The resulting mixture was heated at 80° C. for 10 h under N$_2$. The reaction mixture was diluted with EtOAc (350 mL) and H$_2$O (300 mL) and filtered. The organic layer of the filtrate was separated, and the aqueous layer was extracted with EtOAc (2×50 mL). The combined organic layers were washed with brine (3×100 mL), dried over anhydrous Na$_2$SO$_4$, and concentrated in vacuo. The residue was purified on a silica gel column using EtOAc in petroleum ether (1:30) to afford the title compound as a yellow solid (3.9 g, yield 69.1%). $^1$H NMR (DMSO-d$_6$, 400 MHz): δ 7.76-7.71 (m, 2H), 7.49 (d, 1H), 5.79 (dd, 1H), 3.88-3.85 (m, 1H), 3.74-3.71 (m, 1H), 2.44 (q, 2H), 2.24-2.21 (m, 1H), 2.01-1.91 (m, 2H), 1.70-1.65 (m, 1H), 1.57-1.54 (m, 2H), 1.18 (t, 3H); LCMS: 273 (M+H)$^+$.

Example 25

Preparation of 5-(3-Cyclopropylprop-1-yn-1-yl)-1-(tetrahydro-2H-pyran-2-yl)-1H-indazole (Intermediate 41)

Step 1: (3-Cyclopropylprop-1-yn-1-yl)trimethylsilane

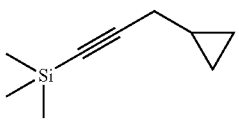

A 500 mL three-necked round bottom flask was charged with (trimethylsilyl)acetylene (15 g, 153 mmol) and dry THF (75 mL). The solution was cooled to −78° C., and a solution of n-butyllithium in hexane (2.5 M, 75 mL, 188 mmol) was added dropwise over 30 minutes. The resulting mixture was stirred at 0° C. for 10 minutes and then re-cooled to −78° C. HMPA (40 g, 223 mmol) was added, and the mixture was stirred at −78° C. for 30 minutes. (Bromomethyl)cyclopropane (20.6 g, 153 mmol) was then added. The reaction mixture was allowed to warm to room temperature and stirred overnight. Upon completion, the reaction mixture was washed with water (4×100 mL) and brine (2×100 mL) sequentially. The organic layer was dried over anhydrous sodium sulfate. Hexane and THF was distilled off at 75~110° C. then distillation at 138~142° C. afforded the title compound (12 g). $^1$H NMR (400 MHz, DMSO-d$_6$): δ 2.27 (d, 2H), 0.91-0.84 (m, 1H), 0.43-0.34 (m, 2H), 0.19-0.14 (m, 2H), 0.11 (s, 9H).

Step 2: 5-(3-Cyclopropylprop-1-yn-1-yl)-1-(tetrahydro-2,1-pyran-2-yl)-1H-indazole

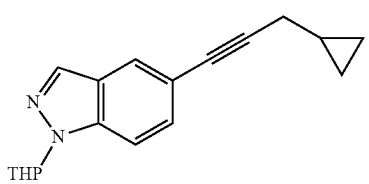

To a mixture of 5-bromo-1-(tetrahydro-2H-pyran-2-yl)-1H-indazole (4.0 g, 14.3 mmol; Intermediate 1), Pd(PPh$_3$)$_2$Cl$_2$ (1.0 g, 1.43 mmol), CuI (271 mg, 1.43 mmol), TBAF (11.2 g, 42.8 mmol), triethylamine (20 mL), and THF (20 mL), was added (3-cyclopropylprop-1-yn-1-yl)trimethylsilane (7.9 g, 42.8 mmol) under N$_2$ atmosphere. The resulting mixture was stirred at 80° C. for 16 hours under N$_2$ atmosphere. Upon completion, the reaction mixture was diluted with EtOAc and filtered. The filtrate was washed with water (3×10 mL), dried over Na$_2$SO$_4$ and concentrated in vacuo. The residue was purified by column chromatography on silica gel (0~10% EtOAc in petroleum ether) affording the title compound as yellow solid (3.4 g). $^1$H NMR (400 MHz, DMSO-d$_6$): δ 8.09 (s, 1H), 7.84 (s, 1H), 7.69 (d, 1H), 7.39

(dd, 1H), 5.83 (dd, 1H), 3.89-3.86 (m, 1H), 3.77-3.70 (m, 1H), 2.49 (d, 2H), 2.43-2.34 (m, 1H), 2.05-1.94 (m, 2H), 1.79-1.71 (m, 1H), 1.60-1.55 (m, 2H), 1.06-0.96 (m, 1H), 0.52-0.46 (m, 2H), 0.30-0.25 (m, 2H); LCMS: 281 (M+H)+.

Example 26

Preparation of (Cyclobutylethynyl)trimethylsilane (Intermediate 42)

Step 1: (6-Chlorohex-1-yn-1-yl)trimethylsilane

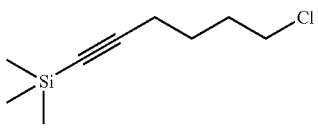

To a solution of 6-chlorohex-1-yne (100 mL, 94.6 g, 0.82 mol) in anhydrous Et$_2$O (500 mL) at −78° C., n-butyllithium (2.5 M in hexane, 360 mL, 0.90 mol) was added over 40 minutes. The resulting mixture was stirred for 30 minutes at −78° C. Chlorotrimethylsilane (125 mL, 1.0 mol) was then added. The mixture was allowed to warm to room temperature and stirred for 16 h. The reaction mixture was carefully quenched with saturated aqueous NH$_4$Cl (300 mL) at room temperature and extracted with Et$_2$O (2×200 mL). The combined organic layers were washed with brine (200 mL), dried over anhydrous Na$_2$SO$_4$, and concentrated in vacuo to afford the title compound (144 g, yield 93%). $^1$H NMR (DMSO-d$_6$, 400 MHz): δ 3.65 (t, 2H), 2.25 (t, 2H), 1.82-1.75 (m, 2H), 1.58-1.51 (m, 2H), 0.12 (s, 9H).

Step 2: (Cyclobutylethynyl)trimethylsilane

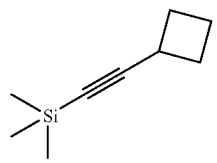

To a solution of diisopropylamine (153 g, 1.52 mol) in anhydrous THF (1.0 L) at 0° C., n-butyllithium (2.5 M in hexane, 608 mL, 1.52 mol) was added dropwise. The mixture was stirred for 20 minutes at 0° C. and then cooled to −78° C. To this mixture, a solution of (6-chlorohex-1-yn-1-yl)trimethylsilane (144 g, 0.76 mol) in anhydrous THF (200 mL) was added dropwise. The resulting mixture was allowed to warm to room temperature and stirred for 16 h. The reaction mixture was carefully quenched at room temperature with saturated aqueous NH$_4$Cl (500 mL), and then extracted with pentane (2×200 mL). The combined organic layers were washed with brine (500 mL) and dried over anhydrous Na$_2$SO$_4$. The solvent was evaporated on a rotary evaporator. The residue was distilled at 160-162° C./760 Torr to afford the title compound as a colorless liquid (81 g, yield 70%). $^1$H NMR (CDCl$_3$, 400 MHz): δ 3.05-3.01 (m, 1H), 2.26-2.20 (m, 2H), 2.17-2.10 (m, 2H), 1.93-1.84 (m, 2H), 0.11 (s, 9H).

Example 27

Preparation of 5-(Cyclobutylethynyl)-1-(tetrahydro-2H-pyran-2-yl)-1H-indazole (Intermediate 43)

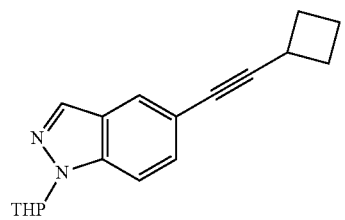

A 100 mL round bottom flask was charged with 5-bromo-1-(tetrahydro-2H-pyran-2-yl)-1H-indazole (6.8 g, 24.2 mmol; Intermediate 1), DMA (30 mL), CuI (0.46 g, 2.4 mmol), Pd(OAc)$_2$ (0.55 g, 2.4 mmol), dppf (1.35 g, 2.4 mmol), Cs$_2$CO$_3$ (11.2 g, 34.4 mmol), and (cyclobutylethynyl)trimethylsilane (5.2 g, 34.1 mmol; Intermediate 42) sequentially while N$_2$ was bubbled through the mixture. The resulting mixture was heated at 80° C. under N$_2$ atmosphere for 2 hours. The reaction mixture was cooled to room temperature, diluted with EtOAc (100 mL) and H$_2$O (100 mL) and filtered. The organic layer of the filtrate was separated, and the aqueous layer was extracted with additional EtOAc (2×50 mL). The combined organic layers were washed with brine (3×100 mL), dried over anhydrous Na$_2$SO$_4$, and concentrated in vacuo. The residue was purified on a silica gel column using 0-10% EtOAc in petroleum ether to afford the title compound as yellow oil (4.8 g, 71%). $^1$H NMR (DMSO-d$_6$): δ 8.08 (s, 1H), 7.82 (s, 1H), 7.68 (d, 1H), 7.39 (dd, 1H), 5.82 (dd, 1H), 3.89-3.85 (m, 1H), 3.76-3.69 (m, 1H), 3.30-3.24 (m, 1H), 2.39-2.26 (m, 3H), 2.19-2.09 (m, 2H), 2.03-1.84 (m, 4H), 1.75-1.70 (m, 1H), 1.58-1.55 (m, 2H); LCMS: 281 (M+H)+.

The Intermediate in Table 6 was prepared from Intermediate 39 & 42 following the procedure outlined for Intermediate 43.

TABLE 6

| Intermediate 44 | 5-(Cyclobutylethynyl)-3-fluoro-1-(tetrahydro-2H-pyran-2-yl)-1H-indazole | 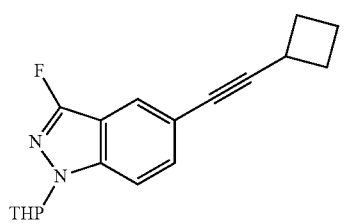 |
| --- | --- | --- |

General Procedure A: Installation of the tetrahydropyran (THP) protecting group for the indazole NH.

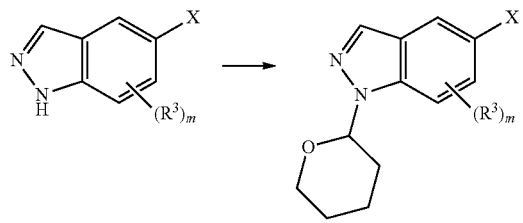

3,4-Dihydro-2H-pyran (1.1-10 equiv) was added to a solution of the appropriate halo-indazole (1.0 equiv), PPTS (or pTsOH, 0.05-0.3 equiv), and dichloromethane (~2 mL/mmol) at room temperature. The reaction was stirred under $N_2$ for 6-48 h (until complete by TLC or LCMS), quenched with water, and then extracted with dichloromethane. The extracts were dried, filtered, concentrated, and purified by silica gel chromatography to give the protected halo-indazole.

General Procedure B: Coupling of the protected halo-indazoles with alkynyl-trimethylsilanes

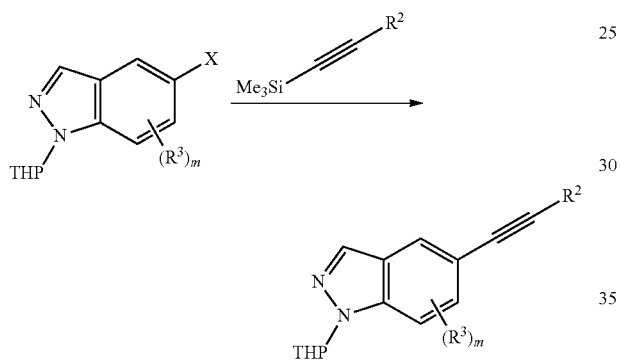

A mixture of the appropriate protected halo-indazole (1.0 equiv), $Cs_2CO_3$ (1.3-3.0 equiv), CuI (0.05-0.2 equiv), $Pd(OAc)_2$ (0.05-0.2 equiv), dppf (0.05-0.2 equiv), and N,N-dimethylacetamide (DMA, 1-2 mL/mmol) was degassed with three vacuum/nitrogen cycles. The appropriate alkynyl-trimethylsilane (1.3-2.0 equiv) was added, and the reaction was heated at 80° C. under $N_2$ for 2-24 hours (until complete by TLC or LCMS). The reaction was allowed to cool to room temperature, diluted with ethyl acetate and water, and then filtered through Celite. The aqueous layer was separated and extracted with ethyl acetate. The organics were combined, dried, filtered, concentrated, and then purified by silica gel column chromatography to give the alkynyl-indazole.

Note: Alternate bases include $K_2CO_3$ and CsF; Alternate ligands include 1,3-Bis(2,4,6-trimethylphenyl)imidazolium chloride and $Ph_3P$; Alternate catalysts include $Pd(PPh_3)_4$ and $PdCl_2(PPh_3)_2$; Alternate solvents include THF and pyrrolidine. Water content seems to impact the rate of this reaction: when anhydrous $Cs_2CO_3$ and anhydrous solvent were used, 1% water (v/v with respect to solvent) was added to the reaction, and when the $Cs_2CO_3$ and/or solvent were not anhydrous, no water was added.

An alternate procedure has also been employed, especially with iodo-indazoles: The appropriate alkynyl-trimethylsilane (2.1 equiv) was added to a degassed solution of TBAF (2.0 equiv, 0.5M in THF). After 5-30 min, the appropriate halo-indazole (1.0 equiv), CuI (0.05-0.3 equiv), and $Pd(PPh_3)_4$ (0.05-0.2 equiv) were added. The reaction was stirred at room temperature under $N_2$ for 2-24 hours (until complete by TLC or LCMS), then diluted with water, and extracted with an appropriate solvent. The extracts were combined, dried, filtered, concentrated, and then purified by silica gel column chromatography to give the alkynyl-indazole.

Note: Alternate catalysts include $PdCl_2(PPh_3)_2$; Cosolvents include triethylamine and pyrrolidine; When employing bromo-heterocycles, the reaction temperature was increased (80-120° C.).

General Procedure C: Multi-component cross-coupling of the alkynyl-indazoles.

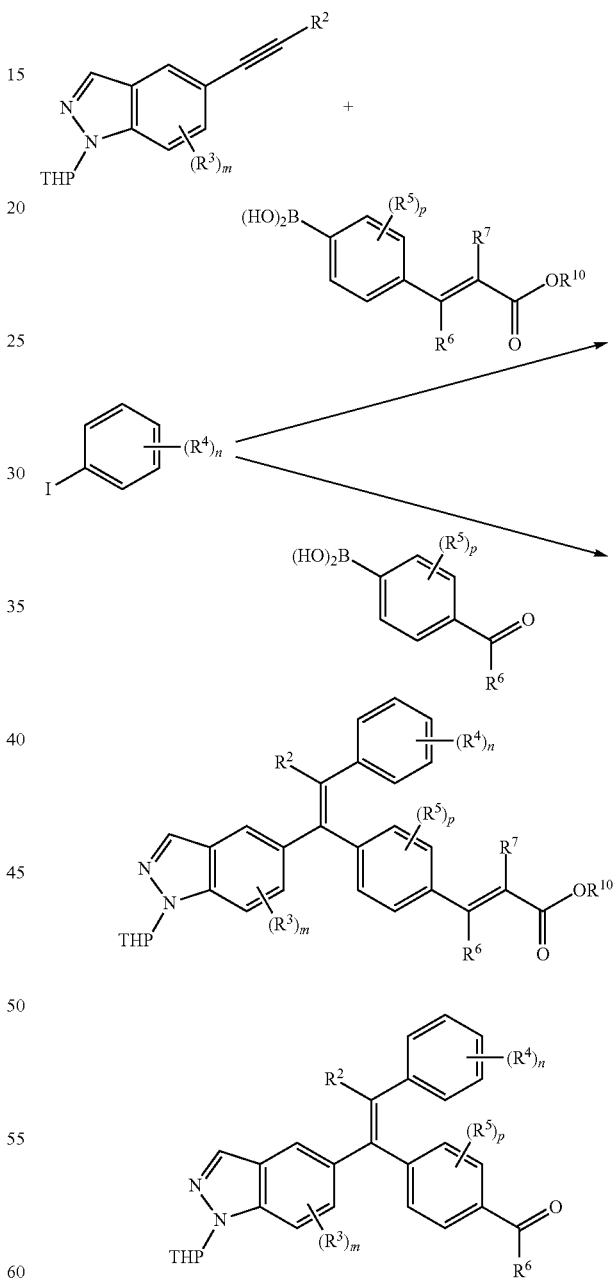

A mixture of the appropriate alkynyl-indazole (1.0 equiv), aryl-iodide (3.0 equiv), aryl-boronic acid (3.0 equiv), $K_2CO_3$ (3.0 equiv), and N,N-dimethylformamide (DMF)/water (2:1, 50 mL/mmol) was degassed with three vacuum/$N_2$ cycles and then heated at 45° C. After 10 min (or when homogenous), a solution of Pd(PhCN)$_2$Cl$_2$ (0.01 equiv) in DMF was added. The reaction was stirred at 45° C. for 4-24 h (until complete by TLC or LCMS), allowed to cool to room temperature, quenched with water, and then extracted with ethyl acetate. The extracts were washed with water, washed with brine, dried, filtered, concentrated, and purified by silica gel chromatography to give the desired tetra-substituted alkene.

Note 1: In some instances, all chemicals were simply mixed at room temperature, degassed, and then heated. In other instances, the boronic acid was added last as a DMF/water solution.

Note 2: When incomplete conversion of alkynyl-indazole was observed (especially with ortho-substituted aryl-iodides), additional aryl-iodide, aryl-boronic acid, and K$_2$CO$_3$ (1-3 equiv each) were added, and heating was continued for 8-24 h. In some instances, this was repeated multiple times to improve the conversion and yield.

General Procedure D: Alternate multi-component cross-coupling of the alkynyl-indazoles.

0.03 equiv; Note 1), and solvent (2 mL/mmol of dioxane, DME, 2-MeTHF, PhMe, or DMA; Note 2) was degassed with three vacuum/N$_2$ cycles and then heated at 80-120° C. (Note 3) under N$_2$ for 1-8 h (until complete by TLC or LCMS). The reaction was allowed to cool to room temperature and then either 1) taken directly into Step 2; 2) concentrated to give a crude residue [usually a foam]; or 3) concentrated and purified by silica gel chromatography to give the pure bis(pinacolato)diboryl-alkene.

Note 1: Most commonly, 0.01 equivalents were utilized. Note 2: Most commonly, 2-MeTHF was utilized. Note 3: Most commonly, reactions were refluxed.

Step 2: Cross-coupling of the bis(pinacolato)diboryl-alkene

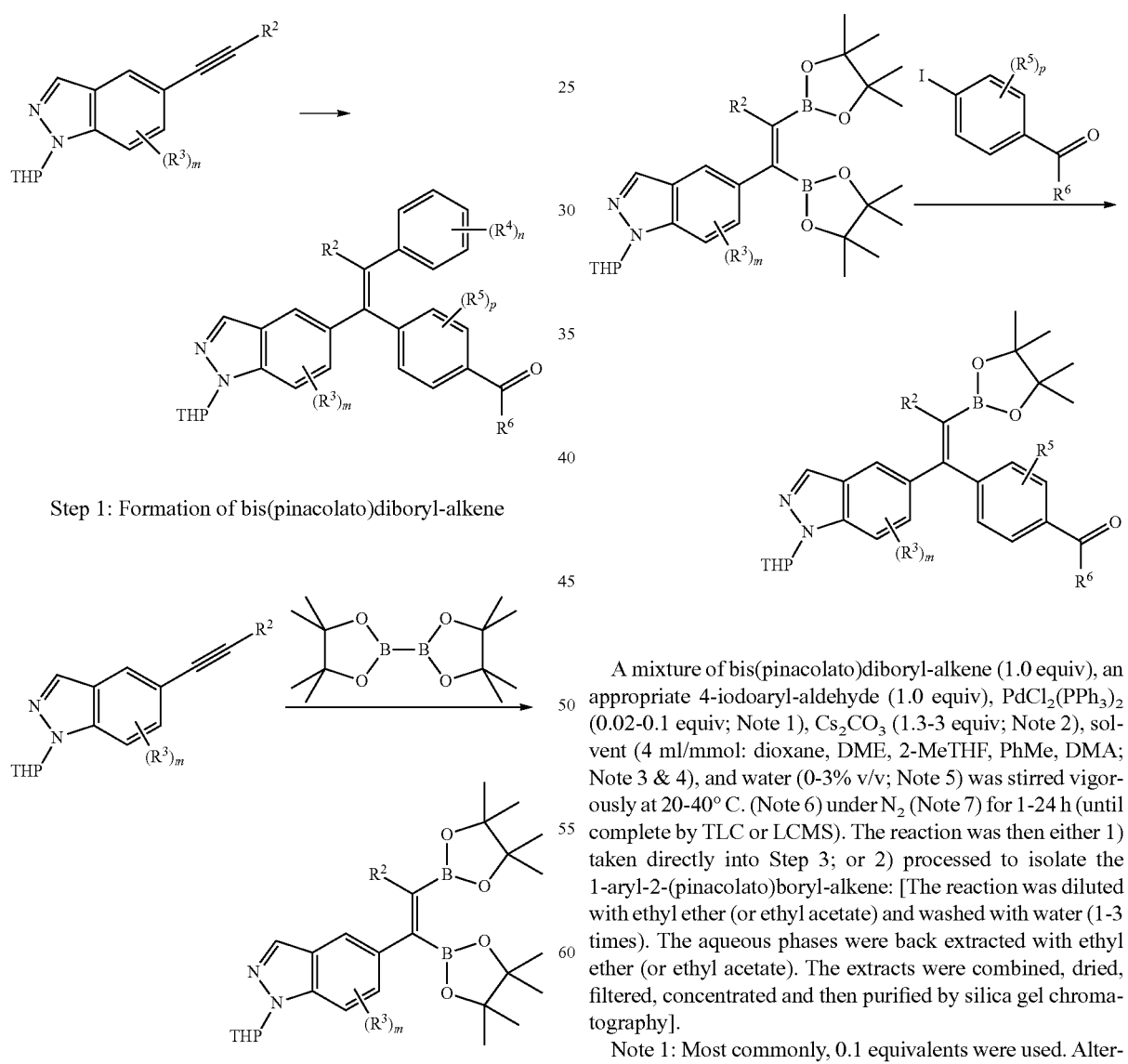

Step 1: Formation of bis(pinacolato)diboryl-alkene

A solution of the appropriate alkynyl-indazole (1.0 equiv), bis(pinacolato)diboron (1.01-1.02 equiv), Pt(PPh$_3$)$_4$ (0.0025-

A mixture of bis(pinacolato)diboryl-alkene (1.0 equiv), an appropriate 4-iodoaryl-aldehyde (1.0 equiv), PdCl$_2$(PPh$_3$)$_2$ (0.02-0.1 equiv; Note 1), Cs$_2$CO$_3$ (1.3-3 equiv; Note 2), solvent (4 ml/mmol: dioxane, DME, 2-MeTHF, PhMe, DMA; Note 3 & 4), and water (0-3% v/v; Note 5) was stirred vigorously at 20-40° C. (Note 6) under N$_2$ (Note 7) for 1-24 h (until complete by TLC or LCMS). The reaction was then either 1) taken directly into Step 3; or 2) processed to isolate the 1-aryl-2-(pinacolato)boryl-alkene: [The reaction was diluted with ethyl ether (or ethyl acetate) and washed with water (1-3 times). The aqueous phases were back extracted with ethyl ether (or ethyl acetate). The extracts were combined, dried, filtered, concentrated and then purified by silica gel chromatography].

Note 1: Most commonly, 0.1 equivalents were used. Alternate catalysts include PdCl$_2$(dppf). Note 2: Most commonly, 2 or 3 equivalents were used. Water content of the Cs$_2$CO$_3$ affects this reaction, see Note 5. Note 3: Most commonly, 2-MeTHF was used. Note 4: When the bis(pinacolato)diboryl-alkene is brought into this step as a solution from Step 1, solvent (2 mL/mmol) is added to make the final volume of solvent approximately 4 mL/mmol. Note 5: Most commonly, anhydrous $Cs_2CO_3$ and anhydrous solvent were used, so 1-2% water (v/v with respect to solvent) was added to the reaction. When the $Cs_2CO_3$ and/or solvent were not anhydrous, no water was added. Note 6: Most commonly, reactions were run at room temperature. Note 7: In some instances, this reaction was degassed with three vacuum/$N_2$ cycles.

Step 3: Cross-coupling of the 1-aryl-2-(pinacolato)boryl-alkene

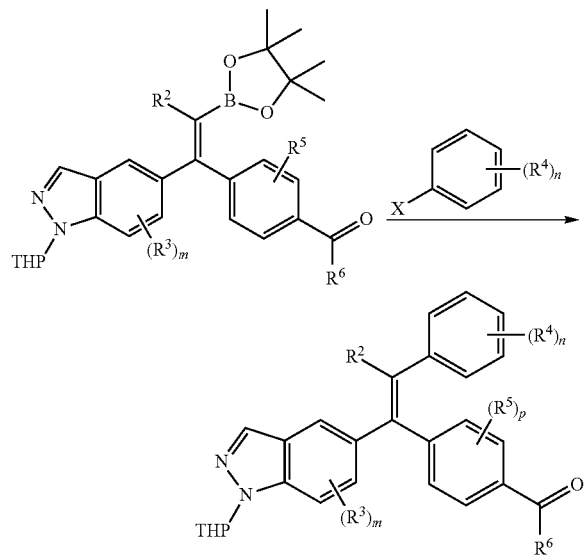

A mixture of 1-aryl-2-(pinacolato)boryl-alkene (1.0 equiv), an appropriate aryl-halide (1.3-2 equiv; Note 1), $PdCl_2(PPh_3)_2$ (0.02-0.1 equiv; Note 2), solvent (4 mL/mmol: dioxane, DME, 2-MeTHF, DMSO; Notes 3 & 4), and KOH (3-6M, 5-6 equiv; Note 5) was degassed with three vacuum/$N_2$ cycles and then heated at 80-100° C. (Note 6) under $N_2$ for 1-24 h (until complete by TLC or LCMS). The reaction was allowed to cool to room temperature, diluted with ethyl ether (or ethyl acetate), and washed with water (1-3 times). The aqueous phases were back extracted with ethyl ether (or ethyl acetate). The extracts were combined, dried, filtered, concentrated and then purified by silica gel chromatography to give the desired tetra-substituted alkene.

Note 1: Most commonly, 1.5 equivalents of aryl-iodide were used. Note 2: Most commonly, 0.1 equivalents were used. Alternate catalysts include $PdCl_2(dppf)$. Note 3: Most commonly, dioxane, DME, or 2-MeTHF was used. Note 4: When the 1-aryl-2-(pinacolato)boryl-alkene is brought into this step directly from Step 2, no additional solvent or $PdCl_2(PPh_3)_2$ was added. Only the aryl-halide and KOH are added. Note 5: Most commonly, 6 equiv of KOH are used, and the aqueous solution of KOH is 4M or 6M. For compounds with sensitive functionality, $K_2CO_3$ (6 equiv, 4M aqueous) is used in place of KOH, and DMSO is used as either the sole solvent or a co-solvent. Note 6: Most commonly, reactions were refluxed.

General Procedure E: Olefination of the tetrasubstituted-alkene aryl-aldehydes

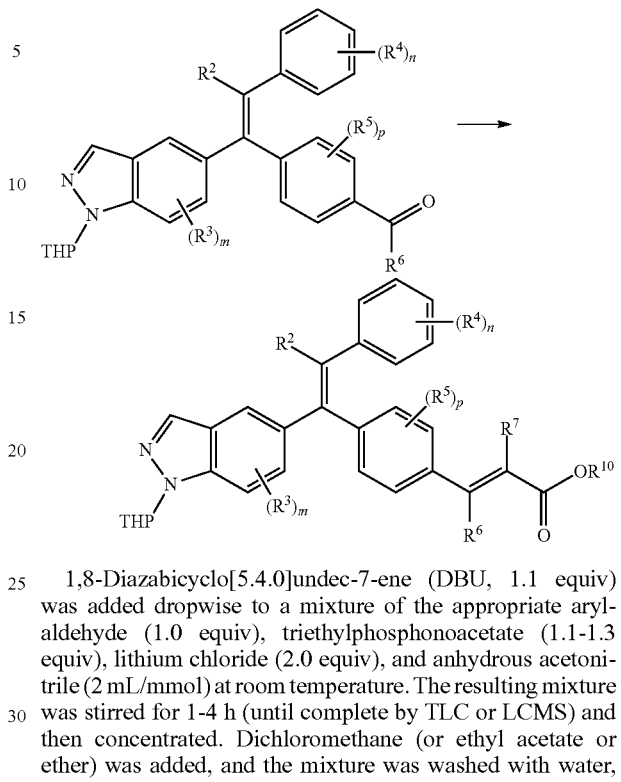

1,8-Diazabicyclo[5.4.0]undec-7-ene (DBU, 1.1 equiv) was added dropwise to a mixture of the appropriate aryl-aldehyde (1.0 equiv), triethylphosphonoacetate (1.1-1.3 equiv), lithium chloride (2.0 equiv), and anhydrous acetonitrile (2 mL/mmol) at room temperature. The resulting mixture was stirred for 1-4 h (until complete by TLC or LCMS) and then concentrated. Dichloromethane (or ethyl acetate or ether) was added, and the mixture was washed with water, washed with brine, dried, filtered, concentrated, and purified by silica gel column chromatography to give the desired acrylic ester.

Note 1: In some instances, alternate phosphonate reagents were utilized to give the desired acrylic ester. Note 2: Alternate reaction conditions: 1-2 equivalents of phosphonate in THF at -78° C. or 0° C. were treated with n-BuLi or NaH (1-2 equiv). Then aryl-aldehyde (1 equiv) was added, and the reaction was continued at -78° C., 0° C., or room temperature until the reaction was complete by TLC and/or LCMS.

General Procedure F: Removal of the tetrahydropyran protecting group from the indazole.

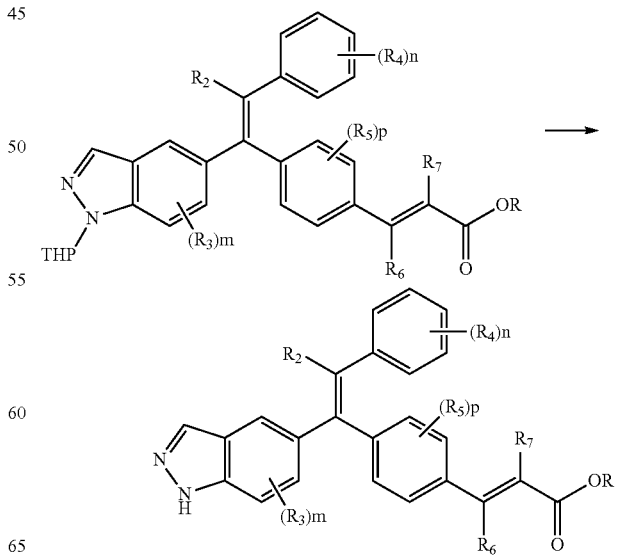

A solution of HCl (Note 1) was added to a solution of the THP-protected indazole (1.0 equiv) in ethanol (2-5 mL/mmol; Note 2) at room temperature. The mixture was heated at 70° C. (Note 3) for 2-8 h (until complete by TLC or LCMS), allowed to cool to room temperature, and concentrated to give a crude product that was either carried on directly to the next step or purified by silica gel chromatography.

Note 1: Most commonly, 2M HCl in diethyl ether or 1.25M HCl in ethanol were used. Most commonly, the volume of HCl solution used was 10% of the solvent volume. Note 2: Most commonly, the concentration was 5 mL/mmol. In some instances, methanol or isopropanol were used. Note 3: In some instances, the reaction was heated at 80° C. or reflux.

General Procedure G: Hydrolysis of the acrylic ester to the acrylic acid.

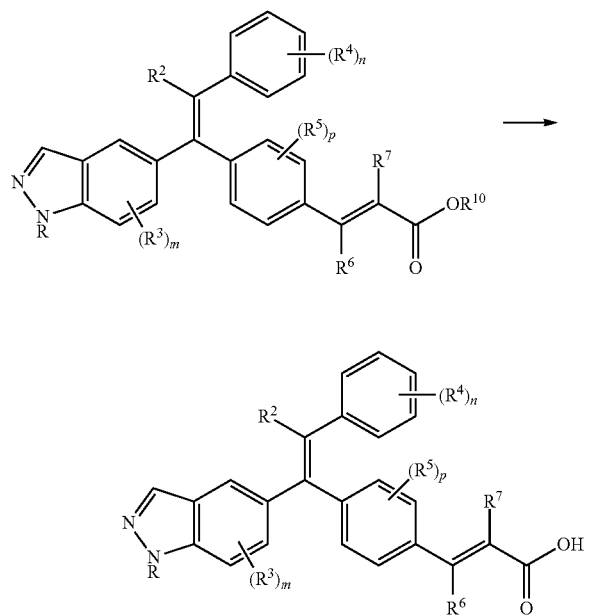

An aqueous solution of LiOH (2-20 equiv; Note 1) was added to a solution of the appropriate ester (1.0 equiv) in ethanol/tetrahydrofuran (1:1, 10 mL/mmol; Note 2) at room temperature, and the mixture was stirred for 4-24 h (until complete by TLC or LCMS). A solution of HCl (1M aqueous) was added until the pH was 3 (Note 3). The mixture was diluted with water and extracted with ethyl acetate (or dichloromethane or ether). The organic layer was washed with water, washed with brine, dried, filtered, concentrated, and purified by silica gel chromatography or preparative-HPLC to give the desired acrylic acid.

Note 1: Most commonly, a 2M solution of aqueous LiOH was used, or the LiOH was dissolved in a minimum amount of water. In some instances, NaOH or KOH was used. Note 2: In some instances, a single solvent (ethanol, dioxane, or tetrahydrofuran) was used. Note 3: Alternate work-up procedures have been employed including: i) the use of sat'd NH4Cl in place of aqueous HCl and ii) removal of the organic solvent by rotary evaporation prior to acid quench.

Example 28

Preparation of Compound 1: (E)-Ethyl 3-(4-((E)-1-(1H-indazol-5-yl)-2-phenylbut-1-en-1-yl) phenyl)acrylate Step 1: (E)-Ethyl 3-(4-((E)-2-phenyl-1-(1-(tetrahydro-2H-pyran-2-yl)-1H-indazol-5-yl)but-1-en-1-yl)phenyl)acrylate

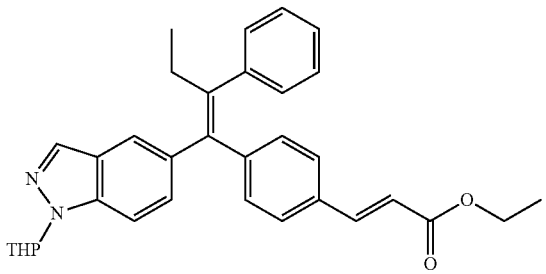

A solution of 5-(but-1-yn-1-yl)-1-(tetrahydro-2H-pyran-2-yl)-1H-indazole (2.5 g, 9.83 mmol, Intermediate 3), iodobenzene (6 g, 29.5 mmol), (E)-(4-(3-ethoxy-3-oxoprop-1-en-1-yl)phenyl)boronic acid (6.49 g, 29.5 mmol), $K_2CO_3$ (4.08 g, 29.5 mmol), and N,N-dimethylformamide/water (2:1, 492 mL) was degassed with 3 vacuum/$N_2$ cycles and then heated at 45° C. until it was a homogenous solution. A solution of Pd(PhCN)$_2$Cl$_2$ (38 mg, 0.098 mmol) in N,N-dimethylformamide (0.5 mL) was added. The resulting mixture was stirred at 45° C. overnight. Upon completion, the reaction mixture was cooled down to room temperature, quenched with water (500 mL), and extracted with ethyl acetate (3×500 mL). The combined organics were washed with water, washed with brine, dried over sodium sulfate, filtered, and concentrated to give the crude product. This crude material was purified on a silica gel column eluted with 0-50% ethyl acetate in hexanes affording the title compound as off-white foam (3.71 g). LCMS: 423 [(M-THP+H)+H]$^+$.

Step 2: (E)-Ethyl 3-(4-((E)-1-(1H-indazol-5-yl)-2-phenylbut-1-en-1-yl)phenyl)acrylate

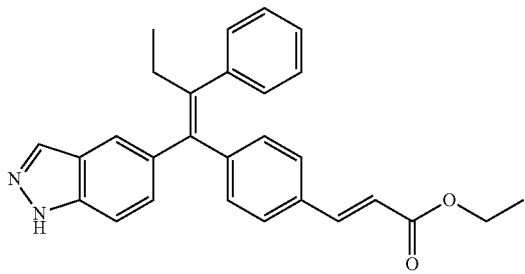

To a solution of (E)-ethyl 3-(4-((E)-2-phenyl-1-(1-(tetrahydro-2H-pyran-2-yl)-1H-indazol-5-yl)but-1-en-1-yl) phenypacrylate (3.5 g, 6.9 mmol) in ethyl alcohol (69 mL), HCl (6 mL, 2M in diethyl ether) was added at room temperature. The resulting mixture was then heated at 70° C. for 2 h. Upon completion, the mixture was cooled down to room temperature and concentrated to give the crude product. This crude material was purified on a silica gel column eluted with 0-100% ethyl acetate in hexanes affording an off-white solid (2.5 g). $^1$H NMR (300 MHz, DMSO-d$_6$): δ 13.10 (s, 1H), 8.08 (s, 1H), 7.69 (s, 1H), 7.53 (d, 1H), 7.48 (d, 1H), 7.39 (d, 2H), 7.27-7.11 (m, 6H), 6.89 (d, 2H), 6.45 (d, 1H), 4.20 (q, 2H), 2.43 (q, 2H), 1.22 (t, 3H), 0.87 (t, 3H); LCMS: 423 (M+H)$^+$.

Example 29

Preparation of Compound 2: (E)-3-(4-((E)-1-(1H-Indazol-5-yl)-2-phenylbut-1-en-1-yl)phenyl)acrylic acid

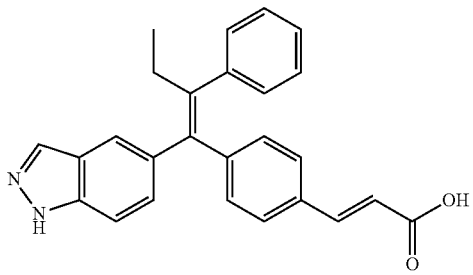

To a solution of (E)-ethyl 3-(4-((E)-1-(1H-indazol-5-yl)-2-phenylbut-1-en-1-yl)phenyl)acrylate (2.5 g, 5.9 mmol; Compound 1) in THF-EtOH (1:1, 59 mL), an aqueous solution of LiOH (2.8 g, 118 mmol; dissolved in a minimum amount of water) was added at room temperature. The resulting mixture was stirred overnight. The reaction was monitored by LCMS. Upon completion, 1N aqueous HCl was added until pH was 3. Then, the mixture was diluted with water and extracted with ethyl acetate (3×200 mL). The combined organic layers were washed with water, washed with brine, dried over sodium sulfate, filtered, and concentrated to give the crude product. This crude material was purified on a silica gel column eluted with 0-20% methanol in dichloromethane affording the title compound as a pale yellow solid (1.9 g). $^1$H NMR (300 MHz, DMSO-$d_6$): δ 13.11 (s, 1H), 12.30 (br, 1H), 8.08 (s, 1H), 7.65 (s, 1H), 7.53 (d, 1H), 7.43 (d, 1H), 7.37 (d, 2H), 7.29-7.11 (m, 6H), 6.88 (d, 2H), 6.37 (d, 1H), 2.44 (q, 2H), 0.87 (t, 3H); LCMS: 395 (M+H)$^+$.

Compounds 3 to 89 were prepared from alkynyl-indazole intermediates following General Procedures C, F, & G. The alkynyl-indazole intermediates have either i) been described herein or ii) were prepared from known or commercially available halo-indazoles following General Procedures A & B.

Compounds 90 to 92 are intermediates from the synthesis of Compounds 3, 12, & 13.

Example 30

Preparation of Compound 93: (E)-3-(4-((E)-2-(3-Hydroxyphenyl)-1-(1H-indazol-5-yl)but-1-en-1-yl)phenyl)acrylic acid

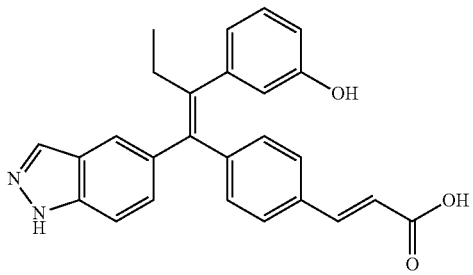

A 10-mL recovery flask equipped with a magnetic stir bar, a rubber septum and N$_2$ inlet was charged with (E)-3-(4-((E)-1-(1H-indazol-5-yl)-2-(3-methoxyphenyl)but-1-en-1-yl)phenyl)acrylic acid (30 mg, 0.07 mmol, Compound 5) and DCM (1.4 mL). This solution was cooled down to 0° C. in an ice-bath. Then, BBr$_3$ (88 mg, 0.35 mmol) was added dropwise via a syringe. The reaction mixture was stirred at 0° C. for 1 h. Upon completion, the reaction was quenched with methanol (5 mL) at 0° C. The resulting mixture was concentrated under reduced pressure to give the crude product that was directly purified on a reversed phased C-18 column eluted with 40-100% acetonitrile in water in the presence of 0.1% TFA affording the title compound as an off-white solid (11 mg). $^1$H NMR (300 MHz, DMSO-$d_6$): δ 13.11 (s, 1H), 12.32 (br, 1H), 9.23 (s, 1H), 8.08 (s, 1H), 7.62 (s, 1H), 7.52 (d, 1H), 7.45-7.35 (m, 3H), 7.12 (d, 1H), 7.00 (t, 1H), 6.90 (d, 2H), 6.59-6.53 (m, 3H), 6.36 (d, 1H), 2.37 (q, 2H), 0.89 (t, 3H); LCMS: 411 (M+H)$^+$.

Example 31

Preparation of Compound 94: (E)-3-(4-((E)-2-(2-Hydroxyphenyl)-1-(1H-indazol-5-yl)but-1-en-1-yl)phenyl)acrylic acid

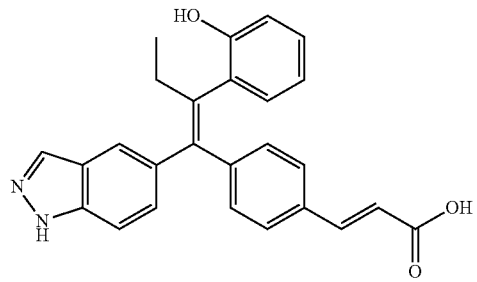

A 10-mL recovery flask equipped with a magnetic stir bar, a rubber septum and N$_2$ inlet was charged with (E)-ethyl 3-(4-((E)-1-(1H-indazol-5-yl)-2-(2-methoxyphenyl)but-1-en-1-yl)phenyl)acrylate (145 mg, 0.32 mmol, an intermediate in the synthesis of Compound 12) in DCM (6 mL). This solution was cooled down to −78° C. in an IPA/dry ice-bath. Then, BBr$_3$ (24.1 mg, 0.96 mmol) was added dropwise via a syringe. The reaction mixture was gradually warmed to 0° C. for 1 h. Upon completion, the reaction was quenched with methanol (5 mL) at 0° C. The resulting mixture was concentrated under reduced pressure to give the crude product. Then, this crude product was dissolved in THF-EtOH (1:1, 6 mL), and aqueous LiOH (0.15 g, 6.4 mmol) was added at room temperature. The resulting mixture was stirred at this temperature overnight. Reaction was monitored by LCMS. Upon completion, 1N aqueous HCl was added until pH was 3. Then, the mixture was diluted with water and extracted with ethyl acetate (3×100 mL). The combined organic layers were washed with water (100 mL), washed with brine (50 mL), dried over sodium sulfate, filtered, and concentrated to give the crude product. This crude material was purified on a reversed phase C-18 column eluted with 40-100% acetonitrile in water in the presence of 0.1% TFA affording the title compound. $^1$H NMR (300 MHz, DMSO-$d_6$): δ 13.07 (s, 1H), 12.34 (br, 1H), 9.33 (br, 1H), 8.08 (d, 1H), 7.65 (s, 1H), 7.53 (d, 1H), 7.40 (d, 1H), 7.32 (d, 2H), 7.15 (dd, 1H), 7.00-6.94 (m, 3H), 6.81-6.76 (m, 2H), 6.57 (dt, 1H), 6.34 (d, 1H), 2.43-2.30 (m, 2H), 0.88 (t, 3H); LCMS: 411 (M+H)$^+$.

Compound 95 was prepared following the procedure outlined for Compound 94.

Example 32

Preparation of Compound 96: (E)-3-(4-((E)-2-(3-Butoxyphenyl)-1-(1H-indazol-5-yl)but-1-en-1-yl)phenyl)acrylic acid Step 1: (E)-Ethyl 3-(4-((E)-2-(3-hydroxyphenyl)-1-(1-(tetrahydro-2H-pyran-2-yl)-1H-indazol-5-yl)but-1-en-1-yl)phenyl)acrylate

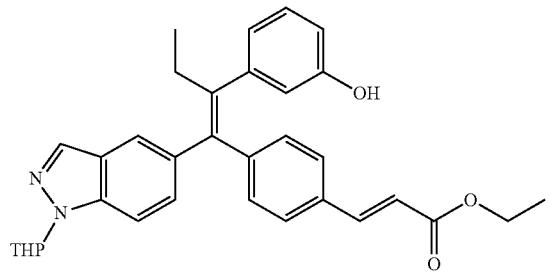

The title compound was prepared from Intermediate 3,3-iodophenol, and (E)-(4-(3-ethoxy-3-oxoprop-1-en-1-yl)phenyl)boronic acid following General Procedure C.

Step 2: (E)-Ethyl 3-(4-((E)-2-(3-butoxyphenyl)-1-(1-(tetrahydro-2H-pyran-2-yl)-1H-indazol-5-yl)but-1-en-1-yl)phenyl)acrylate

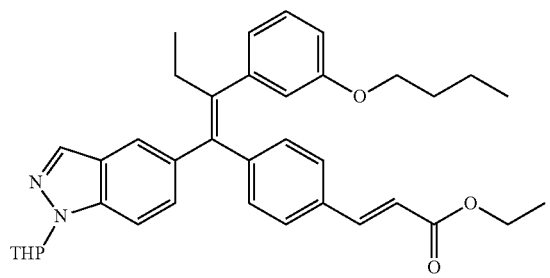

Potassium carbonate (53 mg, 0.38 mmol) was added to (E)-ethyl 3-(4-((E)-2-(3-hydroxyphenyl)-1-(1-(tetrahydro-2H-pyran-2-yl)-1H-indazol-5-yl)but-1-en-1-yl)phenyl)acrylate (101 mg, 0.19 mmol) in $CH_3CN$ (1 mL). After stirring for 15 min, iodobutane (24 µL, 0.21 mmol) was added. The reaction was stirred at rt for 15 h. Additional iodobutane (24 µL, 0.21 mmol) was added, and the reaction was stirred at 60° C. for 10 h and then at rt for 48 h. The reaction was diluted with dichloromethane and filtered through celite. The filtrate was concentrated and purified by silica gel chromatography (0-20% EtOAc in hexanes) to give 97 mg of (E)-ethyl 3-(4-((E)-2-(3-butoxyphenyl)-1-(1-(tetrahydro-2H-pyran-2-yl)-1H-indazol-5-yl)but-1-en-1-yl)phenypacrylate as a white foam. $^1$H NMR (400 MHz, DMSO-$d_6$): δ 8.12 (s, 1H), 7.73 (d, 1H), 7.64 (s, 1H), 7.49 (d, 1H), 7.41 (d, 1H), 7.24 (dd, 1H), 7.12 (t, 1H), 6.91 (d, 2H), 6.76 (d, 1H), 6.67-6.72 (m, 2H), 6.48 (d, 1H), 5.86 (d, 1H), 4.15 (q, 2H), 3.86-3.94 (m, 1H), 3.72-3.80 (m, 3H), 2.38-2.46 (m, 3H), 1.96-2.10 (m, 2H), 1.70-1.82 (m, 1H), 1.52-1.63 (m, 4H), 1.31-1.37 (m, 2H), 1.22 (t, 3H), 0.85-0.92 (m, 6H); LCMS: 495 [(M-THP+H)+H]$^+$.

Step 3: (E)-3-(4-((E)-2-(3-Butoxyphenyl)-1-(1H-indazol-5-yl)but-1-en-1-yl)phenyl)acrylic acid

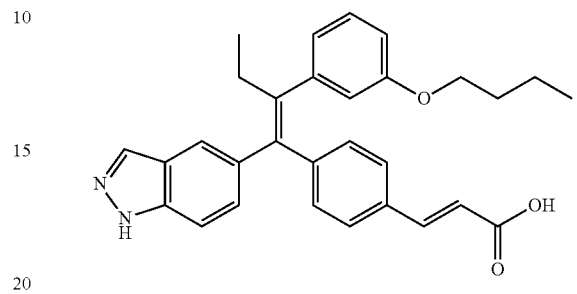

The title compound was prepared from (E)-ethyl 3-(4-((E)-2-(3-butoxyphenyl)-1-(1-(tetrahydro -2H-pyran-2-yl)-1H-indazol-5-yl)but-1-en-1-yl)phenypacrylate following General Procedures F and G. $^1$H NMR (400 MHz, DMSO-$d_6$): δ 13.11 (bs, 1H), 12.33 (bs, 1H), 8.08 (s, 1H), 7.64 (s, 1H), 7.54 (d, 1H), 7.43 (d, 1H), 7.37 (d, 2H), 7.10-7.17 (m, 2H), 6.91 (d, 2H), 6.75 (d, 1H), 6.66-6.72 (m, 2H), 6.37 (d, 1H), 3.78 (t, 2H), 2.43 (q, 2H), 1.52-1.60 (m, 2H), 1.29-1.38 (m, 2H), 0.85-0.92 (m, 6H); LCMS: 467 (M+H)$^+$.

Compound 97 was prepared following the procedure outlined for Compound 96.

Example 33

Preparation of Compound 98: (E)-3-(4-((E)-1-(1H-Indazol-5-yl)-2-(2-(methylsulfonyl)phenyl)but-1-en-1-yl)phenyl)acrylic acid Step 1: (E)-Ethyl 3-(4-((E)-2-(2-(methylthio)phenyl)-1-(1-(tetrahydro-2H-pyran-2-yl)-1H-indazol-5-yl)but-1-en-1-yl)phenyl)acrylate

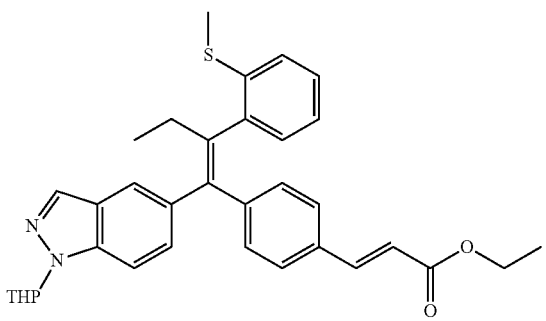

The title compound was prepared from Intermediate 3,2-iodothioanisole, and (E)-(4-(3-ethoxy-3-oxoprop-1-en-1-yl)phenyl)boronic acid following General Procedure C. $^1$H NMR (DMSO-$d_6$, 300 MHz): δ 8.14 (s, 1H), 7.75 (d, 1H), 7.72-7.65 (m, 1H), 7.44 (d, 1H), 7.35 (d, 2H), 7.29-7.24 (m, 1H), 7.22-7.11 (m, 3H), 7.09-7.03 (m, 1H), 7.01 (d, 2H), 6.44 (d, 1H), 5.85 (dd, 1H), 4.13 (q, 2H), 3.94-3.83 (m, 1H), 3.80-3.68 (m, 1H), 2.47-2.27 (m, 6H), 2.09-1.93 (m, 2H), 1.83-1.69 (m, 1H), 1.67-1.52 (m, 2H), 1.20 (t, 3H), 0.88 (t, 3H).

Step 2: (E)-Ethyl 3-(4-((E)-2-(2-(methylsulfonyl) phenyl)-1-(1-(tetrahydro-2,1-pyran-2-yl)-1H-indazol-5-yl)but-1-en-1-yl)phenyl)acrylate

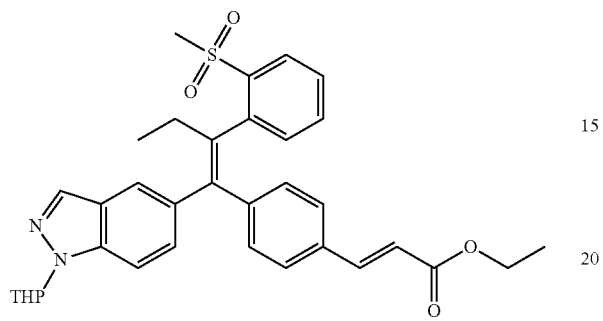

Potassium peroxymonosulfate (521 mg, 0.85 mmol) was added to a slurry of (E)-ethyl 3-(4-((E)-2-(2-(methylthio) phenyl)-1-(1-(tetrahydro-2H-pyran-2-yl)-1H-indazol-5-yl) but-1-en-1-yl)phenyl)acrylate (156 mg, 0.28 mmol) in MeOH:H$_2$O (1:1, 6 mL) at room temperature, and the reaction was stirred overnight. DCM and water were added, and the layers were separated. The aqueous layer was washed with DCM (×2). The organic layers were combined, washed with water, washed with brine, dried over Na$_2$SO$_4$, filtered, and concentrated. The crude material was purified on a silica gel column eluted with 0-50% ethyl acetate in hexane affording the title compound. $^1$H NMR (DMSO-d$_6$, 300 MHz): δ 8.15 (s, 1H), 7.91 (d, 1H), 7.77-7.71 (m, 2H), 7.49-7.46 (m, 3H), 7.41-7.31 (m, 4H), 7.01 (d, 2H), 6.45 (d, 1H), 5.87 (dd, 1H), 4.12 (q, 2H), 3.92-3.85 (m, 1H), 3.82-3.69 (m, 1H), 2.93 (s, 3H), 2.46-2.27 (m, 2H), 2.09-1.97 (m, 3H), 1.85-1.67 (m, 1H), 1.63-1.51 (m, 2H), 1.18 (t, 3H), 0.83 (t, 3H). LCMS: 501 [(M-THP+H)+H]$^+$.

Step 3: (E)-3-(4-((E)-1-(1H-Indazol-5-yl)-2-(2-(methylsulfonyl)phenyl)but-1-en-1-yl)phenyl)acrylic acid

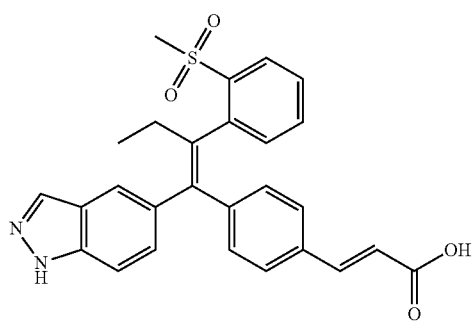

The title compound was prepared from (E)-ethyl 3-(4-((E)-2-(2-(methylsulfonyl)phenyl)-1-(1-(tetrahydro-2H-pyran-2-yl)-1H-indazol-5-yl)but-1-en-1-yl)phenyl)acrylate following General Procedures F & G. $^1$H NMR (DMSO-d$_6$, 300 MHz): δ 13.14 (br s, 1H), 12.29 (br s, 1H), 8.11 (d, 1H), 7.92 (dd, 1H), 7.71 (s, 1H), 7.66-7.54 (m, 2H), 7.53-7.44 (m, 2H), 7.42-7.33 (m, 3H), 7.26 (dd, 1H), 7.01 (d, 2H), 6.34 (d, 1H), 2.94 (s, 3H), 2.42-2.30 (m, 2H), 0.83 (t, 3H); LCMS: 473 (M+H)$^+$.

Example 34

Preparation of Compound 99: (E)-3-(4-((E)-1-(1H-Indazol-5-yl)-2-phenylbut-1-en-1-yl)phenyl)-2-methylacrylic acid Step 1: (E)-4-(2-Phenyl-1-(1-(tetrahydro-2H-pyran-2-yl)-1H-indazol-5-yl)but-1-en-1-yl)benzaldehyde

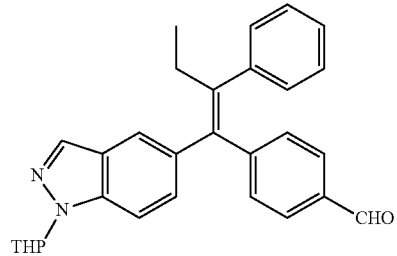

The title compound was prepared from Intermediate 3, iodobenzene, and (4-formylphenyl)boronic acid following General Procedure C. LCMS: 353 [(M-THP+H)+H]$^+$.

Step 2: (E)-Ethyl 2-methyl-3-(4-((E)-2-phenyl-1-(1-(tetrahydro-2H-pyran-2-yl)-1H-indazol-5-yl) but-1-en-1-yl)phenyl)acrylate

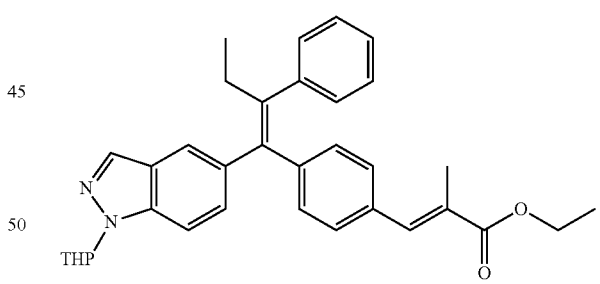

To a suspension of NaH (80 mg, 2 mmol, 60% dispersion in mineral oil) in THF (10 mL) at 0° C., ethyl 2-(diethoxyphosphoryl)propanoate (0.36 g, 1.5 mmol) was added. The reaction was stirred at 0° C. for 1 h, and then a THF solution of (E)-4-(2-phenyl-1-(1-(tetrahydro-2H-pyran-2-yl)-1H-indazol-5-yl)but-1-en-1-yl)benzaldehyde (0.44 g, 1 mmol) was added. The resulting mixture was gradually warmed to room temperature and stirred overnight. The reaction mixture was quenched with saturated ammonium chloride solution and extracted with EtOAc (2×100 mL). Combined organic layers were washed with water, brine, dried over sodium sulfate, filtered and concentrated to give the crude material as pale yellow oil. LCMS: 437 [(M-THP+H)+H]$^+$.

Step 3: (E)-3-(4-((E)-1-(1H-Indazol-5-yl)-2-phenyl-but-1-en-1-yl)phenyl)-2-methylacrylic acid

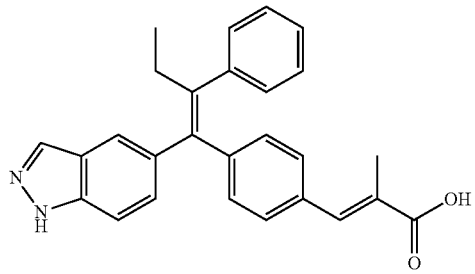

The title compound was prepared from (E)-ethyl 2-methyl-3-(4-((E)-2-phenyl-1-(1-(tetrahydro -2H-pyran-2-yl)-1H-indazol-5-yl)but-1-en-1-yl)phenyl)acrylate following General Procedures F & G. $^1$H NMR (300 MHz, DMSO-$d_6$): δ 13.11 (s, 1H), 12.55 (br, 1H), 8.08 (d, 1H), 7.65 (s, 1H), 7.53 (d, 1H), 7.42 (d, 1H), 7.21-7.11 (m, 8H), 6.90 (d, 2H), 2.40 (q, 2H), 1.92 (d, 3H), 0.87 (t, 3H); LCMS: 409 (M+H)$^+$.

Compounds 100 to 109 were prepared from the appropriate boronic acid or phosphonate following the procedures outlined for Compound 99 or General Procedures C, E, F & G.

Example 35

Preparation of Compound 110: (E)-Ethyl 3-(4-((E)-2-(2-chloro-4-fluorophenyl)-1-(1H-indazol -5-yl)but-1-en-1-yl)phenyl)acrylate hydrochloride Step 1: (E)-4-(2-(2-Chloro-4-fluorophenyl)-1-(1-(tetrahydro-2H-pyran-2-yl)-1,1-indazol-5-yl)but-1-en-1-yl)benzaldehyde

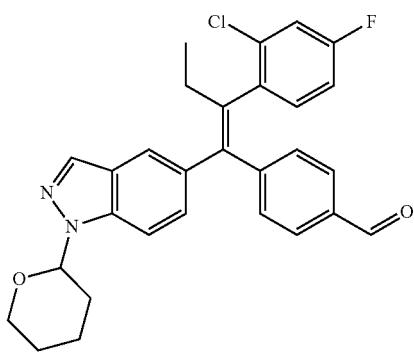

A round-bottom flask equipped with a magnetic stir bar, a reflux condenser, internal thermometer, and a N$_2$ inlet was charged with 5-(but-1-yn-1-yl)-1-(tetrahydro-2H-pyran-2-yl)-1H-indazole (50.0 g, 197 mmol; Intermediate 3), bis(pinacolato)diboron (50.4 g, 199 mmol), and anhydrous 2-methyltetrahydrofuran (393 mL) followed by Pt(PPh$_3$)$_4$ (1.83 g, 1.5 mmol). This mixture was degassed with three vacuum/N$_2$ cycles, heated at 83° C. (internal temperature; oil bath at 95° C.) for 5 h under N$_2$, and then allowed to cool to room temperature. 2-Methyltetrahydrofuran (393 mL), cesium carbonate (128.1 g, 393 mmol), and water (11.8 mL, 1.5% v/v) were added, and the reaction was cooled to 4° C. 4-Iodobenzaldehyde (45.6 g, 197 mmol) and PdCl$_2$(PPh$_3$)$_2$ (6.90 g, 9.8 mmol) were added, and the reaction was degassed with three vacuum/N$_2$ cycles. The mixture was allowed to warm to room temperature and stirred overnight. Aqueous KOH solution (4M, 275 mL, 1100 mmol) and 2-chloro-4-fluoroiodobenzene (70.6 g, 275 mmol) were added. The reaction was degassed with 3 vacuum/N$_2$ cycles, heated at 75° C. (internal temperature; oil bath at 90° C.) for 7 h under N$_2$, and then allowed to cool to room temperature. The layers were separated, and the organic layer was washed with brine (800 mL), dried over sodium sulfate, filtered, and concentrated. The crude product was purified by silica gel chromatography (0-20% ethyl acetate in hexanes) to give the title compound (82.6 g, 7:1 mixture of regioisomers) as a pale yellow foam. Data for major isomer; (E)-4-(2-(2-chloro-4-fluorophenyl)-1-(1-(tetrahydro-2H-pyran-2-yl)-1H-indazol -5-yl)but-1-en-1-yl)benzaldehyde: $^1$H NMR (300 MHz, DMSO-$d_6$): δ 9.82 (s, 1H), 8.15 (s, 1H), 7.78-7.71 (m, 2H), 7.61 (d, 2H), 7.43-7.27 (m, 3H), 7.15 (m, 3H), 5.86 (dd, 1H), 3.93-3.85 (m, 1H), 3.79-3.68 (m, 1H), 2.44-2.36 (m, 3H), 2.10-1.96 (m, 2H), 1.81-1.67 (m, 1H), 1.63-1.53 (m, 2H), 0.92 (t, 3H); LCMS: 405 [(M-THP+H)+H]$^+$.

Step 2: (E)-Ethyl 3-(4-((E)-2-(2-chloro-4-fluorophenyl)-1-(1-(tetrahydro-2H-pyran-2-yl)-1H-indazol -5-yl)but-1-en-1-yl)phenyl)acrylate

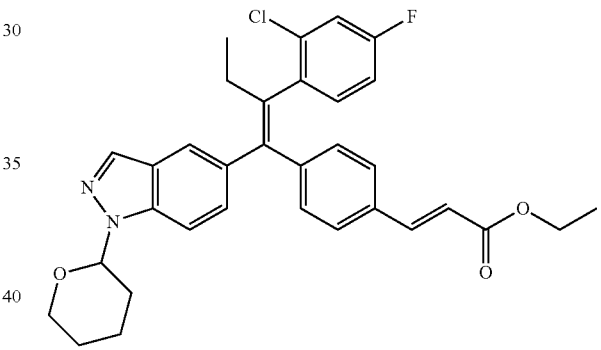

A round-bottom flask equipped with a magnetic stir bar, an addition funnel, and a N$_2$ inlet was charged with (E)-4-(2-(2-chloro-4-fluorophenyl)-1-(1-(tetrahydro-2H-pyran-2-yl)-1H-indazol-5-yl)but-1-en-1-yl)benzaldehyde (82.6 g, 169 mmol), triethylphosphonoacetate (40.6 mL, 203 mmol), lithium chloride (14.5 g, 338 mmol), and anhydrous acetonitrile (338 mL). The reaction was cooled to 0° C. and then degassed with three vacuum/N$_2$ cycles. A solution of DBU (27.8 mL, 186 mmol) in acetonitrile (60 mL) was added dropwise over 35 min, and then the ice water bath was removed. The reaction was stirred at room temperature for 1 h, concentrated, and then partitioned between dichloromethane (250 mL) and H$_2$O (250 mL). The layers were separated, and the organic layer was washed with brine (400 mL), dried over sodium sulfate, filtered, and concentrated. The crude product was passed through a silica gel column (300 g, 20% ethyl acetate in hexanes) and concentrated to give the title compound (89.6 g) as a pale yellow foam. $^1$H NMR (300 MHz, DMSO-$d_6$): δ 8.14 (s, 1H), 7.75 (d, 1H), 7.50-7.33 (m, 6H), 7.27 (dt, 1H), 7.14 (dt, 1H), 6.95 (d, 2H), 6.48 (d, 1H), 5.86 (dd, 1H), 4.14 (q, 2H), 3.94-3.86 (m, 1H), 3.78-3.70 (m, 1H), 2.45-2.34 (m, 3H), 2.06-1.95 (m, 2H), 1.78-1.67 (m, 1H), 1.62-1.53 (m, 2H), 1.19 (t, 3H), 0.90 (t, 3H); LCMS: 475 [(M-THP+H)+H]$^+$.

Step 3: (E)-Ethyl 3-(4-((E)-2-(2-chloro-4-fluorophenyl)-1-(1H-indazol-5-yl)but-1-en-1-yl)phenyl)acrylate hydrochloride

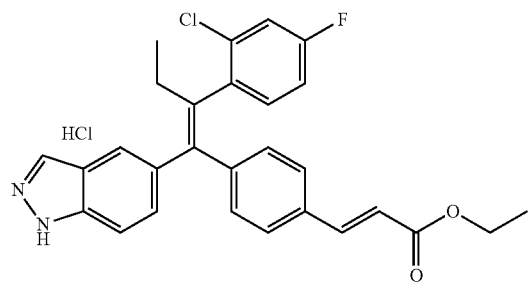

A round-bottom flask equipped with a magnetic stir bar was charged with (E)-ethyl 3-(4-((E)-2-(2-chloro-4-fluorophenyl)-1-(1-(tetrahydro-2H-pyran-2-yl)-1H-indazol-5-yl)but-1-en-1-yl)phenyl)acrylate (255.9 g, 457.8 mmol) and a solution of HCl (732 mL, 1.25 M in ethyl alcohol). The reaction was heated at 80° C. for 2.5 h, allowed to cool to room temperature, and then concentrated to an orange gel. tert-Butyl methyl ether (2.3 L) was added. After stirring for 5 min, solids began to precipitate. The mixture was stirred at room temperature for 2 h and then filtered. The solids were washed with MTBE (700 mL) and dried to give the title compound (193 g) as an off-white solid. $^1$H NMR (DMSO-$d_6$): δ 8.11 (s, 1H), 7.69 (s, 1H), 7.57-7.50 (m, 2H), 7.45-7.33 (m, 4H), 7.21-7.10 (m, 2H), 6.96 (d, 2H), 6.48 (d, 1H), 4.14 (q, 2H), 2.38 (q, 2H), 1.19 (t, 3H), 0.90 (t, 3H); LCMS: 475 (M+H)$^+$.

Example 36

Preparation of Compound III: (E)-3-(4-0E)-2-(2-Chloro-4-fluorophenyl)-1-(1H-indazol -5-yl)but-1-en-1-yl)phenyl)acrylic acid

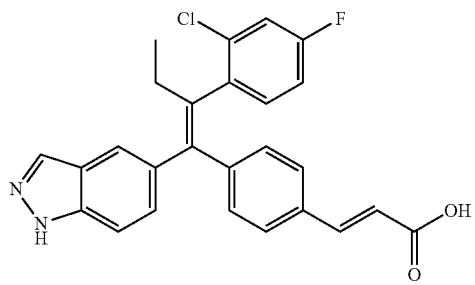

A round-bottom flask equipped with a magnetic stir bar was charged with (E)-ethyl 3-(4-((E)-2-(2-chloro-4-fluorophenyl)-1-(1H-indazol-5-yl)but-1-en-1-yl)phenyl)acrylate hydrochloride (198.5 g, 388 mmol; Compound 110) and ethyl alcohol (517 mL). A solution of LiOH (27.9 g, 1164 mmol) in water (388 mL) was added, and the mixture was stirred at room temperature overnight. The ethyl alcohol was removed by rotary evaporation, and the remaining solution was cooled to 0° C. and acidified with 2M aqueous HCl to pH 3. Dichloromethane (500 mL) was added, the mixture was stirred, and then the layers were separated. The organic layer was washed with water, washed with brine, dried over sodium sulfate, filtered, and concentrated. The crude product was passed through a silica column (800 g, 5% MeOH in DCM) and concentrated. The product was then dissolved in DCM (400 mL), and acetonitrile (500 mL) was added. Approximately 200 mL of DCM was removed by rotary evaporation (solids began to precipitate). Acetonitrile (550 mL) was added followed by water (25 mL). The mixture was stirred at room temperature for 2 h. The solvent was decanted, and then acetonitrile:DCM (10:1; 550 mL) was added. The mixture stirred at room temperature for 1.5 h, the solvent was again decanted, and then acetonitrile:DCM (10:1; 550 mL) was added. The mixture was again stirred at room temperature for 1.5 h and then filtered. The solids were resuspended in acetonitrile:DCM (10:1; 550 mL), stirred at room temperature for 1.5 h, filtered, and washed to give the title compound (123.9 g) as an off-white powder. $^1$H NMR (DMSO-$d_6$): δ 13.12 (s, 1H), 12.34 (br, 1H), 8.11 (d, 1H), 7.69 (s, 1H), 7.56 (d, 1H), 7.44-7.33 (m, 5H), 7.21-7.10 (m, 2H), 6.96 (d, 2H), 6.38 (d, 1H), 2.34 (q, 2H), 0.90 (t, 3H); LCMS: 447 (M+H)$^+$.

Example 37

Preparation of Compound 112: (E)-Ethyl 3-(4-((E)-2-(2,4-dichlorophenyl)-1-(1H-indazol -5-yl)but-1-en-1-yl)phenyl)acrylate

Step 1: (E)-4-(2-(2,4-Dichlorophenyl)-1-(1-(tetrahydro-2H-pyran-2-yl)-1H-indazol-5-yl)but-1-en-1-yl)benzaldehyde

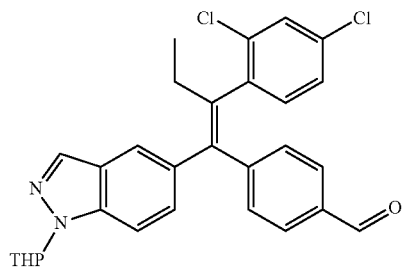

A round-bottom flask equipped with a magnetic stir bar, a reflux condenser, and a $N_2$ inlet was charged with 5-(but-1-yn-1-yl)-1-(tetrahydro-2H-pyran-2-yl)-1H-indazole (20.0 g, 78.6 mmol; Intermediate 3), bis(pinacolato)diboron (20.17 g, 79.4 mmol), tetrakis(triphenylphosphine)platinum (0) (0.98 g, 0.8 mmol), and anhydrous 1,4-dioxane (160 mL). This mixture was degassed with three vacuum/$N_2$ cycles and refluxed for 4 h. The solution was then allowed to cool to room temperature, and 4-iodobenzaldehyde (18.25 g, 78.6 mmol), trans-dichloro(triphenylphosphine)palladium (II) (5.52 g, 7.9 mmol), cesium carbonate (51.24 g, 157.3 mmol), and 1,4-dioxane (160 mL) were added. This mixture was degassed with three vacuum/$N_2$ cycles, and then water (4.7 mL) was added. This mixture was stirred at room temperature for 6 h. 2,4-Dichloroiodobenzene (12.8 mL, 94.4 mmol) and 6M aqueous KOH (62.9 mL) were added, and the mixture was degassed with three vacuum/$N_2$ cycles and refluxed for 4 h. Upon completion, the reaction mixture was filtered through a Celite/silica pad and washed with EtOAc. The filtrate was washed with water (600 mL), washed with brine (300 mL), dried over sodium sulfate, filtered, and concentrated. The crude product was purified by silica gel chromatography (0-20% ethyl acetate in hexanes) to give the title compound (27.2 g, 7:1 mixture of regioisomers) as a yellow foam. Data for major regioisomer: $^1$H NMR (400 MHz, DMSO-d$_6$): δ 9.83 (s, 1H), 8.16 (s, 1H), 7.77 (d, 1H), 7.73 (s, 1H), 7.65 (d, 2H), 7.53 (d, 1H), 7.41-7.36 (m, 2H), 7.31-7.28 (m, 1H), 7.17 (d, 2H), 5.86 (dd, 1H), 3.92-3.86 (m, 1H), 3.78-3.71 (m, 1H), 2.47-2.38 (m, 3H), 2.10-1.96 (m, 2H), 1.81-1.71 (m, 1H), 1.64-1.58 (m, 2H), 0.94 (t, 3H); LCMS: 421 [(M-THP+H)+H]$^+$.

Step 2: (E)-Ethyl 3-(4-((E)-2-(2,4-dichlorophenyl)-1-(1-(tetrahydro-2H-pyran-2-yl)-1H-indazol-5-yl)but-1-en-1-yl)phenyl)acrylate

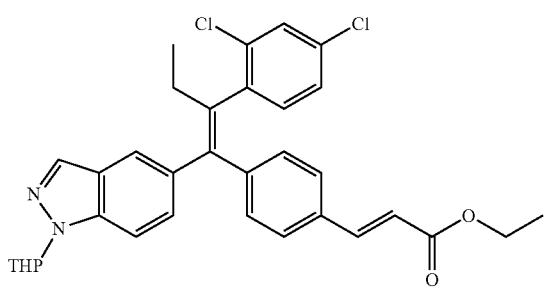

A round-bottom flask equipped with a magnetic stir bar, a rubber septum, and a N$_2$ inlet was charged with (E)-4-(2-(2,4-dichlorophenyl)-1-(1-(tetrahydro-2H-pyran-2-yl)-1H-indazol-5-yl)but-1-en-1-yl)benzaldehyde (26.7 g, 52.8 mmol), triethylphosphonoacetate (12.7 mL, 63.4 mmol), lithium chloride (4.53 g, 105.7 mmol), and anhydrous acetonitrile (106 mL). A solution of DBU (8.7 mL, 58.1 mmol) in ACN (27 mL) was slowly added dropwise via addition funnel. The resulting mixture was stirred at room temperature for 4 h. Upon completion, the reaction was concentrated and redissolved in DCM. This solution was washed with, water (300 mL), washed with brine (250 mL), dried over sodium sulfate, filtered and concentrated. The crude product was purified by silica gel chromatography (0-20% ethyl acetate in hexanes) to give the title compound (29.0 g) as a pale yellow foam. $^1$H NMR (400 MHz, DMSO-d$_6$): δ 8.14 (s, 1H), 7.75 (d, 1H), 7.72 (s, 1H), 7.54 (d, 1H), 7.48 (d, 1H), 7.43 (d, 2H), 7.37-7.35 (m, 2H), 7.29-7.26 (m, 1H), 6.97 (d, 2H), 6.48 (d, 1H), 5.86 (dd, 1H), 4.14 (q, 2H), 3.91-3.86 (m, 1H), 3.77-3.71 (m, 1H), 2.48-2.35 (m, 3H), 2.06-1.96 (m, 2H), 1.78-1.71 (m, 1H), 1.62-1.55 (m, 2H), 1.22 (t, 3H), 0.90 (t, 3H); LCMS: 491 [(M-THP+H)+H]$^+$.

Step 3: (E)-Ethyl 3-(4-((E)-2-(2,4-dichlorophenyl)-1-(1H-indazol-5-yl)but-1-en-1-yl)phenyl)acrylate

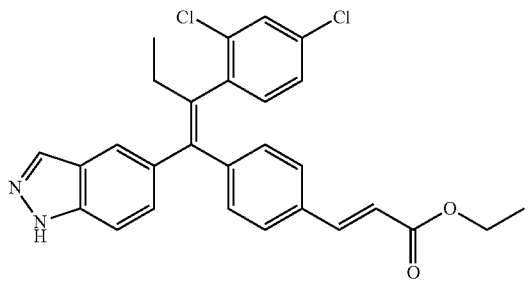

A solution of HCl (5.0 mL, 2.0 M in diethyl ether) was added to a solution of (E)-ethyl 3-(4-((E)-2-(2,4-dichlorophenyl)-1-(1-(tetrahydro-2H-pyran-2-yl)-1H-indazol-5-yl)but-1-en-1-yl)phenyl)acrylate (3.0 g, 5.2 mmol) in ethyl alcohol (25 mL) at room temperature. The resulting mixture was heated at 70° C. for 2 h. Upon completion, the mixture was cooled down to room temperature and concentrated to give a pale yellow solid. This crude material was dissolved in DCM and washed with water (50 mL), washed with brine (50 mL), dried over sodium sulfate, filtered, and concentrated. The crude product was purified by silica gel chromatography (0-100% ethyl acetate in hexanes) to give the title compound (2.37 g) as a pale yellow solid. $^1$H NMR (400 MHz, DMSO-d$_6$): δ 13.17 (s, 1H), 8.11 (s, 1H), 7.69 (s, 1H), 7.58-7.52 (m, 2H), 7.48 (d, 1H), 7.43 (d, 2H), 7.36-7.32 (m, 2H), 7.19 (dd, 1H), 6.97 (d, 2H), 6.49 (d, 1H), 4.15 (q, 2H), 2.39 (q, 2H), 1.22 (t, 3H), 0.90 (t, 3H); LCMS: 491 (M+H)$^+$.

Example 38

Preparation of Compound 113: (E)-3-(4-0E)-2-(2,4-Dichlorophenyl)-1-(1H-indazol-5-yl)but-1-en-1-yl)phenyl)acrylic acid

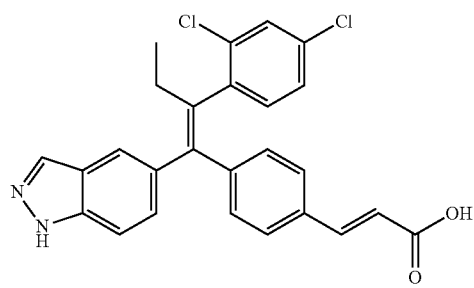

A solution of LiOH (0.23 g, 9.6 mmol) in water (3.2 mL) was added to a solution of (E)-ethyl 3-(4-((E)-2-(2,4-dichlorophenyl)-1-(1H-indazol-5-yl)but-1-en-1-yl)phenyl)acrylate (2.37 g, 4.8 mmol; Compound 112) in EtOH (20 mL) at room temperature. The resulting mixture was stirred overnight. Upon completion, 1N aqueous HCl was added until the pH was 3. The mixture was diluted with water and extracted with ethyl acetate (2×25 mL). The combined organic layers were washed with water (50 mL), washed with brine (50 mL), dried over sodium sulfate, filtered, and concentrated. The crude product was purified on a preparative reversed-phased HPLC column using 80-95% acetonitrile in water in the presence of 0.1% TFA to give the title compound (1.3 g) as an off-white solid. $^1$H NMR (400 MHz, DMSO-d$_6$): δ 13.11 (s, 1H), 12.36 (br, 1H), 8.11 (d, 1H), 7.69 (s, 1H), 7.57-7.53 (m, 2H), 7.44-7.35 (m, 5H), 7.19 (dd, 1H), 6.97 (d, 2H), 6.39 (d, 1H), 2.39 (q, 2H), 0.90 (t, 3H); LCMS: 463 (M+H)$^+$.

Compounds 114 to 139 were prepared from alkynyl-indazole intermediates following General Procedures D, E, F, & G. The alkynyl-indazole intermediates have either i) been described herein or ii) were prepared from known or commercially available halo-indazoles following General Procedures A & B.

Example 39

Preparation of Intermediate 45: (E)-Ethyl 3-(44(Z)-1-(1-(tetrahydro-2H-pyran-2-yl)-1H-indazol-5-yl)-2-(4,4,5,5-tetramethyl-1,3,2-dioxaborolan-2-yl)but-1-en-1-yl)phenyl)acrylate Step 1: (E)-Ethyl 3-(4-iodophenyl)acrylate

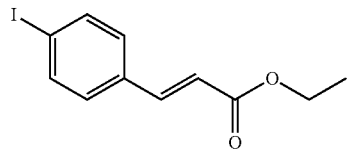

N-Iodosuccinimide (2.5 g, 11 mmol) was added to a suspension of 4-(E-3-ethoxy-3-oxo-1-propen-1-yl)phenylboronic acid (2.2 g, 10 mmol) in $CH_3CN$ (50 mL) at room temperature. The reaction was covered with foil, stirred for ~26 hours, and then diluted with EtOAc. The resulting mixture was washed with water (2×100 mL), washed with sodium thiosulfate (100 mL), dried ($MgSO_4$), filtered, and concentrated. The crude material was purified by silica gel chromatography (0-50% EtOAc in hexanes) to give 2.6 g of (E)-ethyl 3-(4-iodophenyl)acrylate as a yellow oil. $^1$H NMR (400 MHz, DMSO-$d_6$): δ 7.79 (d, 2H), 7.60 (d, 1H), 7.53 (d, 2H), 6.68 (d, 1H), 4.19 (q, 2H), 1.26 (t, 3H); LCMS: 303 (M+H)$^+$.

Step 2: (E)-Ethyl 3-(44(Z)-1-(1-(tetrahydro-2H-pyran-2-yl)-1H-indazol-5-yl)-2-(4,4,5,5-tetramethyl-1,3,2-dioxaborolan-2-yl)but-1-en-1-yl)phenyl)acrylate

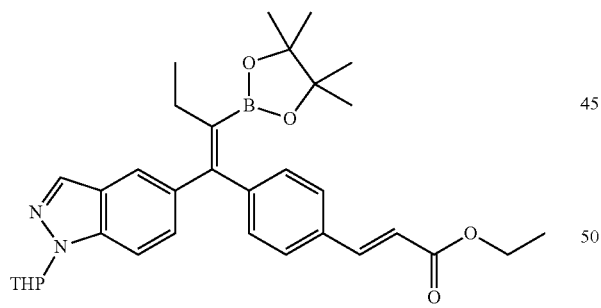

The title compound was be prepared from Intermediate 3 and (E)-ethyl 3-(4-iodophenyl)acrylate following General Procedure D, Steps 1-2. $^1$H NMR (400 MHz, DMSO-$d_6$): δ 8.09 (s, 1H), 7.70 (d, 1H), 7.58-7.63 (m, 3H), 7.49 (s, 1H), 7.11 (d, 3H), 6.58 (d, 1H), 5.84 (dd, 1H), 4.18 (q, 2H), 3.86-3.91 (m, 1H), 3.70-3.77 (m, 1H), 2.36-2.48 (m, 1H), 2.08-2.15 (m, 2H), 1.95-2.08 (m, 2H), 1.70-1.81 (m, 1H), 1.56-1.62 (m, 2H), 1.25 (t, 3H), 1.12 (s, 12H), 1.01 (t, 3H); LCMS: 473 [(M-THP+H)+H]$^+$.

Compounds 140 to 144 were prepared from Intermediate 45 following General Procedures D (Step 3; $K_2CO_3$ modification), F, & G.

Example 40

Preparation of Compound 145: (E)-3-(4-((E)-2-(2-Chlorophenyl)-1-(1-methyl-1H-indazol-5-yl)but-1-en-1-yl)phenyl)acrylic acid

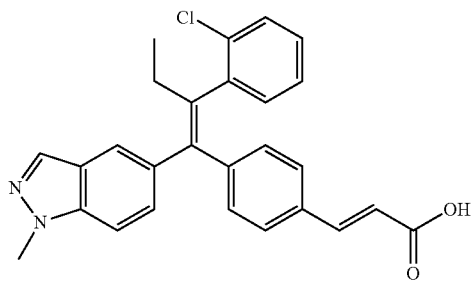

To a mixture of (E)-3-(4-((E)-2-(2-chlorophenyl)-1-(1H-indazol-5-yl)but-1-en-1-yl)phenyl)acrylic acid (80 mg, 0.19 mmol; Compound 14) and $Cs_2CO_3$ (0.15 g, 0.46 mmol) in DMF (3.8 mL) at room temperature, iodomethane (65 mg, 0.46 mmol) was added. The mixture was stirred at room temperature overnight, diluted with water, extracted with EtOAc, and concentrated to give the (E)-methyl 3-(4-((E)-2-(2-chlorophenyl)-1-(1-methyl-1H-indazol-5-yl)but-1-en-1-yl)phenyl)acrylate. This residue was redissolved in THF-MeOH (3.8 mL) and an aqueous solution of LiOH (89 mg, 3.7 mmol; dissolved in a minimum amount of water) was added at room temperature. The reaction mixture was stirred overnight, quenched with 1N HCl, extracted with EtOAc, dried over sodium sulfate, filtered and concentrated to give the crude material. This crude product was purified on a RP-C18 column using 50-100% acetonitrile in water in the presence of 0.1% TFA to afford the title compound. $^1$H NMR (300 MHz, DMSO-$d_6$): δ 12.28 (s, 1H), 8.07 (s, 1H), 7.67-7.64 (m, 2H), 7.48-7.11 (m, 8H), 6.95 (d, 2H), 6.35 (d, 1H), 4.05 (s, 3H), 2.36 (q, 2H), 0.90 (t, 3H). LCMS: 443 (M+H)$^+$.

Example 41

Preparation of Compound 146: (E)-3-(4-0E)-2-Cyclobutyl-1-(1-methyl-1H-indazol-5-yl)-2-phenylvinyl)phenyl)acrylic acid Step 1: (E)-Ethyl 3-(4-((E)-2-cyclobutyl-1-(1-methyl-1H-indazol-5-yl)-2-phenylvinyl)phenyl)acrylate

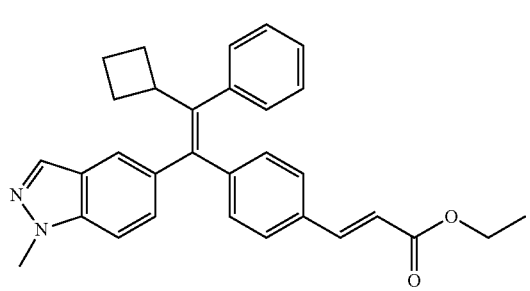

Iodomethane (80 mg, 0.84 mmol) was added to a mixture of (E)-ethyl 3-(4-((E)-2-cyclobutyl-1-(1H-indazol-5-yl)-2-phenylvinyl)phenypacrylate (0.25 g, 0.56 mmol; intermediate in the preparation of Compound 84), K$_2$CO$_3$ (0.12 g, 0.84 mmol), and DMF (5.6 mL) at room temperature. The resulting mixture was stirred overnight, diluted with water, and extracted with EtOAc. The extract was washed with water, washed with brine, dried over sodium sulfate, filtered, concentrated, and then purified on a silica gel column using 0-50% EtOAc in hexanes to afford the title compound. LCMS: 463 (M+H)$^+$.

Step 2: (E)-3-(4-0E)-2-Cyclobutyl-1-(1-methyl-1H-indazol-5-yl)-2-phenylvinyl)phenyl)acrylic acid

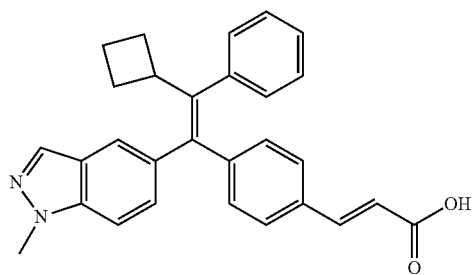

The title compound was prepared from (E)-ethyl 3-(4-((E)-2-cyclobutyl-1-(1-methyl-1H-indazol -5-yl)-2-phenylvinyl)phenyl)acrylate as described in General Procedure G. $^1$H NMR (400 MHz, DMSO-d$_6$): δ 12.26 (s, 1H), 8.06 (s, 1H), 7.68-7.61 (m, 2H), 7.37 (d, 1H), 7.31-7.12 (m, 8H), 6.92 (d, 2H), 6.36 (d, 1H), 4.09 (s, 3H), 3.46-3.39 (m, 1H), 1.84-1.76 (m, 4H), 1.63-1.52 (m, 1H), 1.37-1.32 (m, 1H); LCMS: 435 (M+H)$^+$.

Compound 147 was prepared following the procedure outlined for Compound 146.

Example 42

Preparation of Compound 148: (E)-3-(4-((E)-2-(2-Chloro-4-fluorophenyl)-1-(1-(difluoromethyl)-1H-indazol-5-yl)but-1-en-1-yl)phenyl)acrylic acid

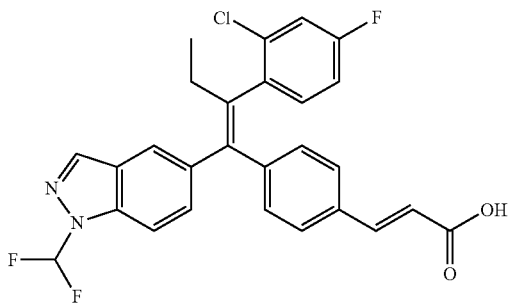

A solution of (E)-ethyl 3-(4-((E)-2-(2-chloro-4-fluorophenyl)-1-(1H-indazol-5-yl)but-1-en-1-yl)phenyl)acrylate (105, mg, 0.22 mmol; freebase of Compound 110) in DMF (1 mL) was added to a suspension of sodium hydride (11 mg, 0.27 mmol) in DMF (1 mL). The mixture was stirred at room temperature for 1 h, and then difluoroiodomethane was bubbled in for 10 min. The reaction mixture was heated at 80° C. for 3 h and cooled to room temperature. Difluoroiodomethane was bubbled in for additional 10 mM, and the mixture was heated for an additional 1.5 h. The reaction mixture was cooled to room temperature, diluted with ethyl acetate (50 mL), washed (2×25 mL H$_2$O), dried (Na$_2$SO$_4$), and concentrated under reduced pressure. The crude material was purified on a silica gel column to yield a mixture containing the desired intermediate. LCMS: 525(M+H)$^+$. Following General Procedure G, this intermediate gave the title compound. $^1$H NMR (300 MHz, DMSO-d$_6$): δ 8.91 (s, 1H), 8.17 (t, 1H), 7.77 (s, 1H), 7.74 (d, 1H), 7.45-7.35 (m, 5H), 7.20 (dd, 1H), 7.15 (dt, 1H), 7.00 (d, 2H), 6.38 (d, 2H), 2.41 (q, 2H), 0.92 (t, 3H); LCMS: 497 (M+H)$^+$.

Example 43

3×ERE MCF-7 Reporter Assay

MCF7 cells were maintained in RPMI 1640 supplemented with 10% FCS. Transcriptional assays were performed by seeding 100 μL of cells at a density of 250,000 cells/mL into 96-well cell culture plates in RPMI 1640 supplemented with 10% charcoal stripped serum and allowed to attach overnight. Cells were transiently transfected using Lipofectin (Life Technologies) according to the manufacturer's protocol. Triplicate transfections were performed using 300 ng 3×ERE-TK-Luc (reporter vector), 50 ng CMVpRL (normalization vector), and 130 ng pCMX (filler DNA). Transfected cells were incubated overnight then treated with ligand. For ER agonist assays, the compounds were serially diluted and 50 μL of compound plus RPMI 1640 supplemented with charcoal stripped serum was added to the cells. For ER antagonist assays, the compounds were serially diluted and 50 μL of compound with RPMI plus 17β-estradiol supplemented with charcoal stripped serum were added to the cells. The final 17β-estradiol concentration used in the antagonist assays was 0.1 nM. Following 24 hour incubation the medium was removed and the cells were lysed in 40 μL of lysis buffer (25 mM Tris Phosphate, 2 mM CDTA, 10% Glycerol, 0.5% Triton X-100, 2 mM DTT). Firefly luciferase activity was measured immediately following the addition of 40 μL luciferase buffer (20 mM tricine, 0.1 mM EDTA, 1.07 mM (MgCO$_3$)$_4$ Mg(OH)$_2$.5H$_2$O, 2.67 mM MgSO$_4$, 33.3 mM DTT, 270 μM Coenzyme A, 470 μM luciferin, 530 μM ATP). Renilla luciferase was measured following the addition of 40 μL colelenterazine buffer (1.1 M NaCl, 2.2 mM Na$_2$EDTA, 0.22 M KxPO$_4$ (pH 5.1), 0.44 mg/mL BSA, 1.3 mM NaN$_3$, 1.43 μM coelenterazine, final pH adjusted to 5.0).

Example 44

Breast Cancer Cell Viability Assays

MCF-7 cells were adjusted to a concentration of 20,000 cells per mL in RPMI containing 10% FBS and 20 mM HEPES. 16 microliters of the cell suspension (320 cells) was added to each well of a 384 well plate, and the cells were incubated overnight to allow the cells to adhere. The following day an eleven point, serial semilog dilution of each compound was added to the cells in 16 μL at a final concentration ranging from 0.3-0.000003 μM. After 5 days' compound exposure, 16 μL of CellTiter-GLo (Promega, Madison Wis.) was added to the cells the relative luminescence units (RLUs) of each well was determined CellTiter-Glo added to 32 μL of medium without cells was used to obtain a background value. The Percent viability of each sample was determined as follows: (RLU sample-RLU background/RLU untreated cells-RLU background)×100=% viability.

Viability effects in additional ER+ breast cancer cell lines, including BT474, CAMA1, MDA-MB-361, ZR-75-1, T47D, can be profiled in assays similar to Example 44.

Example 45

Breast Cancer Cell ER-α in Cell Western Assay (SP1)

MCF-7 cells were adjusted to a concentration of 200,000 cells per mL in RPMI containing 10% charcoal-stripped FBS and 20 mM HEPES. 16 microliters of the cell suspension (3200 cells) was added to each well of a poly-D-lysine 384 well plate, and the cells were incubated overnight to allow the cells to adhere. The following day an eleven point, serial semilog dilution of each compound was added to the cells in 16 μL at a final concentration ranging from 0.3-0.000003 μM. At 4 or 24 hr post compound addition, the cells were fixed (10% formalin in PBS) for 20 minutes. Cells were permeablized in PBS 0.1% Triton and blocked with LICOR blocking buffer (50 μl/well, 90′). The wells were then incubated overnight at 4° C. with SP1 rabbit monoclonal Ab (Thermo Scientific) diluted 1:1000 in LICOR blocking buffer/0.1% Tween-20. Wells which were treated with blocking buffer with Tween but no antibody were used as a background control. Wells were washed with 0.1% Tween-20/PBS and then incubated in goat anti-rabbit IRDye™ 800CW (LICOR Inc.; 1:1000) and DRAQ5 DNA dye (1:2000 for 2 mM stock) diluted in LICOR blocking buffer containing 0.1% Tween-20 and 0.01% SDS for 60 minutes. Cells were washed (50 μl/well, 5′ each) in 0.1% Tween-20/PBS. Plates were scanned on a LICOR Odyssey infrared imaging system. Integrated intensities in the 800 nm channel and 700 nm channel were measured to determine levels of ER and DNA respectively. Percent ER levels were determined as follows: (Integrated intensity 800 nm sample/integrated intensity 700 nm sample)/(Integrated intensity 800 nm untreated cells/integrated intensity 700 nm untreated cells)×100=%ER levels.

Effects on steady state levels of ER-α in additional ER+ breast cancer cell lines, including BT474, CAMA1, MDA-MB-361, ZR-75-1, T47D, can be profiled in assays similar to Example 45.

Illustrative biological data for representative compounds disclosed herein is presented in the following table:

TABLE 7

| Compound | MCF7 Viability Assay $IC_{50}$ | MCF7 Viability Assay Max Response | ER-α In Cell Western Assay (SP1) $IC_{50}$ | ER-α In Cell Western Assay (SP1) Max Response |
|---|---|---|---|---|
| 1 | A | + | A | ++ |
| 2 | A | ++ | A | ++ |
| 3 | A | ++ | A | ++ |
| 4 | A | ++ | A | ++ |
| 5 | A | ++ | A | ++ |
| 6 | B | ++ | A | ++ |
| 7 | A | ++ | A | ++ |
| 8 | B | ++ | A | ++ |
| 9 | A | ++ | A | ++ |
| 10 | A | ++ | A | ++ |
| 11 | A | ++ | A | ++ |
| 12 | A | ++ | A | ++ |
| 13 | A | ++ | A | ++ |
| 14 | A | ++ | A | ++ |
| 15 | A | ++ | A | ++ |
| 16 | A | ++ | A | ++ |
| 17 | A | ++ | A | ++ |
| 18 | A | ++ | A | ++ |
| 19 | A | ++ | A | ++ |
| 20 | A | ++ | A | ++ |
| 21 | A | ++ | A | ++ |
| 22 | A | ++ | A | ++ |
| 23 | A | ++ | A | ++ |
| 24 | A | ++ | A | ++ |
| 25 | A | ++ | A | ++ |
| 26 | A | ++ | A | ++ |
| 27 | A | ++ | A | ++ |
| 28 | A | ++ | A | ++ |
| 29 | A | ++ | A | ++ |
| 30 | A | ++ | A | ++ |
| 31 | A | ++ | A | ++ |
| 32 | A | ++ | A | ++ |
| 33 | A | ++ | A | ++ |
| 34 | A | ++ | A | ++ |
| 35 | A | ++ | A | ++ |
| 36 | A | ++ | A | ++ |
| 37 | A | ++ | A | ++ |
| 38 | B | ++ | B | ++ |
| 39 | B | ++ | B | ++ |
| 40 | B | ++ | B | ++ |
| 41 | A | ++ | A | ++ |
| 42 | A | ++ | A | ++ |
| 43 | A | ++ | A | ++ |
| 44 | A | ++ | A | ++ |
| 45 | A | ++ | A | ++ |
| 46 | B | + | B | ++ |
| 47 | A | ++ | A | ++ |
| 48 | A | ++ | A | ++ |
| 49 | A | ++ | A | ++ |
| 50 | A | ++ | A | ++ |
| 51 | A | ++ | A | ++ |
| 52 | A | ++ | A | ++ |
| 53 | A | ++ | A | ++ |
| 54 | A | ++ | A | ++ |
| 55 | A | ++ | A | ++ |
| 56 | A | ++ | A | ++ |
| 57 | A | ++ | A | ++ |
| 58 | A | ++ | A | ++ |
| 59 | A | ++ | A | ++ |
| 60 | A | ++ | A | ++ |
| 61 | A | ++ | A | ++ |
| 62 | A | ++ | A | ++ |
| 63 | A | ++ | A | ++ |
| 64 | A | ++ | A | ++ |
| 65 | A | ++ | A | ++ |
| 66 | A | ++ | A | ++ |
| 67 | A | ++ | A | ++ |
| 68 | A | ++ | A | ++ |
| 69 | A | ++ | A | ++ |
| 70 | A | ++ | A | ++ |
| 71 | A | ++ | A | ++ |
| 72 | A | ++ | A | ++ |
| 73 | A | ++ | A | ++ |
| 74 | A | ++ | A | ++ |
| 75 | A | ++ | A | ++ |
| 76 | A | ++ | A | ++ |
| 77 | A | ++ | A | ++ |
| 78 | A | ++ | A | ++ |
| 79 | A | ++ | A | ++ |
| 80 | B | ++ | A | ++ |
| 81 | B | ++ | A | ++ |
| 82 | A | ++ | A | ++ |
| 83 | A | ++ | A | ++ |
| 84 | A | ++ | A | ++ |
| 85 | A | ++ | A | ++ |
| 86 | A | ++ | A | ++ |
| 87 | A | ++ | A | ++ |
| 88 | A | ++ | A | ++ |
| 89 | A | ++ | A | ++ |
| 90 | A | + | A | ++ |
| 91 | A | + | − | − |
| 92 | A | + | − | − |
| 93 | A | ++ | A | ++ |
| 94 | B | ++ | A | ++ |

TABLE 7-continued

| Compound | MCF7 Viability Assay IC$_{50}$ | MCF7 Viability Assay Max Response | ER-α In Cell Western Assay (SP1) IC$_{50}$ | ER-α In Cell Western Assay (SP1) Max Response |
|---|---|---|---|---|
| 95 | A | ++ | A | ++ |
| 96 | A | ++ | A | ++ |
| 97 | A | ++ | A | ++ |
| 98 | A | ++ | A | ++ |
| 99 | A | ++ | A | ++ |
| 100 | A | ++ | A | ++ |
| 101 | A | ++ | A | ++ |
| 102 | A | ++ | A | ++ |
| 103 | B | ++ | A | ++ |
| 104 | B | ++ | A | ++ |
| 105 | A | ++ | A | ++ |
| 106 | A | ++ | A | ++ |
| 107 | B | ++ | A | ++ |
| 108 | A | ++ | A | ++ |
| 109 | A | ++ | A | ++ |
| 110 | A | + | A | ++ |
| 111 | A | ++ | A | ++ |
| 112 | A | + | A | ++ |
| 113 | A | ++ | A | ++ |
| 114 | A | ++ | A | ++ |
| 115 | A | ++ | A | ++ |
| 116 | A | ++ | A | ++ |
| 117 | A | ++ | A | ++ |
| 118 | A | ++ | A | ++ |
| 119 | A | ++ | A | ++ |
| 120 | A | ++ | A | ++ |
| 121 | A | ++ | A | ++ |
| 122 | A | ++ | A | ++ |
| 123 | A | ++ | A | ++ |
| 124 | A | ++ | A | ++ |
| 125 | A | ++ | A | ++ |
| 126 | A | ++ | A | ++ |
| 127 | B | + | B | + |
| 128 | A | ++ | A | ++ |
| 129 | A | ++ | A | ++ |
| 130 | A | ++ | A | ++ |
| 131 | B | ++ | B | ++ |
| 132 | A | ++ | A | ++ |
| 133 | B | + | B | ++ |
| 134 | A | ++ | A | ++ |
| 135 | A | ++ | A | ++ |
| 136 | A | ++ | A | ++ |
| 137 | A | ++ | A | ++ |
| 138 | A | ++ | A | ++ |
| 139 | A | ++ | A | ++ |
| 140 | A | ++ | A | ++ |
| 141 | B | ++ | A | ++ |
| 142 | A | ++ | A | ++ |
| 143 | B | ++ | A | ++ |
| 144 | A | ++ | A | ++ |
| 145 | A | ++ | A | ++ |
| 146 | A | ++ | A | ++ |
| 147 | A | ++ | A | ++ |
| 148 | A | ++ | A | ++ |

A = single IC$_{50}$ ≦ 100 nM;
B = single IC$_{50}$ > 100 nM;
+ = a single % value < 40%;
++ = a single % value ≧ 40%

Example 46

Ishikawa Uterine Cell Alkaline Phosphatase Assay

Subconfuent Ishikawa cells in a T225 are incubated 24 hours in an estrogen free basal medium (EFBM) consisting of DMEM:Ham's F-12 50:50 phenol red free basal medium containing 5% Charcoal Dextran treated FBS and 20 mM HEPES. Cells are plated the following day in EFBM in clear 384 well plates at a concentration of 2.5×105 cells per mL, 16 μl per well (4000 cells per well). A 12 point semilog dilution of each compound is carried out in DMSO and subsequently diluted in EFBM. An equal volume of compound in EFBM is added immediately after plating cells, and the cells are incubated for 3 days. The cells are fixed with 5% formalin, and rinsed with PBS. Alkaline Phosphatase substrate 4-Nitrophenyl phosphate disodium salt hexahydrate is added to a solution containing 2 mM MgCl$_2$, 1 M diethanolamine, and adjusted to pH 9.0. The substrate solution is added to the cell cultures (16 μL per well), and OD405 is measured in a multiwall plate spectrophotometer when the optical density at 405 nm wavelength of cells treated with 17β-estradiol in the concentration range of 1-30 nM reaches 1.0-1.2 absorbance units. Cells treated with DMSO alone serve as a background control. Percent activity in background subtracted samples is measured as follows: % activity=OD405 sample/OD405 max of 17/β-estradiol treated cells×100.

Example 47

Ovarian Cancer Cell Viability Assays

BG-1, cells were adjusted to a concentration of 20,000 cells per mL in RPMI containing 10% FBS and 20 mM HEPES. 16 microliters of the cell suspension (320 cells) was added to each well of a 384 well plate, and the cells were incubated overnight to allow the cells to adhere. The following day an eleven point, serial semilog dilution of each compound was added to the cells in 16 μL at a final concentration ranging from 0.3-0.000003 μM. After 5 days' compound exposure, 16 μL of CellTiter-GLo (Promega, Madison Wis.) was added to the cells the relative luminescence units (RLUs) of each well was determined CellTiter-Glo added to 32 μL of medium without cells was used to obtain a background value. The Percent viability of each sample was determined as follows: (RLU sample-RLU background/RLU untreated cells-RLU background)×100=% viability.

Viability effects in additional ER+ ovarian cancer cell lines, including A1847, SKOV3, SW626, A2780, can be profiled in assays similar to Example 47.

Example 48

Ovarian Cancer Cell ER-α in Cell Western Assay

BG-1 cells were adjusted to a concentration of 200,000 cells per mL in RPMI containing 10% charcoal-stripped FBS and 20 mM HEPES. 16 microliters of the cell suspension (3200 cells) was added to each well of a poly-D-lysine 384 well plate, and the cells were incubated overnight to allow the cells to adhere. The following day an eleven point, serial semilog dilution of each compound was added to the cells in 16 μL at a final concentration ranging from 0.3-0.000003 μM. At 4 or 24 hr post compound addition, the cells were fixed (10% formalin in PBS) for 20 minutes. Cells were permeablized in PBS 0.1% Triton and blocked with LICOR blocking buffer (50 μl/well, 90'). The wells were then incubated overnight at 4° C. with ER1D5 (Santa Cruz Biotechnology) diluted 1:100 in LICOR blocking buffer/0.1% Tween-20. Wells which were treated with blocking buffer with Tween but no antibody were used as a background control. Wells were washed with 0.1% Tween-20/PBS and then incubated in goat anti-mouse IRDye™ 800CW (LICOR Inc.; 1:1000) and DRAQ5 DNA dye (1:2000 for 2 mM stock) diluted in LICOR blocking buffer containing 0.1% Tween-20 and 0.01% SDS for 60 minutes. Cells were washed (50 μl/well, 5' each) in 0.1% Tween-20/PBS. Plates were scanned on a LICOR Odyssey infrared imaging system. Integrated intensities in the 800 nm channel and 700 nm channel were measured to determine levels of ER and DNA respectively. Percent ER levels were determined as follows: (Integrated intensity 800 nm sample/integrated intensity 700 nm sample)/(Integrated intensity 800 nm untreated cells/integrated intensity 700 nm untreated cells)×100=%ER levels.

Effects on steady state levels of ER-α in additional ER+ ovarian cancer cell lines, including A1847, SKOV3, SW626, A2780, can be profiled in assays similar to Example 48.

Other cancer cell lines contemplated for testing compounds described herein include: ER-positive endometrial cell lines (Ishikawa, ECC1, HEC-1, EnCa-101) and ER-positive cervical cell lines (Caski, HeLa, SiHa).

Example 49

Breast Cancer Model; Xenograft Assay (MCF-7)

Time release pellets containing 0.72 mg 17-β Estradiol were subcutaneously implanted into nu/nu mice. MCF-7 cells were grown in RPMI containing 10% FBS at 5% $CO_2$, 37° C. Cells were spun down and re-suspended in 50% RPMI (serum free) and 50% Matrigel at $1×10^7$ cells/mL. MCF-7 cells were subcutaneously injected (100 μL/animal) on the right flank 2-3 days post pellet implantation. Tumor volume (length×width$^2$/2) was monitored bi-weekly. When tumors reached an average volume of ~200 mm$^3$ animals were randomized and treatment was started. Animals were treated with Vehicle or Compound daily for 4 weeks. Tumor volume and body weight were monitored bi-weekly throughout the study. At the conclusion of the treatment period, plasma and tumor samples were taken for pharmacokinetic and pharmacodynamic analyses, respectively.

Example 50

Tamoxifen-resistant Breast Cancer Model; Xenograft Assay (MCF-7 derivative)

Female nu/nu mice (with supplemental 17-(Estradiol pellets; 0.72 mg; 60 day slow release) bearing MCF-7 tumors (mean tumor volume 200 mm$^3$) were treated with Tamoxifen (citrate) by oral gavage. Tumor volume (length×width$^2$/2) and body weight were monitored twice weekly. Following a significant anti-tumor response in which tumor volume remained static, evident tumor growth was first observed at approximately 100 days of treatment. At 120 days of treatment, tamoxifen dose was increased. Rapidly growing tumors were deemed tamoxifen resistant and selected for in vivo passage into new host animals. Tumor Fragments (~100 mm$^3$/animal) from the tamoxifen resistant tumors were subcutaneously implanted into the right flank of female nu/nu mice (with 17-β Estradiol pellets (0.72 mg; 60 day slow release)). Passaged tumors were maintained under constant Tamoxifen selection, and Tumor volume (length×width$^2$/2) was monitored weekly. When tumor volume reached ~150-250 mm$^3$, animals were randomized into treatment groups (mean tumor volume 200 mm$^3$) and tamoxifen treatment was terminated (except for a tamoxifen control arm). Animals were treated with Vehicle or Compound daily for 4 weeks. Tumor volume and body weight were monitored twice weekly for the duration of the study. At the conclusion of the treatment period; plasma and tumor samples were taken for pharmacokinetic and pharmacodynamic analyses, respectively.

Example 51

Ovarian Cancer Model; Xenograft Assay (BG-1)

Time release pellets (0.72 mg 17-β Estradiol/60 days) were subcutaneously implanted into female nu/nu mice. BG-1 cells were grown in DMEM Ham's F-12 50/50 containing 10% FBS, 10 mM Sodium Pyruvate, 10 mM Non-Essential Amino Acids at 5% $CO_2$, 37° C. Cells were spun down and re-suspended in 50% DMEM Ham's F-12 (serum free) and 50% Matrigel at $5×10^7$ cells/mL. BG-1 cells were subcutaneously injected (100 μL/animal) on the right flank 2-3 days post pellet implantation. Tumor volume (length×width$^2$/2) was monitored bi-weekly. When tumors reached an average volume of ~250 mm$^3$ animals were randomized and treatment was started. Animals were treated with Vehicle or Compound daily for 4 weeks. Tumor volume and body weight were monitored bi-weekly throughout the study. At the conclusion of the treatment period; plasma and tumor samples were taken for pharmacokinetic and pharmacodynamic analyses, respectively.

Example 52

Immature Uterine Wet Weight-Antagonist Mode

Female immature CD-IGS rats (21 days old upon arrival) were treated for three days Animals were dosed daily for three days. Vehicle or test compound was administered orally by gavage followed 15 minutes later by an oral dose of 0.1 mg/kg Ethynyl Estradiol. On the fourth day 24 hours after dose, plasma was collected for pharmacokinetic analysis. Immediately following plasma collection, the animals were euthanized and the uterus was removed and weighed.

Example 53

Immature Uterine Wet Weight-Agonist Mode

Female immature CD-IGS rats (21 days old upon arrival) were treated for three days. Animals were dosed daily for three days. Vehicle or test compound was administered orally by gavage followed 15 minutes later by a second oral dose of vehicle. On the fourth day 24 hours after dose, plasma was collected for pharmacokinetic analysis Immediately following plasma collection, the animals were euthanized and the uterus was removed and weighed.

Example 54

Breast Cancer Clinical Trial

Purpose: The purpose of this study is to assess the efficacy of treatment of metastatic breast cancer with a compound of Formula (I), or a pharmaceutically acceptable salt thereof, collect information on any side effects the compound of Formula (I), or a pharmaceutically acceptable salt thereof, may cause, and evaluate the pharmacokinetic properties of the compound of Formula (I), or a pharmaceutically acceptable salt thereof.

Intervention: Patients are administered 1-50 mg/kg of a compound of Formula (I), or a pharmaceutically acceptable salt thereof, per day or twice a day.

Outcome Measures: Primary Outcome Measures: The primary outcome measure is the patient's tumor response and/or disease control to a compound of Formula (I), or a pharmaceutically acceptable salt thereof, as first- and/or second-line treatment in patients with estrogen receptor (ER) positive metastatic breast cancer.

Secondary Outcome Measures: The second outcome measures are (a) an evaluation of the side-effects of a compound of Formula (I), or a pharmaceutically acceptable salt thereof; (b) an evaluation of the pharmacokinetic properties of a compound of Formula (I), or a pharmaceutically acceptable salt thereof; (c) an evaluation of the proportion of patients that have complete or partial response or stable disease at defined timepoint; (d) an evaluation of the time to progression and overall survival of patients treated with a compound of Formula (I), or a pharmaceutically acceptable salt thereof; and (e) biomarkers predictive of clinical response.

Detailed Description: Patients will be given a compound of Formula (I), or a pharmaceutically acceptable salt thereof, orally once or twice a day. Prior to each dosing cycle of a compound of Formula (I), or a pharmaceutically acceptable salt thereof, a physical exam, blood work and assessment of any side effects will be performed. Every 12 weeks the patient's cancer will be re-evaluated with either a CT scan or MRI to determine whether the treatment is working. Participation in this study will last until disease progression or unacceptable toxicity.

Eligibility: Female subjects, 18 years and older.

Inclusion Criteria: Histologically or cytologically confirmed diagnosis of invasive breast cancer, Stage IV disease. At least one measurable target lesion as defined by RECIST that has not been previously treated with local therapy. Postmenopausal status. ER positive breast cancer. HER2-negative breast cancer. Up to one prior hormonal therapy for advanced or metastatic disease. ECOG performance status 0-1. Life expectancy>12 weeks. Adequate liver and bone marrow function: AST<2.5×ULN; Bilirubin<1.5×ULN; ANC>1,500/ul; platelet count>100,000/ul; normal PT and PTT. At least 2 weeks since prior radiation and recovered from treatment-related toxicity.

Exclusion Criteria: HER2-positive breast cancer. Prior chemotherapy regimen for metastatic disease. History of, or presence of brain metastases. Concurrent investigational drug treatment. Prior bone marrow or stem cell transplant. History of other malignancy within the last 5 years, not including curatively-treated carcinoma in situ of the cervix or non-melanoma skin cancer. Uncontrolled infection. Active bleeding, or history of bleeding requiring transfusion.

Active cardiac disease. Serious medical or psychiatric illness.

Example 55

Parenteral Pharmaceutical Composition

To prepare a parenteral pharmaceutical composition suitable for administration by injection (subcutaneous, intravenous), 100 mg of a compound of Formula (I), or a water-soluble salt of a compound of Formula (I), is dissolved in sterile water and then mixed with 10 mL of 0.9% sterile saline. The mixture is incorporated into a dosage unit form suitable for administration by injection In another embodiment, the following ingredients are mixed to form an injectable formulation: 1.2 g of a compound of Formula (I), or a pharmaceutically acceptable salt thereof, 2.0 mL of sodium acetate buffer solution (0.4 M), HCl (1 N) or NaOH (1 M) (q.s. to suitable pH), water (distilled, sterile) (q.s. to 20 mL). All of the above ingredients, except water, are combined and stirred and if necessary, with slight heating if necessary. A sufficient quantity of water is then added.

Example 56

Oral Solution

To prepare a pharmaceutical composition for oral delivery, an aqueous 20% propylene glycol solution is prepared. To this is added a sufficient amount of compound of Formula (I), or a pharmaceutically acceptable salt thereof, to provide a 20 mg/mL solution.

Example 57

Oral Capsule

To prepare a pharmaceutical composition for oral delivery, 100-500 mg of a compound of Formula (I), or a pharmaceutically acceptable salt thereof, is mixed with starch. The mixture is incorporated into an oral dosage unit such as a hard gelatin capsule, which is suitable for oral administration. In another embodiment, 100-500 mg of a compound of Formula (I), or a pharmaceutically acceptable salt thereof, is placed into Size 4 capsule, or size 1 capsule (hypromellose or hard gelatin) and the capsule is closed.

Example 58

Oral Tablet

A tablet is prepared by mixing 48% by weigh of a compound of Formula (I), or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

Example 59

Topical Gel Composition

To prepare a pharmaceutical topical gel composition, a compound of Formula (I), or a pharmaceutically acceptable salt thereof, is mixed with hydroxypropyl celluose, propylene glycol, isopropyl myristate and purified alcohol USP. The resulting gel mixture is then incorporated into containers, such as tubes, which are suitable for topical administration.

The examples and embodiments described herein are for illustrative purposes only and various modifications or changes suggested to persons skilled in the art are to be included within the spirit and purview of this application and scope of the appended claims.

What is claimed is:

1. A compound of Formula (I), or a pharmaceutically acceptable salt, or N-oxide thereof:

Formula (I)

wherein,
Z is —OH or —OR$^{10}$;
R$^2$ is C$_1$-C$_4$alkyl, C$_1$-C$_4$-fluoroalkyl, C$_1$-C$_4$deuteroalkyl, C$_3$-C$_6$cycloalkyl, or —C$_1$-C$_4$alkylene-W;
  W is hydroxy, halogen, CN, C$_1$-C$_4$alkyl, C$_1$-C$_4$haloalkyl, C$_1$-C$_4$alkoxy, C$_1$-C$_4$haloalkoxy, or C$_3$-C$_6$cycloalkyl;
each R$^3$ is independently halogen, C$_1$-C$_4$alkyl, or C$_1$-C$_4$-fluoroalkyl;
each R$^4$ is independently halogen, —CN, —OR$^9$, —S(=O)$_2$R$^{10}$, C$_1$-C$_4$alkyl, C$_1$-C$_4$-fluoroalkyl, or C$_1$-C$_4$heteroalkyl;
each R$^5$ is independently halogen, —CN, —OR$^9$, —S(=O)$_2$R$^{10}$, C$_1$-C$_4$alkyl, C$_1$-C$_4$-fluoroalkyl, or C$_1$C$_4$heteroalkyl;
R$^6$ is H, C$_1$-C$_4$alkyl, or halogen;
R$^7$ is H, C$_1$-C$_4$alkyl, or halogen;
R$^9$ is H, C$_1$-C$_6$alkyl, C$_1$-C$_6$-fluoroalkyl, or C$_3$-C$_6$cycloalkyl;
R$^{10}$ is C$_1$-C$_6$alkyl;
m is 0, 1, or 2;
n is 0, 1, 2, 3, or 4; and
p is 0, 1, or 2.

2. The compound of claim 1, or a pharmaceutically acceptable salt, or N-oxide thereof, wherein:
Z is —OH;
R$^6$ is H, —CH$_3$, F, or Cl;
R$^7$ is H, —CH$_3$, F, or Cl;
each R$^3$ is independently halogen, C$_1$-C$_4$alkyl, or C$_1$-C$_4$-fluoroalkyl;
each R$^4$ is independently halogen, —CN, —OH, —OR$^9$, —S(=O)$_2$R$^{10}$, C$_1$-C$_4$alkyl, C$_1$-C$_4$-fluoroalkyl, C$_1$-C$_4$heteroalkyl, C$_1$-C$_4$-fluoroalkoxy, or C$_1$-C$_4$alkoxy;
each R$^5$ is independently halogen, C$_1$-C$_4$alkyl, or C$_1$-C$_4$-fluoroalkyl;
m is 0 or 1;
n is 0, 1, or 2; and
p is 0 or 1.

3. The compound of claim 2, or a pharmaceutically acceptable salt, or N-oxide thereof, wherein:
R$^2$ is C$_1$-C$_4$alkyl, C$_1$-C$_4$-fluoroalkyl, C$_1$-C$_4$deuteroalkyl, C$_3$-C$_6$cycloalkyl, or —C$_1$-C$_4$alkylene-W;
  W is hydroxy, halogen, CN, C$_1$-C$_4$alkoxy, or C$_3$-C$_6$cycloalkyl.

4. The compound of claim 3, or a pharmaceutically acceptable salt, or N-oxide thereof, wherein:
Z is —OH;
R$^6$ is H;
R$^7$ is H;
m is 0;
n is 0, 1, or 2; and
p is 0.

5. The compound of claim 1, wherein the compound of Formula (I) has the structure of Formula (II), or a pharmaceutically acceptable salt, or N-oxide thereof:

Formula (II)

6. The compound of claim 5, or a pharmaceutically acceptable salt, or N-oxide thereof, wherein:
each R$^3$ is independently F, Cl, or —CH$_3$;
each R$^4$ is independently halogen, —CN, —OH, —S(=O)$_2$CH$_3$, —S(=O)$_2$CH$_2$CH$_3$, —CH$_3$, —CH$_2$CH$_3$, —CF$_3$, —CH$_2$OH, —OCF$_3$, —OCH$_3$, or —OCH$_2$CH$_3$;
each R$^5$ is independently F, Cl, or —CH$_3$;
m is 0 or 1;
n is 0, 1, or 2; and
p is 0 or 1.

7. The compound of claim 6, or a pharmaceutically acceptable salt, or N-oxide thereof, wherein:
R$^2$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH$_2$F, —CHF$_2$, —CF$_3$, —CH$_2$CF$_3$, —CD$_3$, —CH$_2$CD$_3$, —CD$_2$CD$_3$, cyclopropyl, cyclobutyl, cyclopentyl, cyclohexyl, —CH$_2$—W, or —CH$_2$CH$_2$—W;
  W is hydroxy, F, Cl, —CN, —OCH$_3$, —OCH$_2$CH$_3$, —OCH$_2$CH$_2$CH$_3$, —OCH(CH$_3$)$_2$, cyclopropyl, cyclobutyl, cyclopentyl, or cyclohexyl.

8. The compound of claim 5, or a pharmaceutically acceptable salt, or N-oxide thereof, wherein:
R$^2$ is —CH$_2$CH$_3$;
each R$^4$ is independently F, Cl, —CN, —OH, —CH$_3$, —CH$_2$CH$_3$, —CF$_3$, —CH$_2$OH, —OCF$_3$, —OCH$_3$, or —OCH$_2$CH$_3$;
m is 0;
n is 0, 1, or 2; and
p is 0.

9. The compound of claim 1, wherein the compound is:
(E)-Ethyl 3-(4-((E)-1-(1H-indazol-5-yl)-2-phenylbut-1-en-1-yl)phenyl)acrylate; (E)-3-(4-((E)-1-(1H-Indazol-5-yl)-2-phenylbut-1-en-1-yl)phenyl)acrylic acid; (E)-3-(4-((E)-2-(4-Fluorophenyl)-1-(1H-indazol-5-yl)but-1-en-1-yl)phenyl) acrylic acid; (E)-3-(4-((E)-2-(4-Chlorophenyl)-1-(1H-indazol-5-yl)but-1-en-1-yl)phenyl)acrylic acid; (E)-3-(4-((E)-1-(1H-Indazol-5-yl)-2-(3-methoxyphenyl)but-1-en-1-yl)phenyl)acrylic acid; (E)-3-(4-((E)-2-(3-(Hydroxymethyl)phenyl)-1-(1H-indazol-5-yl)but-1-en-1-yl) phenyl)acrylic acid; (E)-3-(4-((E)-2-(4-(Hydroxymethyl)phenyl)-1-(1H-indazol-5-yl)but-1-en-1-yl)phenyl)acrylic acid; (E)-3-(4-((E)-2-(2-(Hydroxymethyl)phenyl)-1-(1H-indazol-5-yl) but-1-en-1-yl)phenyl)acrylic acid; (E)-3-(4-((E)-1-(1H-Indazol-5-yl)-2-(o-tolyl)but-1-en-1-yl)phenyl)acrylic acid; (E)-3-(4-((E)-1-(1H-Indazol-5-yl)-2-(m-tolyl)but-1-en-1-yl)phenyl) acrylic acid; (E)-3-(4-((E)-1-(1H-Indazol-5-yl)-2-(p-tolyl)but-1-en-1-yl)phenyl)acrylic acid; (E)-3-(4-((E)-1-(1H-Indazol-5-yl)-2-(2-methoxyphenyl)but-1-en-1-yl)phenyl)

acrylic acid; (E)-3-(4-((E)-1-(1H-Indazol-5-yl)-2-(4-methoxyphenyl)but-1-en-1-yl)phenyl)acrylic acid; ((E)-3-(4-((E)-2-(2-Chlorophenyl)-1-(1H-indazol-5-yl)but-1-en-1-yl)phenyl)acrylic acid; (E)-3-(4-((E)-2-(3-Chlorophenyl)-1-(1H-indazol-5-yl)but-1-en-1-yl)phenyl)acrylic acid; (E)-3-(4-((E)-2-(2-Fluorophenyl)-1-(1H-indazol-5-yl)but-1-en-1-yl)phenyl)acrylic acid; (E)-3-(4-((E)-2(3-Fluorophenyl)-1-(1H-indazol-5-yl)but-1-en-1-yl)phenyl)acrylic acid; (E)-3-(4-((E)-2-(2-Ethylphenyl)-1-(1H-indazol-5-yl)but-1-en-1-yl)phenyl)acrylic acid; (E)-3-(4-((E)-1-(1H-Indazol -5-yl)-2-(2-(trifluoromethyl)phenyl)but-1-en-1-yl)phenyl)acrylic acid; (E)-3-(4-((E)-4-Chloro-1-(1H-indazol-5-yl)-2-phenylbut-1-en-1-yl)phenyl)acrylic acid; (E)-3-(4-((E)-2-(2-Cyanophenyl)-1-(1H-indazol-5-yl)but-1-en-1-yl)phenyl) acrylic acid; (E)-3-(4-((E)-2-(2,4-Difluorophenyl)-1-(1H-indazol -5-yl)but-1-en-1-yl)phenyl)acrylic acid; (E)-3-(4-((E)-2-(2-Chloro-3-fluorophenyl)-1-(1H-indazol -5-yl)but-1-en-1-yl)phenyl)acrylic acid; (E)-3-(4-((E)-2-Cyclopropyl-1-(1H-indazol-5-yl) -2-phenylvinyl)phenyl)acrylic acid; (E)-3-(4-((E)-2-(4-Fluoro-2-methylphenyl)-1-(1H-indazol-5-yl) but-1-en-1-yl)phenyl)acrylic acid; (E)-3-(4-((E)-2-(2,6-Difluorophenyl)-1-(1H-indazol-5-yl)but-1-en-1-yl)phenyl) acrylic acid; (E)-3-(4-((E)-2-(2,6-Dichlorophenyl)-1-(1H-indazol-5-yl)but-1-en-1-yl)phenyl)acrylic acid; (E)-3-(4-((E)-4,4,4-Trideutero-1-(1H-indazol-5-yl)-2-phenylbut-1-en-1-yl)phenyl)acrylic acid; (E)-3-(4-((E)-2(4-Fluoro-3-methylphenyl)-1-(1H-indazol -5-yl)but-1-en-1-yl)phenyl)acrylic acid; (E)-3-(4-((E)-2-(5-Fluoro-2-methylphenyl)-1-(1H-indazol -5-yl)but-1-en-1-yl)phenyl)acrylic acid; (E)-3-(4-((E)-2-(2,3-Difluorophenyl)-1-(1H-indazol -5-yl)but-1-en-1-yl)phenyl)acrylic acid; (E)-3-(4-((E)-2-(2,5-Difluorophenyl)-1-(1H-indazol -5-yl)but-1-en-1-yl)phenyl)acrylic acid; (E)-3-(4-((E)-2-(2-Chloro-5-fluorophenyl)-1-(1H-indazol -5-yl)but-1-en-1-yl)phenyl)acrylic acid; (E)-3-(4-((E)-2-(2-Chloro-6-methylphenyl)-1-(1H-indazol-5-yl) but-1-en-1-yl)phenyl)acrylic acid; (E)-3-(4-((E)-1-(7-Chloro-1H-indazol-5-yl) -2-phenylbut-1-en-1-yl)phenyl)acrylic acid; (E)-3-(4-((E)-1-(4-Methyl-1H-indazol-5-yl)-2-phenylbut-1-en-1-yl)phenyl)acrylic acid; (E)-3-(4-((E)-1-(7-Methyl-1H-indazol-5-yl)-2-phenylbut-1-en-1-yl)phenyl) acrylic acid; (E)-3-(4-((E)-1-(6-Methyl-1H-indazol-5-yl)-2-phenylbut-1-en-1-yl)phenyl)acrylic acid; (E)-3-(4-((E)-1-(3-Methyl-1H-indazol-5-yl)-2-phenylbut-1-en-1-yl)phenyl) acrylic acid; (E)-3-(4-((E)-1-(3-Chloro-1H-indazol-5-yl)-2-phenylbut-1-en-1-yl)phenyl)acrylic acid; (E)-3-(4-((E)-2-(4-Chloro-2-methylphenyl)-1-(1H-indazol -5-yl)but-1-en-1-yl) phenyl)acrylic acid; (E)-3-(4-((E)-1-(1H-Indazol-5-yl)-2-phenylprop -1-en-1-yl)phenyl)acrylic acid; (E)-3-(4-((E)-1-(1H-Indazol-5-yl)-2-phenylpent-1-en-1-yl)phenyl)acrylic acid; (E)-3-(4-((E)-2-(3-Cyanophenyl)-1-(1H-indazol-5-yl) but-1-en-1-yl)phenyl)acrylic acid; (E)-3-(4-((E)-2-(4-Cyanophenyl)-1-(1H-indazol-5-yl)but-1-en-1-yl)phenyl) acrylic acid; (E)-3-(4-((E)-4-Hydroxy-1-(1H-indazol-5-yl)-2-phenylbut-1-en-1-yl)phenyl)acrylic acid; (E)-3-(4-((E)-1-(1H-Indazol-5-yl)-4-methoxy-2-phenylbut-1-en-1-yl) phenyl)acrylic acid; (E)-3-(4-((Z)-1-(1H-Indazol-5-yl)-3-methoxy-2-phenylprop-1-en-1-yl)phenyl)acrylic acid; (E)-3-(4-((E)-1-(4-Fluoro-1H-indazol-5-yl)-2-phenylbut-1-en-1-yl)phenyl)acrylic acid; (E)-3-(4-((E)-1-(6-Chloro-1H-indazol-5-yl)-2-phenylbut-1-en-1-yl)phenyl)acrylic acid; (E)-3-(4-((E)-1-(1H-Indazol-5-yl)-4-methyl-2-phenylpent-1-en-1-yl)phenyl)acrylic acid; (E)-3-(4-((E)-1-(4-Chloro-1H-indazol-5-yl)-2-phenylbut-1-en-1-yl)phenyl)acrylic acid; (E)-3-(4-((E)-2-Cyclopentyl-1-(1H-indazol-5-yl)-2-phenylvinyl)phenyl)acrylic acid; (E)-3-(4-((E)-2-Cyclohexyl-1-(1H-indazol-5-yl)-2-phenylvinyl)phenyl)acrylic acid; (E)-3-(4-((E)-1-(1H-Indazol-5-yl)-3-methyl-2-phenylbut-1-en-1-yl)phenyl)acrylic acid; (E)-3-(4-((E)-3-Cyclopropyl-1-(1H-indazol-5-yl)-2-phenylprop-1-en-1-yl)phenyl)acrylic acid; (E)-3-(4-((E)-2-(2-Chlorophenyl)-2-cyclopropyl-1-(1H-indazol-5-yl)vinyl)phenyl)acrylic acid; (E)-3-(4-((E)-1-(6-Fluoro-1H-indazol-5-yl)-2-phenylbut-1-en-1-yl)phenyl)acrylic acid; (E)-3-(4-((E)-1-(1H-Indazol-5-yl)-2-phenylhex-1-en-1-yl)phenyl)acrylic acid; (E)-3-(4-((E)-3-Cyclopentyl-1-(1H-indazol-5-yl)-2-phenylprop-1-en-1-yl)phenyl)acrylic acid; (E)-3-(4-((E)-2-(2-Chloro-4-fluorophenyl)-1-(4-fluoro-1H-indazol-5-yl)but-1-en-1-yl) phenyl)acrylic acid; (E)-3-(4-((E)-1-(7-Fluoro-1H-indazol-5-yl)-2-phenylbut-1-en-1-yl)phenyl)acrylic acid; (E)-3-(4-((E)-2-(2-Chloro-4-fluorophenyl)-1-(1H-indazol-5-yl)-4-methylpent-1-en-1-yl)phenyl)acrylic acid; (E)-3-(4-((Z)-3,3-Difluoro-1-(1H-indazol-5-yl)-2-phenylprop-1-en-1-yl) phenyl)acrylic acid; (E)-3-(4-((E)-2-(2-Chloro-4-fluorophenyl)-1-(7-fluoro -1H-indazol-5-yl)but-1-en-1-yl) phenyl)acrylic acid; (E)-3-(4-((E)-4-Fluoro-1-(1H-indazol-5-yl)-2-phenylbut-1-en-1-yl)phenyl)acrylic acid; (E)-3-(4-((E)-4-Chloro-2-(2-chloro-4-fluorophenyl)-1-(1H-indazol-5-yl)but-1-en-1-yl)phenyl)acrylic acid; (E)-3-(4-((Z)-3,3,3-Trifluoro-1-(1H-indazol -5-yl)-2-phenylprop-1-en-1-yl) phenyl)acrylic acid; (E)-3-(4-((E)-1-(4-Fluoro-1H-indazol-5-yl)-2-(4-fluoro-2-methylphenyl)but-1-en-1-yl)phenyl) acrylic acid; (E)-3-(4-((E)-2-(4-Chloro-2-methylphenyl)-1-(4-fluoro-1H-indazol-5-yl)but-1-en-1-yl)phenyl)acrylic acid; (E)-3-(4-((E)-2-Cyclopropyl-1-(4-fluoro-1H-indazol-5-yl)-2-(4-fluoro-2-methylphenyl)vinyl)phenyl)acrylic acid; (E)-3-(4-((E)-2-(4-Chloro-2-methylphenyl)-2-cyclopropyl-1-(4-fluoro-1H-indazol-5-yl)vinyl)phenyl)acrylic acid; (E)-3-(4-((E)-1-(4-Chloro-1H-indazol-5-yl)-2-(2-chloro-4-fluorophenyl)but-1-en-1-yl)phenyl)acrylic acid; (E)-3-(4((Z)-2-(2-Chloro-4-fluorophenyl)-3,3-difluoro-1-(1H-indazol-5-yl) prop-1-en-1-yl)phenyl)acrylic acid; (E)-3-(4-((E)-2-Cyclopropyl-1-(4-fluoro-1H-indazol-5-yl)-2-phenylvinyl) phenyl)acrylic acid; (E)-3-(4-((E)-4-Chloro-1-(4-fluoro-1H-indazol-5-yl)-2-phenylbut-1-en-1-yl)phenyl)acrylic acid; (E)-3-(4-((E)-4-Chloro-2-(2-chloro-4-fluorophenyl)-1-(4-fluoro-1H-indazol-5-yl)but-1-en-1-yl)phenyl)acrylic acid; (E)-3-(4-((E)-4-Fluoro-2-(4-fluorophenyl)-1-(1H-indazol-5-yl)but-1-en-1-yl)phenyl)acrylic acid; (E)-3-(4-((E)-4-Fluoro-1-(4-fluoro-1H-indazol-5-yl)-2-phenylbut-1-en-1-yl)phenyl)acrylic acid; (E)-3-(4-((E)-1-(1H-Indazol-5-yl)-5-methoxy-2-phenylpent-1-en-1-yl)phenyl)acrylic acid; (E)-3-(4-((E)-1-(1H-Indazol-5-yl)-6-methoxy-2-phenylhex-1-en-1-yl)phenyl)acrylic acid; (E)-3-(4-((E)-2-(2-Chloro-4-fluorophenyl)-1-(1H-indazol-5-yl)-3-methylbut-1-en-1-yl) phenyl)acrylic acid; (E)-3-(4-((E)-1-(1H-Indazol-5-yl)-2-(3-(trifluoromethoxy)phenyl)but-1-en-1-yl)phenyl)acrylic acid; (E)-3-(4-((E)-2-Cyclobutyl-1-(1H-indazol-5-yl)-2-phenylvinyl)phenyl)acrylic acid; (E)-3-(4-((E)-2-(2-Chloro-4-fluorophenyl)-2-cyclobutyl-1-(1H-indazol-5-yl)vinyl)phenyl)acrylic acid; (E)-3-(4-((E) -1-(3-Fluoro-1H-indazol-5-yl)-2-phenylbut-1-en-1-yl)phenyl)acrylic acid; (E)-3-(4-((E)-2-Cyclobutyl-1-(3-fluoro-1H-indazol-5-yl)-2-phenylvinyl)phenyl)acrylic acid; (E)-3-(4-((E)-2-(2-Chloro-4-fluorophenyl)-1-(3-fluoro-1H-indazol-5-yl)but-1-en-1-yl) phenyl)acrylic acid; (E)-3-(4-((E)-2-(2-Chloro-4-fluorophenyl)-2-cyclobutyl-1-(3-fluoro-1H-indazol-5-yl) vinyl)phenyl)acrylic acid; (E)-Ethyl 3-(4-((E)-2-(4-fluorophenyl)-1-(1H-indazol-5-yl)but-1-en-1-yl)phenyl) acrylate; (E)-Ethyl 3-(4-((E)-1-(1H-Indazol-5-yl)-2-(2-methoxyphenyl)but-1-en-1-yl)phenyl)acrylate; (E)-Ethyl 3-(4-((E)-1-(1H-Indazol-5-yl)-2-(4-methoxyphenyl)but-1-en-1-yl)phenyl)acrylate; (E)-3-(4-((E)-2-(3-Hydroxyphenyl)-1-(1H-indazol-5-yl)but-1-en-1-yl)phenyl)acrylic acid; (E)-3-(4-((E)-2-(2-Hydroxyphenyl)-1-(1H-indazol-5-yl)

but-1-en-1-yl)phenyl)acrylic acid; (E)-3-(4-((E)-2-(4-Hydroxyphenyl)-1-(1H-indazol-5-yl)but-1-en-1-yl)phenyl)acrylic acid; (E)-3-(4-((E)-2-(3-Butoxyphenyl)-1-(1H-indazol-5-yl)but-1-en-1-yl)phenyl)acrylic acid; (E)-3-(4-((E)-2-(4-Butoxyphenyl)-1-(1H-indazol-5-yl)but-1-en-1-yl)phenyl)acrylic acid; (E)-3-(4-((E)-1-(1H-Indazol -5-yl)-2-(2-(methylsulfonyl)phenyl)but-1-en-1-yl)phenyl)acrylic acid; (E)-3-(4-((E)-1-(1H-Indazol-5-yl)-2-phenylbut-1-en-1-yl)phenyl)-2-methylacrylic acid; (E)-3-(4-((Z)-1-(1H-Indazol -5-yl)-2-phenylbut-1-en-1-yl)-3-methylphenyl)acrylic acid; (E)-3-(4-((E)-1-(1H-Indazol -5-yl)-2-phenylbut-1-en-1-yl)-2-methylphenyl)acrylic acid; (E)-3-(4-((Z)-1-(1H-Indazol-5-yl)-2-phenylbut-1-en-1-yl)-2-chlorophenyl)acrylic acid; (Z)-3-(4-((E)-1-(1H-Indazol-5-yl)-2-phenylbut -1-en-1-yl)phenyl)-2-fluoroacrylic acid; (Z)-3-(4-((E)-1-(1H-Indazol-5-yl)-2-phenylbut-1-en-1-yl)phenyl)-2-chloroacrylic acid; (E)-3-(4-((Z)-1-(1H-Indazol-5-yl)-2-phenylbut-1-en-1-yl)-3-fluorophenyl)acrylic acid; (E)-3-(4-((Z)-1-(1H-Indazol-5-yl)-2-phenylbut-1-en-1-yl)-2-fluorophenyl)acrylic acid; (E)-3-(4-((Z)-1-(1H-Indazol-5-yl)-2-phenylbut-1-en-1-yl)-2-(trifluoromethyl)phenyl)acrylic acid; (E)-3-(4-((Z)-1-(1H-Indazol-5-yl)-2-phenylbut-1-en-1-yl)-3-methoxyphenyl)acrylic acid; (E)-3-(4-((Z)-1-(1H-Indazol-5-yl)-2-phenylbut-1-en-1-yl)-2-methoxyphenyl)acrylic acid; (E)-Ethyl 3-(4-((E)-2-(2-chloro-4-fluorophenyl)-1-(1H-indazol-5-yl)but-1-en-1-yl)phenyl)acrylate hydrochloride; (E)-3-(4-((E)-2-(2-Chloro-4-fluorophenyl)-1-(1H-indazol-5-yl)but-1-en-1-yl)phenyl)acrylic acid; (E)-Ethyl 3-(4-((E)-2-(2,4-dichlorophenyl)-1-(1H-indazol-5-yl)but-1-en-1-yl)phenyl)acrylate; (E)-3-(4-((E)-2-(2,4-Dichlorophenyl)-1-(1H-indazol -5-yl)but-1-en-1-yl)phenyl)acrylic acid; (E)-3-(4-((E)-2-(4-Chloro-2-(trifluoromethyl)phenyl)-1-(1H-indazol-5-yl)but-1-en-1-yl)phenyl)acrylic acid; (E)-3-(4-((E)-2-(2-Chloro-4-fluorophenyl)-2-cyclopropyl-1-(1H-indazol-5-yl)vinyl)phenyl)acrylic acid; (E)-3-(4-((E)-2-(4-Fluoro-2-(trifluoromethyl)phenyl)-1-(1H-indazol-5-yl)but-1-en-1-yl)phenyl)acrylic acid; (E)-3-(4-(1-(4-Fluoro-1H-indazol-5-yl)-2-(4-fluoro-2-(trifluoromethyl)phenyl)butyl)phenyl)acrylic acid; (E)-3-(4-((E)-2-(2,4-Dichlorophenyl)-1-(4-fluoro-1H-indazol-5-yl)but-1-en-1-yl)phenyl)acrylic acid; (E)-3-(4-((E)-2-(4-Chloro-2-(trifluoromethyl)phenyl)-1-(4-fluoro-1H-indazol-5-yl)but-1-en-1-yl)phenyl)acrylic acid; (E)-3-(4-((E)-2-(2-Chloro-4-fluorophenyl)-4-fluoro-1-(1H-indazol-5-yl)but-1-en-1-yl)phenyl)acrylic acid; (E)-3-(4-((E)-2-(2-Chloro-4-methoxyphenyl)-1-(1H-indazol-5-yl)but-1-en-1-yl)phenyl)acrylic acid; (E)-3-(4-((E)-2-(2,4-Dichlorophenyl)-4-fluoro-1-(4-fluoro-1H-indazol-5-yl)but-1-en-1-yl)phenyl)acrylic acid; (E)-3-(4-((E)-2-Cyclopropyl-2-(2,4-dichlorophenyl)-1-(4-fluoro-1H-indazol-5-yl)vinyl)phenyl)acrylic acid; (E)-3-(4-((E)-2-(2-Chloro-4-fluorophenyl)-2-cyclopropyl-1-(4-fluoro-1H-indazol-5-yl)vinyl)phenyl)acrylic acid; (E)-3-(4-((E)-2-Cyclopropyl-2-(2,4-dichlorophenyl)-1-(1H-indazol-5-yl)vinyl)phenyl)acrylic acid; (E)-3-(4-((E)-2-(4-Chloro-2-methylphenyl)-2-cyclopropyl-1-(1H-indazol-5-yl)vinyl)phenyl)acrylic acid; (E)-3-(4-((E)-1-(1H-Indazol -5-yl)-2-(2-methyl-5-(methylsulfonyl)phenyl)but-1-en-1-yl)phenyl)acrylic acid; (E)-3-(4-((E)-1-(1H-Indazol-5-yl)-2-(4-methoxy-2-methylphenyl)but-1-en-1-yl)phenyl)acrylic acid; (E)-3-(4-((E)-2-(2-Fluoro-4-methoxyphenyl)-1-(1H-indazol-5-yl)but-1-en-1-yl)phenyl)acrylic acid; (E)-3-(4-((E)-2-(2-Chloro-5-methoxyphenyl)-1-(1H-indazol-5-yl)but-1-en-1-yl)phenyl)acrylic acid; (E)-3-(4-((E)-2-(2-Fluoro-4-(methylsulfonyl)phenyl)-1-(1H-indazol-5-yl)but-1-en-1-yl)phenyl)acrylic acid; (E)-3-(4-((E)-2-(2,4-Dichlorophenyl)-3,3,4,4,4-pentadeutero-1-(1H-indazol -5-yl)but-1-en-1-yl)phenyl)acrylic acid; (E)-3-(4-((E)-1-(1H-Indazol-5-yl)-2-(3-(methylsulfonyl)phenyl)but-1-en-1-yl)phenyl)acrylic acid; (E)-3-(4-((E)-2-(2,4-Dichlorophenyl) -1-(7-fluoro-1H-indazol-5-yl)but-1-en-1-yl)phenyl)acrylic acid; (E)-3-(4-((E)-2-(2-Chloro-3-methoxyphenyl)-1-(1H-indazol-5-yl)but-1-en-1-yl)phenyl)acrylic acid; (E)-3-(4-((E)-2-(2-Chloro -4-fluorophenyl)-3,3,4,4,4-pentadeutero-1-(1H-indazol-5-yl)but-1-en-1-yl)phenyl)acrylic acid; (E)-3-(4-((E)-2-(4-Chloro-2-cyanophenyl)-1-(1H-indazol-5-yl)but-1-en-1-yl)phenyl)acrylic acid; (E)-3-(4-((E)-2-(2-Cyano-4-fluorophenyl)-1-(1H-indazol-5-yl)but-1-en-1-yl)phenyl)acrylic acid; (E)-3-(4-((E)-2-(2-Cyano-4-(trifluoromethyl)phenyl)-1-(1H-indazol-5-yl)but-1-en-1-yl)phenyl)acrylic acid; (E)-3-(4-((E)-2-(2-Chloro-4-cyanophenyl)-1-(1H-indazol-5-yl)but-1-en-1-yl)phenyl)acrylic acid; (E)-3-(4-((E)-2-(3-Cyano-2-methylphenyl)-1-(1H-indazol-5-yl)but-1-en-1-yl)phenyl)acrylic acid; (E)-3-(4-((E)-2-(4-Cyano-2-methylphenyl)-1-(1H-indazol-5-yl)but-1-en-1-yl)phenyl)acrylic acid; (E)-3-(4-((E)-2-(5-Cyano-2-methylphenyl)-1-(1H-indazol-5-yl)but-1-en-1-yl)phenyl)acrylic acid; (E)-3-(4-((E)-2-(2-Cyano-4-methoxyphenyl)-1-(1H-indazol-5-yl)but-1-en-1-yl) phenyl)acrylic acid; (E)-3-(4-((E)-2-(2-Chlorophenyl)-1-(1-methyl-1H-indazol-5-yl)but-1-en-1-yl)phenyl)acrylic acid; (E)-3-(4-((E)-2-Cyclobutyl-1-(1-methyl-1H-indazol-5-yl)-2-phenylvinyl)phenyl)acrylic acid; (E)-3-(4-((E)-2-(2-Chloro-4-fluorophenyl)-1-(1-methyl-1H-indazol -5-yl)but-1-en-1-yl)phenyl)acrylic acid; or (E)-3-(4-((E)-2-(2-Chloro-4-fluorophenyl)-1-(1-(difluoromethyl)-1H-indazol-5-yl)but-1-en-1-yl)phenyl)acrylic acid; and a pharmaceutically acceptable salt, or N-oxide thereof.

10. A pharmaceutical composition comprising a compound of claim 1, or a pharmaceutically acceptable salt, or N-oxide thereof.

11. The pharmaceutical composition of claim 10, wherein the pharmaceutical composition is formulated for intravenous injection, subcutaneous injection, oral administration, or topical administration.

12. The pharmaceutical composition of claim 10, wherein the pharmaceutical composition is a tablet, a pill, a capsule, a liquid, a suspension, a gel, a dispersion, a solution, an emulsion, an ointment, or a lotion.

\* \* \* \* \*